United States Patent
Bayever et al.

(10) Patent No.: US 10,980,795 B2
(45) Date of Patent: *Apr. 20, 2021

(54) METHODS FOR TREATING PANCREATIC CANCER USING COMBINATION THERAPIES COMPRISING LIPOSOMAL IRINOTECAN

(71) Applicant: Ipsen Biopharm Ltd., Wrexham (GB)

(72) Inventors: Eliel Bayever, New York, NY (US); Navreet Dhindsa, Boston, MA (US); Jonathan Basil Fitzgerald, Arlington, MA (US); Peter Laivins, Rowayton, CT (US); Victor Moyo, Ringoes, NJ (US); Clet Niyikiza, Gulph Mills, PA (US); Jaeyeon Kim, Lexington, MA (US)

(73) Assignee: Ipsen Biopharm Ltd.

( * ) Notice: Subject to any disclaimer, the term of this patent is extended or adjusted under 35 U.S.C. 154(b) by 0 days.

This patent is subject to a terminal disclaimer.

(21) Appl. No.: 16/012,351

(22) Filed: Jun. 19, 2018

(65) Prior Publication Data
US 2019/0117643 A1    Apr. 25, 2019

Related U.S. Application Data

(63) Continuation of application No. 15/652,513, filed on Jul. 18, 2017, now abandoned, which is a continuation of application No. 15/341,377, filed on Nov. 2, 2016, now abandoned, which is a continuation of application No. 14/851,111, filed on Sep. 11, 2015, now Pat. No. 9,492,442, which is a continuation of application No. 14/406,776, filed as application No. PCT/US2013/045495 on Jun. 12, 2013, now Pat. No. 9,452,162.

(60) Provisional application No. 61/784,382, filed on Mar. 14, 2013, provisional application No. 61/659,211, filed on Jun. 13, 2012.

(51) Int. Cl.
| | |
|---|---|
| *A61K 31/4745* | (2006.01) |
| *A61K 9/00* | (2006.01) |
| *A61K 9/127* | (2006.01) |
| *A61K 31/513* | (2006.01) |
| *A61K 31/517* | (2006.01) |
| *A61K 31/519* | (2006.01) |
| *A61K 31/573* | (2006.01) |
| *A61K 45/06* | (2006.01) |

(52) U.S. Cl.
CPC ........ *A61K 31/4745* (2013.01); *A61K 9/0019* (2013.01); *A61K 9/127* (2013.01); *A61K 9/1271* (2013.01); *A61K 31/513* (2013.01); *A61K 31/517* (2013.01); *A61K 31/519* (2013.01); *A61K 31/573* (2013.01); *A61K 45/06* (2013.01)

(58) Field of Classification Search
CPC .................................................. A61K 31/4745
See application file for complete search history.

(56) References Cited

U.S. PATENT DOCUMENTS

| | | | |
|---|---|---|---|
| 4,604,463 | A | 8/1986 | Miyasaka et al. |
| 5,013,556 | A | 5/1991 | Woodle et al. |
| 5,077,056 | A | 12/1991 | Bally et al. |
| 5,192,549 | A | 3/1993 | Barenolz et al. |
| 5,316,771 | A | 5/1994 | Barenholz et al. |
| 5,538,954 | A | 7/1996 | Koch et al. |
| 5,543,152 | A | 8/1996 | Webb et al. |
| 5,593,622 | A | 1/1997 | Yoshioka et al. |
| 5,676,971 | A | 10/1997 | Yoshioka et al. |
| 5,783,568 | A | 7/1998 | Schlessinger et al. |
| 5,785,987 | A | 7/1998 | Hope et al. |
| 5,846,458 | A | 12/1998 | Yoshioka et al. |
| 6,110,491 | A | 8/2000 | Kirpotin |
| 6,210,707 | B1 | 4/2001 | Papahadjopoulos et al. |
| 6,214,388 | B1 | 4/2001 | Benz et al. |
| 6,241,999 | B1 | 6/2001 | Ye et al. |
| 6,355,268 | B1 | 3/2002 | Slater et al. |
| 6,403,569 | B1 | 6/2002 | Achterrath |
| 6,465,008 | B1 | 10/2002 | Slater et al. |
| 6,511,676 | B1 | 1/2003 | Boulikas |
| 6,545,010 | B2 | 4/2003 | Bissery |
| 6,720,001 | B2 | 4/2004 | Chen et al. |
| 6,787,132 | B1 | 9/2004 | Gabizon et al. |
| 6,794,370 | B2 | 9/2004 | Achterrath |
| 7,022,336 | B2 | 4/2006 | Papahadjopoulos et al. |
| 7,060,828 | B2 | 6/2006 | Madden et al. |
| 7,135,177 | B2 | 11/2006 | Benz et al. |

(Continued)

FOREIGN PATENT DOCUMENTS

| | | |
|---|---|---|
| CA | 2412790 A1 | 1/2002 |
| CN | 1829741 A | 9/2006 |

(Continued)

OTHER PUBLICATIONS

Verreault M, et al., "Vascular Normalization in Orthotopic Glioblastoma Following Intravenous Treatment with Lipid-Based Nanoparticulate Formulations of Irinotecan (Irinophore C™), Doxorubicin (Caelyx®) or Vincristine," BMC Cancer. 11:124, pp. 1-18 (2011).

(Continued)

*Primary Examiner* — Kortney L. Klinkel
*Assistant Examiner* — Tori Strong
(74) *Attorney, Agent, or Firm* — McNeill Baur PLLC

(57) ABSTRACT

Provided are methods for treating pancreatic cancer in a patient by administering liposomal irinotecan (MM-398) alone or in combination with additional therapeutic agents. In one embodiment, the liposomal irinotecan (MM-398) is co-administered with 5-fluorouracil and leucovorin.

15 Claims, 6 Drawing Sheets

(56) References Cited

U.S. PATENT DOCUMENTS

| | | |
|---|---|---|
| 7,219,016 B2 | 5/2007 | Rimm et al. |
| 7,244,448 B2 | 7/2007 | Madden et al. |
| 7,244,826 B1 | 7/2007 | Marks et al. |
| 7,507,407 B2 | 3/2009 | Benz et al. |
| 7,829,113 B2 | 11/2010 | Okada et al. |
| 7,842,676 B2 | 11/2010 | Janoff et al. |
| 7,846,440 B2 | 12/2010 | Schoeberl et al. |
| 7,846,473 B2 | 12/2010 | Yoshino et al. |
| 7,850,990 B2 | 12/2010 | Tardi et al. |
| 7,871,620 B2 | 1/2011 | Benz et al. |
| 7,892,554 B2 | 2/2011 | Marks et al. |
| 8,067,432 B2 | 11/2011 | Anderson et al. |
| 8,147,867 B2 | 4/2012 | Hong et al. |
| 8,329,213 B2 | 12/2012 | Hong et al. |
| 8,496,961 B2 | 7/2013 | Hong et al. |
| 8,658,203 B2 | 2/2014 | Drummond et al. |
| 8,703,181 B2 | 4/2014 | Hong et al. |
| 8,992,970 B2 | 3/2015 | Hong et al. |
| 9,339,497 B2 | 5/2016 | Bayever et al. |
| 9,364,473 B2 | 6/2016 | Bayever et al. |
| 9,452,162 B2 | 9/2016 | Bayever et al. |
| 9,492,442 B2 | 11/2016 | Bayever et al. |
| 9,511,155 B2 | 12/2016 | Drummond et al. |
| 9,616,081 B2 | 4/2017 | Okabe |
| 9,717,723 B2 | 8/2017 | Hong et al. |
| 9,717,724 B2 | 8/2017 | Bayever et al. |
| 9,724,303 B2 | 8/2017 | Hong et al. |
| 9,730,891 B2 | 8/2017 | Hong et al. |
| 9,737,528 B2 | 8/2017 | Drummond et al. |
| 9,782,349 B2 | 10/2017 | Hong et al. |
| 9,895,365 B2 | 2/2018 | Blanchette et al. |
| 10,350,201 B2 | 7/2019 | Hong et al. |
| 10,413,510 B2 | 9/2019 | Hong et al. |
| 10,456,360 B2 | 10/2019 | Drummond et al. |
| 10,478,428 B2 | 11/2019 | Blanchette et al. |
| 10,722,508 B2 | 7/2020 | Hong et al. |
| 2002/0035091 A1 | 3/2002 | Govindarajan et al. |
| 2002/0102298 A1 | 8/2002 | Needham |
| 2002/0146450 A1 | 10/2002 | Slater et al. |
| 2002/0192275 A1 | 12/2002 | Zalipsky et al. |
| 2003/0138481 A1 | 7/2003 | Zadi |
| 2004/0002505 A1 | 1/2004 | Ozawa et al. |
| 2004/0071768 A1 | 4/2004 | Sarris et al. |
| 2007/0110798 A1 | 5/2007 | Drummond et al. |
| 2007/0219268 A1 | 9/2007 | Hausheer |
| 2007/0265324 A1 | 11/2007 | Wernet et al. |
| 2008/0108135 A1 | 5/2008 | Marks et al. |
| 2009/0123419 A1 | 5/2009 | Sherman et al. |
| 2009/0149397 A1 | 6/2009 | Ossovskaya et al. |
| 2010/0056761 A1 | 3/2010 | Schoeberl et al. |
| 2010/0068255 A1 | 3/2010 | Benz et al. |
| 2011/0059076 A1 | 3/2011 | McDonagh et al. |
| 2011/0104256 A1 | 5/2011 | Wang et al. |
| 2011/0123523 A1 | 5/2011 | Schoeberl et al. |
| 2012/0003160 A1 | 1/2012 | Wolf et al. |
| 2012/0034295 A1 | 2/2012 | Spiegel et al. |
| 2012/0045524 A1 | 2/2012 | Wernet et al. |
| 2012/0269812 A1 | 10/2012 | Baum et al. |
| 2012/0282325 A1 | 11/2012 | Tong et al. |
| 2013/0209481 A1 | 8/2013 | Zhou et al. |
| 2013/0236459 A1 | 9/2013 | Baum et al. |
| 2013/0274281 A1 | 10/2013 | Bradley |
| 2014/0065204 A1 | 3/2014 | Hayes et al. |
| 2014/0170075 A1 | 6/2014 | Drummond et al. |
| 2015/0182460 A1 | 7/2015 | Hong et al. |
| 2015/0182521 A1 | 7/2015 | Bayever et al. |
| 2015/0328156 A1 | 11/2015 | Bayever et al. |
| 2015/0374682 A1 | 12/2015 | Bayever et al. |
| 2016/0030341 A1 | 2/2016 | Hong et al. |
| 2016/0030342 A1 | 2/2016 | Hong et al. |
| 2016/0058704 A1 | 3/2016 | Tardi et al. |
| 2016/0074382 A1 | 3/2016 | Bayever et al. |
| 2016/0206615 A1 | 7/2016 | Tangutoori et al. |
| 2016/0303264 A1 | 10/2016 | Hendricks et al. |
| 2016/0346272 A1 | 12/2016 | Bayever et al. |
| 2017/0049767 A1 | 2/2017 | Blanchette et al. |
| 2017/0049775 A1 | 2/2017 | Bayever et al. |
| 2017/0202840 A1 | 7/2017 | Bayever et al. |
| 2017/0333421 A1 | 11/2017 | Adiwijaya et al. |

FOREIGN PATENT DOCUMENTS

| | | |
|---|---|---|
| CN | 101878229 A | 11/2010 |
| CN | 1980637 B | 2/2014 |
| WO | 1997028156 A1 | 8/1997 |
| WO | 2000023052 A1 | 4/2000 |
| WO | 2003013536 A2 | 2/2003 |
| WO | 2003030864 A1 | 4/2003 |
| WO | 2003101474 A1 | 12/2003 |
| WO | 2004017940 A3 | 4/2004 |
| WO | 2004093795 A3 | 11/2004 |
| WO | 2005000900 A1 | 1/2005 |
| WO | 2005107712 A1 | 11/2005 |
| WO | 2006110816 A2 | 10/2006 |
| WO | 2007076117 A2 | 7/2007 |
| WO | 2009040426 A1 | 4/2009 |
| WO | 2009126920 A3 | 3/2010 |
| WO | 2010125462 A2 | 11/2010 |
| WO | 2011066684 A1 | 6/2011 |
| WO | 2011153010 A1 | 12/2011 |
| WO | 2012012454 A1 | 1/2012 |
| WO | 2012031293 A1 | 3/2012 |
| WO | 2012078695 A2 | 6/2012 |
| WO | 2012079582 A1 | 6/2012 |
| WO | 2012146610 A1 | 11/2012 |
| WO | 2013006547 A2 | 1/2013 |
| WO | 2013138371 A1 | 9/2013 |
| WO | 2013158803 A1 | 10/2013 |
| WO | 2013188586 A1 | 12/2013 |
| WO | 2014113167 A1 | 7/2014 |
| WO | 2014157444 A1 | 10/2014 |
| WO | 2016094402 A1 | 6/2016 |
| WO | 2016168451 A1 | 10/2016 |
| WO | 2017031442 A1 | 2/2017 |
| WO | 2017031445 A1 | 2/2017 |
| WO | 2017034957 A1 | 3/2017 |
| WO | 2017066726 A1 | 4/2017 |
| WO | 2017172678 A1 | 10/2017 |
| WO | 2017199093 A1 | 11/2017 |
| WO | 2018083470 A1 | 5/2018 |

OTHER PUBLICATIONS

Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015).

Waterhouse D, et al., "Lipid-Based Nanoformulation of Irinotecan: Dual Mechanism of Action Allows for Combination Chemo/Angiogenic Therapy," Nanomedicine 6(9):1645-54 (2011).

Wilson W, et al., "Targeting Hypoxia in Cancer Therapy," Nat Rev Cancer. 11(6):393-410 (2011).

Yeh B, et al., "Structural Basis for Activation of Fibroblast Growth Factor Signaling by Sucrose Octasulfate," Mol Cell Biol. 22(20):7184-92 (2002).

Yi S, et al, "Irinotecan Monotherapy as Second-Line Treatment in Advanced Pancreatic Cancer," Cancer Chemother Pharmacol. 63(6):1141-5 (2009), Epub Oct. 7, 2008.

Yoo C, et al., "A Randomised Phase II Study of Modified FOLFIRI.3 vs Modified Folfox as Second-Line Therapy in Patients with Gemcitabine-Refractory Advanced Pancreatic Cancer," Br J Cancer 101(10):1658-63 (2009).

Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012).

Abraxane package insert, revision Dec. 23, 2011, retrieved from https://www.accessdata.fda.gov/drugsatfda_docs/label/2011/021660s025s026s029lbl.pdf, 13 pages.

Abraxane package insert, revision Jul. 21, 2015, retrieved from https://www.accessdata.fda.gov/drugsalfda_docs/label/2015/021660s041lbl.pdf, 24 pages.

(56) References Cited

OTHER PUBLICATIONS

Ahmad I, et al., "Antibody-Targeted Delivery of Doxorubicin Entrapped in Sterically Stabilized Liposomes Can Eradicate Lung Cancer in Mice," Cancer Res. 53(7):1484-8 (1993).

Author Unknown, "From Antinutrient to Phytonutrient: Phytic Acid Gains Respect" HighBeam Research, Environmental Nutrition, Apr. 1, 2004, 2 printed pages. URL: http://www.highbeam.com/doc/1G1-116341390.html/print (accessed Nov. 4, 2011).

Baker J, et al., "Irinophore C, a Novel Nanoformulation of Irinotecan, Alters Tumor Vascular Function and Enhances the Distribution of 5-Fluorouracil and Doxorubicin," Clin Cancer Res. 14(22):7260-71 (2008).

Brixi-Benmansour H, et al., "Phase II Study of First-line FOLFIRI for Progressive Metastatic Well-differentiated Pancreatic Endocrine Carcinoma," Dig Liver Dis. 43(11):912-6 (2011).

Camptosar package insert, revision Dec. 19, 2014, retrieved from https://www.accessdata.fda.gov/drugsatfda_docs/label/2014/020571s048lbl_pdf, 40 printed pages.

Camptosar package insert, revision May 14, 2010, retrieved from https://www.accessdata.fda.gov/drugsatfda_docs/label/2010/020571s0315032s0335036s037lbl.pdf, 37 pages.

CAS Registry Record for 23214-92-8 (doxorubicin), entered STN Nov. 16, 1984, 2 pages.

CAS Registry Record for 97682-44-5 (irinotecan), entered STN Aug. 18, 1985, 1 page.

Chen L, et al., "Expanded Analyses of NAPOLI-1: Phase 3 Study of MM-398 (nal-IRI), With or Without 5-Fluorouracil and Leucovorin, Versus 5-Fluorouracil and Leucovorin, in Metastatic Pancreatic Cancer (mPAC) Previously Treated with Gemcitabine-Based Therapy." Poster presented at the ASCO meeting of May 29-Jun. 2, 2015, Chicago, Illinois, 7 pages.

Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 1 page.

Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 1 page.

Chou T, et al., "Effect of Composition on the Stability of Liposomal Irinotecan Prepared by a pH Gradient Method," J Biosci Bioeng. 95(4):405-8 (2003).

Clinical Trials Identifier NCT00813163: Mar. 1, 2012 version, "A Phase II Study of PEP02 as a Second Line Therapy for Patients With Metastatic Pancreatic Cancer." Retrieved from ClinicalTrials.gov archive, 3 printed pages.

Clinical Trials Identifier NCT01375816: Jun. 16, 2011 version, "A Randomized Phase II Study of PEP02 or Irinotecan in Combination With Leucovorin and 5-Flourouracil in Second Line Therapy of Metastatic Colorectal Cancer." Retrieved from ClinicalTrials.gov archive, 5 printed pages.

Clinical Trials Identifier NCT01494506: Dec. 16, 2011 version, "A Randomized, Open Label Phase 3 Study of MM-398 versus 5-Fluorouracil and Leucovorin in Patients With Metastatic Pancreatic Cancer." Retrieved from ClinicalTrials.gov archive, 3 printed pages.

Clinical Trials Identifier NCT01494506: Aug. 9, 2012 version, "A Randomized, Open Label Phase 3 Study of MM-398, With or Without 5-Fluorouracil and Leucovorin, Versus 5-Fluorouracil and Leucovorin in Patients With Metastatic Pancreatic Cancer Who Have Failed Prior Gemcitabine-based Therapy." Retrieved from ClinicalTrials.gov archive, 3 printed pages.

Dawidczyk C, et al., "State-of-the-art in Design Rules for Drug Delivery Platforms: Lessons Learned from FDA-Approved Nanomedicines," J Control Release. 187:133-44 (2014).

Doxil package insert, revision Apr. 16, 2015, retrieved from https://www.accessdata.fda.gov/drugsatfda_docs/label/2015/050718s048lbl.pdf, 28 pages.

Doxil package insert, revision Jun. 10, 2008, retrieved from https://www.accessdata.fda.gov/drugsatfda_docs/label/2008/050718s033lbl.pdf, 34 pages.

Drummond D, et al., "Development of a Highly Active Nanoliposomal Irinotecan Using a Novel Intraliposomal Stabilization Strategy," Cancer Res. 66(6):3271-77 (2006).

Eisenhauer E, et al., "New Response Evaluation Criteria in Solid Tumours: Revised RECIST Guideline (version 1.1)," Eur J Cancer. 45(2):228-47 (2009).

Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33 (5):461-64 (2010).

Gemzar package insert, revision Feb. 4, 2011, retrieved from https://www.accessdata.fda.gov/drugsatfda_docs/label/2011/020509s069lbl.pdf, 21 pages.

Gemzar package insert, revision May 8, 2014, retrieved from https://www.accessdata.fda.gov/drugsatfda_docs/label/2014/020509s077lbl.pdf, 18 pages.

Grant S, et al., "Dose-Ranging Evaluation of the Substituted Benzamide Dazopride When Used as an Antiemetic in Patients Receiving Anticancer Chemotherapy," Cancer Chemother Pharmacol. 31(6):442-44 (1993).

Hong K, et al., "Anti-HER2 Immunoliposomes for Targeted Drug Delivery," Ann N Y Acad Sci. 886:293-6 (1999).

Hoskins J, et al., "UGT1A1*28 Genotype and Irinotecan-Induced Neutropenia: Dose Matters," J Natl Cancer Inst. 99 (17):1290-95 (2007).

Infante J, et al., "Phase I and Pharmacokinetic Study of IHL-305 (PEGylated Liposomal Irinotecan) in Patients with Advanced Solid Tumors," Cancer Chemother Pharmacol. 70(5):699-705 (2012).

Katsu T, et al., "Ion-Selective Electrode for Transmembrane pH Difference Measurements," Anal. Chem. 73(8):1849-54 (2001).

Kim J, et al., "Sustained Intratumoral Activation of MM-398 Results in Superior Activity over Irinotecan Demonstrated by Using a Systems Pharmacology Approach." Poster presented at the AACR Pancreatic Cancer Symposium, Jun. 18-21, 2012, New York, New York, 8 pages.

Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013).

Ko A, et al., "A Multinational Phase II Study of PEP02 (Liposome Irinotecan) for Patients with Gemcitabine-Refractory Metastatic Pancreatic Cancer," J Clin Oncol. 29:2011 (Suppl; Abstract 4069). 2011 ASCO Annual Meeting (2011), 2 printed pages.

Kozuch P, et al., "Irinotecan Combined with Gemcitabine, 5-Fluorouracil, Leucovorin, and Cisplatin (G-FLIP) is an Effective and Noncrossresistant Treatment for Chemotherapy Refractory Metastatic Pancreatic Cancer," Oncologist. 6(6):488-95 (2001).

Lee C, et al. "Novel Chondroitin Sulfate-binding Cationic Liposomes Loaded with Cisplatin Efficiently Suppress the Local Growth and Liver Metastasis of Tumor Cells in Vivo," Cancer Res. 62(15):4282-8 (2002).

Maddison J, et al., "Sucralfate," in Small Animal Clinical Pharmacology at p. 474, published by W. B. Saunders (2002).

Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011).

Miles D, et al., "Combination Versus Sequential Single-Agent Therapy in Metastatic Breast Cancer," Oncologist. 7 (suppl 6):13-19 (2002).

Münstedt K, et al., "Role of Dexamethasone Dosage in Combination with 5-HT3 Antagonists for Prophylaxis of Acute Chemotherapy-Induced Nausea and Vomiting," Br J Cancer. 79(3-4):637-9 (1999).

Nentwich, F., "Doxorubicin Hydrochloride," In Intravenous Therapy: A Comprehensive Application of Intravenous Therapy and Medication Administration at p. 310. Published by Jones & Bartlett Learning, 1990.

Neuzillet C., et al., "FOLFIRI Regimen as Second-/Third-line Chemotherapy in Patients with Advanced Pancreatic Adenocarcinoma Refradory to Gemcitabine and Platinum Salts: A Retrospective

(56) References Cited

OTHER PUBLICATIONS

Series of 70 Patients." J Clin Oncol. 29: 2011 (Suppl 4; Abstract 272). 2011 Gastrointestinal Cancers Symposium (2011), 2 printed pages.
Onivyde [MM-398] package insert, revision Oct. 22, 2015, retrieved from http://www.accessdata.fda.gov/drugsatfda_docs/label/2015/207793lbl.pdf, 18 pages.
PCT/US2013/045495: International Preliminary Report on Patentability dated Dec. 16, 2014, 8 pages.
PCT/US2013/045495: International Search Report and Written Opinion dated Aug. 22, 2013, 11 pages.
Rahma O, et al., "Second-Line Treatment in Advanced Pancreatic Cancer: A Comprehensive Analysis of Published Clinical Trials," Ann Oncol. 24(8):1972-9 (2013), epub doi:10.1093/annonc/mdt166, May 12, 2013, pp. 1-8.
Sadzuka Y, et al. "Effect of Liposomalization on the Antitumor Activity, Side-Effects and Tissue Distribution of CPT-11," Cancer Lett. 127(1-2): 99-106 (1998).
Shimada S, et al., "Irinotecan Plus Low-Dose Cisplatin for a-Fetoprotein-Producing Gastric Carcinoma with Multiple Liver Metastases: Report of Two Cases," Surg Today. 32(12):1075-80 (2002).
Taïeb J., "FOLFIRI.3, A New Regimen Combining 5-Fluorouracil, Folinic Acid and Irinotecan, for Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec. 8, 2006.
Tsai C, et al., "Nanovector-Based Therapies in Advanced Pancreatic Cancer," J Gastroint Oncol 2(3):185-94 (2011).
EP2861210: Response to EP Opposition Proceedings filed Aug. 24, 2018, D20 (MHRA Public Assessment Report for 5-Fluorouracil, 2006, 60 pages).
FDA News Release, "FDA Approves New Treatment for Advanced Pancreatic Cancer." Retrieved from http://ww.fda.gov/NewsEvents/Newsroom/PressAnnouncements/ucm468654.htm, Oct. 22, 2015, 3 printed pages.
Kambe M, et al., "Phase I Study of Irinotecan by 24-h Intravenous Infusion in Combination with 5-Fluorouracil in Metastatic Colorectal Cancer," Int J Clin Oncol. 17(2):150-4 (2012).
Ko A, et al., "A Multinational Phase II Study of PEPO2 (MM-398), Liposome Irinotecan, for Patients with Gemcitabine-refractory Metastatic Pancreatic Cancer." Poster presented at the American Society of Clinical Oncology meeting, Jun. 3-Jun. 7, 2011, Chicago, Illinois, 9 pages.
Köhne C, et al., "Randomized Phase III Study of High-Dose Fluorouracil Given as a Weekly 24-Hour Infusion With or Nithout Leucovorin Versus Bolus Fluorouracil Plus Leucovorin in Advanced Colorectal Cancer: European Organization of Research and Treatment of Cancer Gastrointestinal Group Study 40952," J Clin Oncol. 21(20):3721-8 (2003).
Merrimack, "Merrimack Announces Inclusion of ONIVYDE (irinotecan liposome injection) as a Category 1 Treatment Option in the 2016 NCCN Guidelines for Pancreatic Adenocarcinoma," Mar. 24, 2016. Retrieved from http://investors.merrimack.com/news-releases/news-release-details/merrimack-announces-inclusion-onivyder-irinotecan-liposome, 2 printed pages.
Minami H, et al., "Irinotecan Pharmacokinetics/Pharmacodynamics and UGT1A Genetic Polymorphisms in Japanese: Roles of UGT1A1*6 and *28," Pharmacogenet Genomics. 17(7):497-504 (2007).
Morgan R, et al., "Human Cell Line (COLO 357) of Metastatic Pancreatic Adenocarcinoma," Int J Cancer 25(5):591-8 (1980).
National Comprehensive Cancer Network Clinical Practice Guidelines in Oncology (NCCN Guidelines). "Pancreatic Adenocarcinoma." Version I.2016. Mar. 22, 2016 (PANG-9), 133 pages.
NIH National Cancer Institute, "FDA Approves Irinotecan Liposome to Treat Pancreatic Cancer," Nov. 24, 2015 by NCI Staff, 2 printed pages.
D'Dwyer P, et al., "Uridine Diphosphate Glucuronosyltransferase (UGT) 1A1 and Irinotecan: Practical Pharmacogenomics Arrives in Cancer Therapy," J Clin Oncol. 24(28):4534-8 (2006).

Palomaki G, et al., "Can UGT1A1 Genotyping Reduce Morbidity and Mortality in Patients with Metastatic Colorectal cancer Treated with Irinotecan? an Evidence-Based Review," Genet Med. 11(1)21-34 (2009).
Pliarchopoulou K, et al., "Pancreatic Cancer: Current and Future Treatment Strategies," Cancer Treat Rev. 35(5):431-6 (2009).
Rivory L, et al., "Pharmacokinetic Interrelationships of Irinotecan (CPT-11) and Its Three Major Plasma Metabolites in Patients Enrolled in Phase I/II Trials," Clin Cancer Res. 3(8):1261-6 (1997).
Rothenberg M, et al., "Phase I and Pharmacokinetic Trial of Weekly CPT-11," J Clin Oncol. 11(11):2194-204 (1993).
Saltz L, et al., "Irinotecan Plus Fluorouracil and Leucovorin for Metastatic Colorectal Cancer. Irinotecan Study Group," N Engl J Med. 343(13):905-14 (2000).
U.S. Appl. No. 11/121,294, dated Aug. 17, 2009 Nonfinal Office Action, 33 pages.
U.S. Appl. No. 11/121,294, dated Mar. 12, 2010 Final Office Action, 15 pages.
U.S. Appl. No. 11/121,294, dated May 19, 2010 Advisory Action, 3 pages.
U.S. Appl. No. 11/121,294, dated Aug. 4, 2010 Nonfinal Office Action, 14 pages.
U.S. Appl. No. 11/121,294, dated Dec. 6, 2010 Final Office Action, 17 pages.
U.S. Appl. No. 11/121,294, dated Apr. 13, 2011 Nonfinal Office Action, 10 pages.
U.S. Appl. No. 11/121,294, dated Jul. 12, 2011 Examiner Interview Summary, 3 pages.
U.S. Appl. No. 11/121,294, dated Nov. 23, 2011 Final Office Action, 20 pages.
U.S. Appl. No. 11/601,451, dated Jan. 11, 2010 Nonfinal Office Action, 14 pages.
U.S. Appl. No. 11/601,451, dated Aug. 27, 2010 Final Office Action, 17 pages.
U.S. Appl. No. 11/601,451, dated Jul. 12, 2011 Examiner Interview Summary, 4 pages.
U.S. Appl. No. 13/416,204, dated May 8, 2012 Pre-Interview Communication, 4 pages.
U.S. Appl. No. 13/416,204, dated Jun. 29, 2012 Interview Summary and First Action Interview Office Action, 6 pages.
U.S. Appl. No. 13/654,373, dated Aug. 12, 2013 Nonfinal Office Action and Interview Summary, 10 pages.
U.S. Appl. No. 14/151,632, dated Apr. 18, 2016 Nonfinal Office Action, 9 pages.
U.S. Appl. No. 14/175,365, dated Jun. 26, 2014 Nonfinal Office Action, 20 pages.
U.S. Appl. No. 14/406,776, dated Feb. 26, 2016 Nonfinal Office Action, 9 pages.
U.S. Appl. No. 14/632,422, dated Jan. 10, 2017 Nonfinal Office Action, 18 pages.
U.S. Appl. No. 14/812,950, dated Oct. 2, 2015 Pre-Interview Communication, 3 pages.
U.S. Appl. No. 14/844,500, dated Dec. 16, 2015 Nonfinal Office Action, 25 pages.
U.S. Appl. No. 14/851,111, dated Feb. 25, 2016 Nonfinal Office Action, 13 pages.
U.S. Appl. No. 14/879,302, dated Aug. 15, 2016 Nonfinal Office Action, 30 pages.
U.S. Appl. No. 14/879,302, dated Dec. 15, 2016 Nonfinal Office Action, 14 pages.
U.S. Appl. No. 14/879,358, dated Dec. 28, 2015 Nonfinal Office Action, 20 pages.
U.S. Appl. No. 14/879,358, dated Jul. 12, 2016 Nonfinal Office Action, 14 pages.
U.S. Appl. No. 14/964,239, dated Nov. 4, 2016 Nonfinal Office Action, 21 pages.
U.S. Appl. No. 14/964,239, dated Apr. 26, 2017 Examiner Interview Summary, 2 pages.
U.S. Appl. No. 14/964,239, dated Jun. 21, 2017 Nonfinal Office Action, 16 pages.
U.S. Appl. No. 14/964,239, dated Dec. 11, 2017 Nonfinal Office Action, 15 pages.

(56) References Cited

OTHER PUBLICATIONS

U.S. Appl. No. 14/964,571, dated Feb. 13, 2017 Nonfinal Office Action, 8 pages.
U.S. Appl. No. 14/964,571, dated Nov. 1, 2017 Final Office Action, 14 pages.
U.S. Appl. No. 14/964,571, dated Sep. 25, 2018 Nonfinal Office Action, 12 pages.
U.S. Appl. No. 14/965,140, dated Mar. 10, 2016 Nonfinal Office Action, 24 pages.
U.S. Appl. No. 11/121,294, filed May 2, 2005, U.S. Pat. No. 8,147,867, Issued, Shomer, Isaac.
U.S. Appl. No. 11/601,451, filed Nov. 17, 2006, U.S. Pat. No. 8,658,203, Issued, Kishmore, Gollamudi S.
U.S. Appl. No. 13/416,204, filed Mar. 9, 2012, U.S. Pat. No. 8,329,213, Issued, Shomer, Isaac.
U.S. Appl. No. 13/654,373, filed Oct. 17, 2012, U.S. Pat. No. 8,703,181, Issued, Shomer, Isaac.
U.S. Appl. No. 14/151,632, filed Jan. 9, 2014, Abandoned, Kishmore, Gollamudi S.
U.S. Appl. No. 14/175,365, filed Feb. 7, 2014, U.S. Pat. No. 8,992,970, Issued, Shomer, Isaac.
U.S. Appl. No. 14/632,422, filed Feb. 26, 2015, U.S. Pat. No. 9,717,723, Issued, Shomer, Isaac.
U.S. Appl. No. 14/879,302, filed Oct. 9, 2015, U.S. Pat. No. 9,730,891, Issued, Shomer, Isaac.
U.S. Appl. No. 14/879,358, filed Oct. 9, 2015, Abandoned, Shomer, Isaac.
U.S. Appl. No. 14/964,239, filed Dec. 9, 2015, Abandoned, Shomer, Isaac.
U.S. Appl. No. 14/965,140, filed Dec. 10, 2015, U.S. Pat. No. 9,724,303, Issued, Shomer, Isaac.
U.S. Appl. No. 14/966,458, filed Dec. 11, 2015, U.S. Pat. No. 9,782,349, Issued, Shomer, Isaac.
U.S. Appl. No. 14/979,666, filed Dec. 28, 2015, Abandoned, Shomer, Isaac.
U.S. Appl. No. 15/227,561, filed Aug. 3, 2016, Published, Shomer, Isaac.
U.S. Appl. No. 15/227,631, filed Aug. 3, 2016, Published, Shomer, Isaac.
U.S. Appl. No. 15/213,127, filed Jul. 18, 2016, Abandoned.
U.S. Appl. No. 15/296,536, filed Oct. 18, 2016, U.S. Pat. No. 9,737,528, Issued, Kishmore, Gollamudi S.
U.S. Appl. No. 15/363,761, filed Nov. 29, 2016, Published, Roney, Celeste A.
U.S. Appl. No. 15/363,923, filed Nov. 29, 2016, Abandoned, Roney, Celeste A.
U.S. Appl. No. 15/363,978, filed Nov. 29, 2016, Published, Roney, Celeste A.
U.S. Appl. No. 15/364,021, filed Nov. 29, 2016, Abandoned, Liu, Tracy.
U.S. Appl. No. 15/664,976, filed Jul. 31, 2017, Published, Shomer, Isaac.
U.S. Appl. No. 15/896,389, filed Feb. 14, 2018, Published, Shomer, Isaac.
U.S. Appl. No. 15/896,436, filed Feb. 14, 2018, Published, Shomer, Isaac.
U.S. Appl. No. 14/406,776, filed Dec. 10, 2014, U.S. Pat. No. 9,452,162, Issued, Strong, Tori.
U.S. Appl. No. 14/812,950, filed Jul. 29, 2015, U.S. Pat. No. 9,339,497, Issued, Strong, Tori.
U.S. Appl. No. 14/844,500, filed Sep. 3, 2015, U.S. Pat. No. 9,364,473, Issued, Strong, Tori.
U.S. Appl. No. 14/851,111, filed Sep. 11, 2015, U.S. Pat. No. 9,492,442, Issued, Strong, Tori.
U.S. Appl. No. 15/059,640, filed Mar. 3, 2016, Abandoned, Strong, Tori.
U.S. Appl. No. 15/241,128, filed Aug. 19, 2016, U.S. Pat. No. 9,717,724, Issued, Strong, Tori.
U.S. Appl. No. 15/341,377, filed Nov. 2, 2016, Abandoned, Strong, Tori.
U.S. Appl. No. 15/341,619, filed Nov. 2, 2016, Abandoned, Strong, Tori.
U.S. Appl. No. 15/652,513, filed Jul. 18, 2017, Abandoned, Strong, Tori.
U.S. Appl. No. 15/664,930, filed Jul. 31, 2017, Abandoned, Strong, Tori.
U.S. Appl. No. 16/012,372, filed Jun. 19, 2018, Pending, TBD.
U.S. Appl. No. 14/964,571, filed Dec. 9, 2015, Published, Baek, Bong-Sook.
U.S. Appl. No. 15/375,039, filed Dec. 9, 2016, Abandoned, Baek, Bong-Sook.
U.S. Appl. No. 15/928,649, filed Mar. 22, 2018, Abandoned.
U.S. Appl. No. 16/036,885, dated Jul. 16, 2018, Pending, TBD.
U.S. Appl. No. 15/337,274, filed Oct. 28, 2016, U.S. Pat. No. 9,895,365, Issued, Packard, Benjamin J.
U.S. Appl. No. 15/852,551, filed Dec. 22, 2017, Published, Packard, Benjamin J.
U.S. Appl. No. 15/241,106, filed Aug. 19, 2016, Abandoned, Roney, Celeste A.
U.S. Appl. No. 15/809,815, filed Nov. 10, 2017, Published, Roney, Celeste A.
U.S. Appl. No. 15/403,441, filed Jan. 11, 2017, Abandoned, Packard, Benjamin J.
U.S. Appl. No. 15/331,648, filed Oct. 21, 2016, Abandoned, Shomer, Isaac.
U.S. Appl. No. 15/331,393, filed Oct. 21, 2016, Abandoned, Shomer, Isaac.
U.S. Appl. No. 15/331,318, filed Oct. 21, 2016, Abandoned, Shomer, Isaac.
U.S. Appl. No. 15/645,645, filed Jul. 10, 2017, Abandoned, Shomer, Isaac.
U.S. Appl. No. 15/655,592, filed Jul. 20, 2017, Abandoned.
U.S. Appl. No. 15/661,868, filed Jul. 27, 2017, Abandoned, Shomer, Isaac.
U.S. Appl. No. 15/908,443, filed Feb. 28, 2018, Abandoned.
U.S. Appl. No. 15/768,352, filed Apr. 13, 2018, Published, TBD.
U.S. Appl. No. 15/967,633, filed May 1, 2018, Pending, TBD.
U.S. Appl. No. 15/967,638, filed May 1, 2018, Pending, Shomer, Isaac.
U.S. Appl. No. 15/598,633, filed May 18, 2017, Abandoned, Ricci, Craig D.
U.S. Appl. No. 15/948,571, filed Apr. 9, 2018, Abandoned.
American Chemical Society (ACS), http://www.cancer.org/cancer/pancreaticcancer/detailedguide/pancreatic-cancer-what-is-pancreatic-cancer, retrieved Dec. 10, 2017, 7 printed pages.
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancreatic Cancer (mPAC) Previously Treated with Gemcitabine-based Therapy." Poster presented at the Gastrointestinal Cancers Symposium of the ASCO meeting of Jan. 21-23, 2016, San Francisco, California, 16 pages.
Chen L, et al., "Phase I Study of Liposome Encapsulated Irinotecan (PEP02) in Advanced Solid Tumor Patients," Poster presented at the ASCO meeting of May 30-Jun. 3, 2008, Chicago, Illinois, 9 pages.
Clinical Trials Identifier NCT00813163: Jan. 12, 2015 version, "A Phase II Study of PEP02 as a Second Line Therapy for Patients with Metastatic Pancreatic Cancer." Retrieved from ClinicalTrials.gov archive, 3 printed pages.
Clinical Trials Identifier NCT00940758: Jul. 16, 2009 version, "Pharrnacokinetic Study of Biweekly PEP02 (Liposome rinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Feb. 3, 2010 version, "Phase I and Pharmacokinetic Study of Biweekly PEP02 (Liposome Irinotecan) in Patients With Metastatic Colorectal Cancer Refractory to First-line Oxaliplatin-based chemotherapy." Retrieved from ClinicalTrials.gov archive, 3 printed pages.
Clinical Trials Identifier NCT00940758: Mar. 1, 2012 version, "Phase I and Pharmacokinetic Study of Biweekly PEP02 in mCRC

(56) References Cited

OTHER PUBLICATIONS

Refractory to 1st-line Oxaliplatin Base Therapy." Retrieved from ClinicalTrials.gov archive, 3 printed pages.

Clinical Trials Identifier NCT01359007: May 23, 2011 version, "A Phase II Study Evaluating the Rate of R0 Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer." Retrieved from ClinicalTrials.gov archive, 3 printed pages.

Clinical Trials Identifier NCT01359007: May 28, 2015 version, "A Phase II Study Evaluating the Rate of R0 Resection (Microscopically Negative Margins) After Induction Therapy With 5-Fluorouracil, Leucovorin, Oxaliplatln, Irinotecan (FOLFIRINOX) in Patients With Borderline Resectable or Locally Advanced Inoperable Pancreatic Cancer." Retrieved from ClinicalTrials.gov archive, 3 printed pages.

Clinical Trials Identifier NCT01446458: Oct. 4, 2011 version, "Phase I Study of Stereotactic Body Radiation Therapy and 5-Fluorouracil, Oxaliplatin and Irinotecan (FOLFIRINOX) in the Neoadjuvant Therapy of Pancreatic Cancer." Retrieved from ClinicalTrials.gov archive, 5 printed pages.

Clinical Trials Identifier NCT01494506: Aug. 1, 2013 version, "A Randomized, Open Label Phase 3 Study of MM-398, Nith or Without S~Fluorouracil and Leucovorin, Versus 5 Fluorouracil and Leucovorin in Patients with Metastatic Pancreatic Cancer Who Have Failed Prior Gemcitabine-based Therapy." Retrieved from ClinicalTrials.gov archive, 3 printed pages.

Clinical Trials Identifier NCT01494506: Jun. 16, 2016 version, "A Randomized, Open Label Phase 3 Study of MM-398, Nith or Without 5-Fluorouracil and Leucovorin, Versus 5 Fluorouracil and Leucovorin in Patients with Metastatic Pancreatic Cancer Who Have Failed Prior Gemcitabine-based Therapy." Retrieved from ClinicalTrials.gov archive, 5 printed pages.

Clinical Trials Identifier NCT01523457: Jan. 31, 2012 version, "Phase II Study of Modified Folfirinox in Advanced Pancreatic Cancer." Retrieved from ClinicalTrials.gov archive, 4 printed pages.

Clinical Trials Identifier NCT01643499: Jul. 17, 2012 version, "A Genotype-guided Dosing Study of mFOLFIRINOX in Jreviously Untreated Patients with Advanced Gastrointestinal Malignancies." Retrieved from ClinicalTrials.gov archive, 5 printed pages.

Clinical Trials Identifier NCT01688336: Sep. 18, 2012 version, "Phase II Single Arm Clinical Trial of FOLFIRINOX for Unresectable Locally Advanced and Borderline Resectable Pancreatic Cancer." Retrieved from ClinicalTrials.gov archive, 5 printed pages.

Clinical Trials Identifier NCT01771146: Jan. 17, 2013 version, "A Prospective Evaluation of Neoadjuvant FOLFIRINOX Regimen in Patients with Non-metastatic Pancreas Cancer (Baylor University Medical Center and Texas Oncology Experience)." Retrieved from ClinicalTrials.gov archive, 3 printed pages.

Clinical Trials Identifier NCT01926197: Aug. 19, 2013 version, "A Randomized Phase III Study Evaluating Modified FOLFIRINOX (mFFX) With or Without Stereotactic Body Radiotherapy (SBRT) in the Treatment of Locally Advanced Pancreatic Cancer." Retrieved from ClinicalTrials.gov archive, 3 printed pages.

Clinical Trials Identifier NCT01992705: Nov. 22, 2013 version, "Neoadjuvant FOLFIRINOX and Stereotactic Body Radiotherapy (SBRT) Followed by Definitive Surgery for Patients with Borderline Resectable Pancreatic Adenocarcinoma: A Single-Arm Pilot Study." Retrieved from ClinicalTrials.gov archive, 5 printed pages.

Clinical Trials Identifier NCT02028806: Jan. 6, 2014 version, "Phase II Trial to Investigate the Efficacy and Safety of mFOLFIRINOX in Patients with Metastatic Pancreatic Cancer in China." Retrieved from ClinicalTrials.gov archive, 4 printed pages.

Clinical Trials Identifier NCT02047474: Jan. 27, 2014 version, "Phase II Study of Peri-Operative Modified Folfirinox in Localized Pancreatic Cancer." Retrieved from ClinicalTrials.gov archive, 5 printed pages.

Clinical Trials Identifier NCT02109341: Apr. 8, 2014 version, "Phase I/II Study to Evaluate Nab-paclitaxel in Substitution of CPT11 or Oxaliplatin in Folfirinox Schedule as First Line Treatment on Metastatic Pancreatic Cancer." Retrieved from ClinicalTrials.gov archive, 5 printed pages.

Clinical Trials Identifier NCT02143219: May 20, 2014 version, "Phase-2 Study Evaluating Overall Response Rate (Efficacy) and Autonomy Daily Living Preservation (Tolerance) of 'FOLFIRINOX' Pharmacogenic Dose Adjusted, in Elderly Patients (70 yo. or Older) With a Metastatic Pancreatic Adenocarcinoma." Retrieved from ClinicalTrials.gov archive, 5 printed pages.

Clinical Trials Identifier NCT02148549: May 27, 2014 version, "The Pilot Study of Neoadjuvant Chemotherapy of FIRINOX for Patients With Borderline Resectable Pancreatic Cancer" Retrieved from ClinicalTrials.gov archive, 4 Printed pages.

Clinical Trials Identifier NCT02884128: Aug. 25, 2016 version, "A Study of PEP02 in Combination With 5-fluorouracil (5-FU) and Leucovorin (LV) in Advanced Solid Tumors." Retrieved from ClinicalTrials.gov archive, 3 printed pages.

Clinical Trials Identifier NCT02896803: Sep. 11, 2016 version, "A Phase II Trial of Bolus Fluorouracil and Oxaliplatin (mFLOX) as First-line Regimen for Patients With Unresectable or Metastatic Pancreatic Cancer Not Eligible for Infusional Fluorouracil, Irinotecan and Oxaliplatin." Retrieved from ClinicalTrials.gov archive, 4 printed pages.

Clinical Trials Identifier NCT02896907: Sep. 11, 2016 version, "A Pilot Study of Intravenous Ascorbic Acid and Folfirinox in the Treatment of Advanced Pancreatic Cancer" Retrieved from ClinicalTrials.gov archive, 4 printed pages.

Conroy T, et al., "FOLFIRINOX versus Gemcitabine for Metastatic Pancreatic Cancer," N Engl J Med. 364(19):1817-25 (2011).

Douillard J, et al.,"Irinotecan Combined with Fluorouracil Compared with Fluorouracil Alone as First-line Treatment for Metastatic Colorectal Cancer: A Multicentre Randomised Trial," Lancet. 355(9209):1041-7 (2000).

EP2861210: Communication of Notices of Opposition (R. 79(1) EPC), dated Feb. 16, 2018, 1 page.

EP2861210: Notice of Opposition dated Feb. 5, 2018, 6 pages.

EP2861210: Opposition dated Feb. 5, 2018, Annex to Notice of Opposition, Facts and Arguments, 8 pages.

EP2861210: Opposition dated Feb. 5, 2018, D1 (FUSILEV package insert, 2008, 7 pages).

EP2861210: Opposition dated Feb. 5, 2018, D2 (Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010)).

EP2861210: Opposition dated Feb. 5, 2018, D3 (Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012)).

EP2861210: Opposition dated Feb. 5, 2018, D4 (Neuzillet C, et al., "FOLFIRI Regimen in Metastatic Pancreatic Adenocarcinoma Resistant to Gemcitabine and Platinum-Salts," World J Gastroenterol. 18(33):4533-41 (2012)).

EP2861210: Opposition dated Feb. 5, 2018, D5 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009)).

EP2861210: Opposition dated Feb. 5, 2018, D6 (Taleb J., "FOLFIRI. 3, A New Regimen Combining 5-Fluorouracil, Folinic Acid and Irinotecan, for Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec. 8, 2006).

EP2861210: Opposition dated Feb. 5, 2018, D7 (Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 2 pages).

EP2861210: Opposition dated Feb. 5, 2018, D8 (Infante J, et al., "Phase I and Pharmacokinetic Study of IHL-305 (PEGylated Liposomal Irinotecan) in Patients With Advanced Solid Tumors," Cancer Chemother Pharmacol. 70(5): 699-705 (2012)).

(56) References Cited

OTHER PUBLICATIONS

EP2861210: Opposition dated Feb. 5, 2018, D9 (Waterhouse D, et al., "Lipid-Based Nanoformulation of Irinotecan: Dual Mechanism of Action Allows for Combination Chemo/Angiogenic Therapy," Nanomedicine 6(9):1645-54 (2011)).
EP2861210: Opposition filed Feb. 5, 2018, D10 (CAMPTOSAR package insert, 2012, 39 pages).
EP2861210: Opposition filed Feb. 5, 2018, D11 (Hoskins J, et al., "UGT1A1*28 Genotype and Irinotecan-Induced Neutropenia: Dose Matters," J Natl Cancer Inst. 99(17):1290-95 (2007)).
EP2861210: Opposition dated Feb. 5, 2018, D12 (Tsai C, et al., "Nanovector-Based Therapies in Advanced Pancreatic Cancer," J Gastroint Oncol 2(3):185-94 (2011)).
EP2861210: Opposition dated Feb. 5, 2018, D13 (Ko A, et al., "A Multinational Phase II Study of Liposome Irinotecan (PEP02) for Patients with Gemcitabine-Refractory Metastatic Pancreatic Cancer," J Clin Oncol. 29:2011 (Suppl; Abstract 237). 2011 ASCO Annual Meeting (2011), 2 printed pages).
EP2861210: Opposition dated Feb. 5, 2018, D15 (Clinical Trials Identifier NCT01494506: Jan. 25, 2013 version, "A Randomized, Open Label Phase 3 Study of MM-398, With or Without 5-Fluorouracil and Leucovorin, Versus 5=luorouracil and Leucovorin in Patients With Metastatic Pancreatic Cancer Who Have Failed Prior Gemcitabine-based Therapy," Retrieved from ClinicalTrials.gov archive, 1 printed page).
EP2861210: Response to EP Opposition Proceedings filed Aug. 24, 2018, 22 pages.
EP2861210: Response to EP Opposition Proceedings filed Aug. 24, 2018, D15a (Clinical Trials Identifier NCT01494506: Dec. 16, 2011 version, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages).
EP2861210: Response to EP Opposition Proceedings filed Aug. 24, 2018, D17 (European Commission Implementing Decision granting marketing authorisation for Onivyde, Oct. 14, 2016), 39 pages.
EP2861210: Response to EP Opposition Proceedings filed Aug. 24, 2018, D18 (FDA News Release, "FDA Approves New Treatment for Advanced Pancreatic Cancer." Retrieved from http://ww.fda.gov/NewsEvents/Newsroom/PressAnnouncements/ucm468654.htm, Oct. 22, 2015, 3 printed pages).
EP2861210: Response to EP Opposition Proceedings filed Aug. 24, 2018, D19 (Wang-Gillam A, et al., "Nanoliposomal Irinotecan with Flourouracil and Folinic Acid in Metastatic Pancreatic Cancer After Previous emcitabine-Based Therapy (NAPOLI-1): A Global, Randomised, Open-Label, Phase 3 Trial," Lancet, 387 (10018):545-57 (2016). Epub doi: 10.1016/S0140-6736(15)00986-1, pp. 1-13 (2015)).
U.S. Appl. No. 14/965,140, dated Jul. 13, 2016 Interview Summary and Nonfinal Office Action, 14 pages.
U.S. Appl. No. 14/965,140, dated Dec. 19, 2016 Nonfinal Office Action, 9 pages.
U.S. Appl. No. 14/966,458, dated Dec. 6, 2016 Nonfinal Office Action, 34 pages.
U.S. Appl. No. 14/966,458, dated Apr. 27, 2017 Examiner Interview Summary, 2 pages.
U.S. Appl. No. 14/979,666, dated Dec. 9, 2016 Nonfinal Office Action, 20 pages.
U.S. Appl. No. 15/059,640, dated Dec. 2, 2016 Nonfinal Office Action, 9 pages.
U.S. Appl. No. 15/227,561, dated Jul. 14, 2017 Nonfinal Office Action, 25 pages.
U.S. Appl. No. 15/227,561, dated Apr. 26, 2018 Nonfinal Office Action, 13 pages.
U.S. Appl. No. 15/227,561, dated Dec. 10, 2018 Final Office Action, 18 pages.
U.S. Appl. No. 15/227,631, dated Jul. 17, 2017 Nonfinal Office Action, 24 pages.
U.S. Appl. No. 15/227,631, dated Apr. 10, 2018 Nonfinal Office Action, 13 pages.
U.S. Appl. No. 15/227,631, dated Aug. 31, 2018 Nonfinal Office Action, 15 pages.
U.S. Appl. No. 15/227,631, Dec. 19, 2018 Final Office Action, 15 pages.
U.S. Appl. No. 15/241,106, dated Oct. 28, 2016 Pre-Interview Communication, 4 pages.
U.S. Appl. No. 15/241,106, dated Dec. 29, 2016 Nonfinal Office Action, 15 pages.
U.S. Appl. No. 15/241,106, dated Jul. 10, 2017 Final Office Action, 16 pages.
U.S. Appl. No. 15/241,128, dated Nov. 25, 2016 Nonfinal Office Action, 6 pages.
U.S. Appl. No. 15/296,536, dated Mar. 8, 2017 Nonfinal Office Action, 6 pages.
U.S. Appl. No. 15/331,393, dated Jan. 19, 2017 Pre-Interview Communication, 4 pages.
U.S. Appl. No. 15/331,393, dated Mar. 20, 2017: Examiner's Interview Summary and First Action Interview Office Action Summary, 5 pages.
U.S. Appl. No. 15/331,648, dated Jan. 19, 2017 Pre-Interview Communication, 4 pages.
U.S. Appl. No. 15/331,648, dated Mar. 17, 2017 Examiner's Interview Summary, 3 pages.
U.S. Appl. No. 15/337,274, dated Mar. 24, 2017 Nonfinal Office Action, 10 pages.
U.S. Appl. No. 15/341,377, dated Jan. 30, 2017 Nonfinal Office Action, 12 pages.
U.S. Appl. No. 15/341,377, dated Apr. 18, 2017 Final Office Action, 13 pages.
U.S. Appl. No. 15/341,619, dated Apr. 3, 2017 Pre-Interview Communication, 3 pages.
U.S. Appl. No. 15/363,761, dated Jan. 18, 2017 Nonfinal Office Action, 15 pages.
U.S. Appl. No. 15/363,761, dated Aug. 1, 2017 Final Office Action, 18 pages.
U.S. Appl. No. 15/363,761, dated Dec. 14, 2017 Examiner Interview Summary, 3 pages.
U.S. Appl. No. 15/363,923, dated Feb. 1, 2017 Nonfinal Office Action, 24 pages.
U.S. Appl. No. 15/363,923, dated Sep. 13, 2017 Final Office Action, 29 pages.
U.S. Appl. No. 15/363,978, dated Feb. 7, 2017 Nonfinal Office Action, 16 pages.
U.S. Appl. No. 15/363,978, dated Aug. 21, 2017 Final Office Action, 19 pages.
U.S. Appl. No. 15/363,978, dated Dec. 14, 2017 Examiner Interview Summary, 3 pages.
U.S. Appl. No. 15/364,021, dated Mar. 9, 2017 Nonfinal Office Action, 18 pages.
U.S. Appl. No. 15/364,021, dated Oct. 4, 2017 Final Office Action, 20 pages.
U.S. Appl. No. 15/375,039, dated Feb. 16, 2018 Nonfinal Office Action, 11 pages.
U.S. Appl. No. 15/403,441, dated Dec. 21, 2017 Nonfinal Office Action, 9 pages.
U.S. Appl. No. 15/645,645, dated Dec. 1, 2017 Nonfinal Office Action, 16 pages.
U.S. Appl. No. 15/652,513, dated Dec. 20, 2017 Nonfinal Office Action, 13 pages.
U.S. Appl. No. 15/661,868, dated Dec. 1, 2017 Nonfinal Office Action, 15 pages.
U.S. Appl. No. 15/664,930, dated Dec. 20, 2017 Nonfinal Office Action, 7 pages.
U.S. Appl. No. 15/664,976, dated Sep. 11, 2018 Nonfinal Office Action, 23 pages.
U.S. Appl. No. 15/809,815, dated Mar. 6, 2018 Nonfinal Office Action, 12 pages.
U.S. Appl. No. 15/809,815, dated Sep. 11, 2018 Final Office Action, 14 pages.
U.S. Appl. No. 15/852,551, dated Jan. 11, 2019 Nonfinal Office Action, 5 pages.
U.S. Appl. No. 15/967,638, dated Jan. 14, 2019 Nonfinal Office Action, 14 pages.

(56) References Cited

OTHER PUBLICATIONS

Pelzer U, et al., "A Randomized Trial in Patients With Gemcitabine Refractory Pancreatic Cancer Final Results of the CONKO 003 Study," J Clin Oncol. 2008 ASCO Annual Meeting Proceedings. 26(15S):4508 (2008), 2 printed pages.
Pelzer U, et al., "Second-Line Therapy in Refractory Pancreatic Cancer. Results of a Phase II Study," Onkologie. 32 (3):99-102 (2009).
Petrioli R, et al., "Gemcitabine, Oxaliplatin, and Capecitabine (GEMOXEL) Compared with Gemcitabine Alone in Metastatic Pancreatic Cancer: A Randomized Phase II Study," Cancer Chemother Pharmacol. 75(4):683-90 (2015).
Qin B, et al., "In-vitro Schedule-Dependent Interaction Between Oxaliplatin and 5-Fluorouracil in Human Gastric Cancer Cell Lines," Anti-Cancer Drugs. 17(4):445-53 (2006).
Rahib L, et al., "Projecting Cancer Incidence and Deaths to 2030: The Unexpected Burden of Thyroid, Liver, and Pancreas Cancers in the United States," Cancer Res. 74(11):2913-21 (2014).
Reni M, et al., "Salvage Chemotherapy with Mitomycin, Docetaxel, and Irinotecan (MDI Regimen) in Metastatic Pancreatic Adenocarcinoma: A Phase I and II Trial," Cancer Invest. 22(5):688-96 (2004).
Rombouts S, et al., "FOLFIRINOX in Locally Advanced and Metastatic Pancreatic Cancer: A Single Centre Cohort Study," J Cancer 7(13):1861-6 (2016).
Siegel R, et al., "Cancer Statistics, 2015," CA Cancer J Clin. 65(1):5-29 (2015).
Stein S, et al., "Final Analysis of a Phase II Study of Modified FOLFIRINOX in Locally Advanced and Metastatic Pancreatic Cancer," Br J Cancer. 114(7):737-43 (2016).
Takahara N, et al., "Uridine Disphosphate Glucuronosyl Transferase 1 Family Polypeptide A1 Gene (UGT1A1) Polymorphisms are Associated with Toxicity and Efficacy in Irinotecan Monotherapy for Refractory Pancreatic Cancer," cancer Chemother Pharmacol. 71(1):85-92 (2013), Epub Sep. 29, 2012.
Tanaka R, et al., "Synergistic Interaction Between Oxaliplatin and SN-38 in Human Gastric Cancer Cell Lines In Vitro," Oncol Rep. 14(3):683-8 (2005).
Tsubamoto H, et al., "Combination Chemotherapy with Itraconazole for Treating Metastatic Pancreatic Cancer in the Second-line or Additional Setting,". Anticancer Res. 35(7):4191-6 (2015).
Ueno H, et al., "A Phase II Study of Weekly Irinotecan as First-Line Therapy for Patients with Metastatic Pancreatic Cancer," Cancer Chemother Pharmacol. 59(4):447-54 (2007), Epub Jul. 20, 2006.
Ulrich-Pur H, et al., "Irinotecan Plus Raltitrexed vs Raltitrexed Alone in Patients with Gemcitabine-Pretreated Advanced Pancreatic Adenocarcinoma," Br J Cancer 88(8):1180-4 (2003).
Umemura A, et al., "Modified FOLFIRINOX for Locally Advanced and Metastatic Pancreatic Cancer Patients Resistant to Gemcitabine and S-1 in Japan: A Single Institutional Experience," Hepato-Gastroenterology. 61:00-00 doi10.5754/hge14111, pp. 6-12 (2013).
Van Cutsem E, et al., "A Phase Ib Dose-Escalation Study of Erlotinib, Capecitabine and Oxaliplatin in Metastatic Colorectal Cancer Patients," Ann Oncol. 19(2):332-9 (2008), Epub Nov. 6, 2007.
Wagener D, et al., "Phase II Trial of CPT-11 in Patients with Advanced Pancreatic Cancer: An EORTC Early Clinical Trials Group Study," Ann Oncol. 6(2):129-32 (1995).
Wasserman E, et al., "Combination of Oxaliplatin Plus Irinotecan in Patients With Gastrointestinal Tumors: Results of Two Independent Phase I Studies with Pharmacokinetics," J Clin Oncol. 17(6):1751-9 (1999).
Ychou, M, et al., "An Open Phase I Study Assessing the Feasibility of the Triple Combination: Oxaliplatin Plus Irinotecan Plus Leucovorin/5-Fluorouracil Every 2 Weeks in Patients With Advanced Solid Tumors," Ann Oncol. 14 (3):481-9 (2003).
Zeghari-Squalli, N et al., "Cellular Pharmacology of the Combination of the DNA Topoisomerase I Inhibitor SN-38 and the Deaminocyclohexane Platinum Derivative Oxaliplatin," Clin Cancer Res. 5(5):1189-96 (1999).
Chuang V and M. Suno, "Levoleucovorin as Replacement for Leucovorin in Cancer Treatment," Ann Pharmacother. 46 (10):1349-57 (2012).
EP2861210: Summons to attend oral proceedings including preliminary opinion of the Opposition Division dated Jan. 30, 2019, 12 pages.
EP2861210: Opponent submission in opposition proceedings made following summons to attend oral proceedings, dated May 10, 2019, 20 pages.
EP2861210: Opponent submission in opposition proceedings made following summons to attend oral proceedings, dated May 10, 2019, D1b (Leucovorin calcium injection product label, Nov. 2011, 2 pages).
EP2861210: Opponent submission in opposition proceedings made following summons to attend oral proceedings, dated May 10, 2019, D22 (Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) May 20 Suppl):e13024 (2010), 1 page).
EP2861210: Proprietor's Auxiliary Requests in Opposition Proceedings filed Jun. 28, 2019, including cover letter and clean and marked-up AR1, AR2, and AR3, 12 pages.
EP2861210: Minutes of the oral proceedings before the Opposition Division, dated Aug. 28, 2019, 9 pages.
EP2861210: Opposition Division's decision to revoke patent, dated Aug. 28, 2019, 27 pages.
Slatter JG, et al., "Pharmacokinetics, Metabolism, and Excretion of Irinotecan (CPT-11) Following I.V. Infusion of [14C] CPT-11 in Cancer Patients," Drug Metab Dispos, 2000, 28(4):423-33.
U.S. Appl. No. 14/964,571, dated Jun. 12, 2019 Final Office Action, 15 pages.
U.S. Appl. No. 15/664,976, dated May 21, 2019 Nonfinal Office Action, 11 pages.
U.S. Appl. No. 15/768,352, dated Feb. 14, 2019 Non-Final Office Action, 15 pages.
U.S. Appl. No. 15/768,352, dated Jun. 3, 2019 Examiner Interview Summary, 4 pages.
U.S. Appl. No. 15/768,352, dated Jun. 12, 2019 Notice of Allowance including Examiner's Reasons for Allowance and Examiner Interview Summary, 21 pages.
U.S. Appl. No. 15/768,352, dated Aug. 28, 2019 Notice of Allowance including Examiner's Reasons for Allowance and Examiner Interview Summary, 16 pages.
U.S. Appl. No. 15/768,352, dated Jul. 12, 2019 Examiner Interview Summary, 4 pages.
U.S. Appl. No. 15/809,815, dated Jul. 8, 2019 Non-Final Office Action, 13 pages.
U.S. Appl. No. 15/896,389, Jul. 18, 2019 Nonfinal Office Action, 24 pages.
U.S. Appl. No. 15/896,436, dated Jul. 5, 2019 Nonfinal Office Action, 18 pages.
U.S. Appl. No. 16/012,351, dated Mar. 8, 2019 Non-Final Office Action, 13 pages.
U.S. Appl. No. 16/012,372, dated Mar. 8, 2019 Non-Final Office Action, 8 pages.
U.S. Appl. No. 16/036,885, dated Sep. 3, 2019 Non-Final Office Action, 15 pages.
Alberts S, et al. "Gemcitabine and Oxaliptatin for Metastatic Pancreatic Adenocarcinoma: A North Central Cancer Treatment Group Phase II Study," Ann Oncol. 14(4):580-5 (2003).
Assaf E, et al., "5-Fluorouracil/Leucovorin Combined with Irinotecan and Oxaliplatin (FOLFIRINOX) as Second-Line Chemotherapy in Patients with Metastatic Pancreatic Adenocarcinoma," Oncology. 80(5-6):301-6 (2011).
Azrak R, et al., "Therapeutic Synergy Between Irinotecan and 5-Fluorouracil against Human Tumor Xenografts," Clin Cancer Res. 10(3):1121-9 (2004).
Boeck S, et al., "Capecitabine Plus Oxaliplatin (CapOx) versus Capecitabine Plus Gemcitabine (CapGem) versus Gemcitabine Plus Oxaliplatin (mGemOx): Final Results of a Multicenter Randomized Phase II Trial in Advanced Pancreatic Cancer," Ann Oncol. 19(2):340-7 (2008), Epub Oct. 24, 2007.

(56) References Cited

OTHER PUBLICATIONS

Burris H, et al., "Phase II Trial of Oral Rubitecan in Previously Treated Pancreatic Cancer Patients," Oncologist. 10 (3):183-90 (2005).
Cantore M, et al., "Combined Irinotecan and Oxaliplatin in Patients with Advanced Pre-Treated Pancreatic Cancer," Oncology 67(2):93-7 (2004).
Cereda S, et al., "XELIRI or FOLFIRI as Salvage Therapy in Advanced Pancreatic Cancer," Anticancer Res. 30 (11):4785-90 (2010).
Chang T, et al., "Phase I Study of Nanoliposomal Irinotecan (PEP02) in Advanced Solid Tumor Patients," Cancer Chemother Pharmacol. 75(3):579-86 (2015).
Chibaudel B, et al., "PEPCOL: A Randomized Non-Comparative Phase II Study to Evaluate the Efficacy and Safety of PEP02 (MM-398) or Irinotecan in Combination with Leucovorin and 5-Fluorouracil as Second-Line Treatment for Patients with Unresectable Metastatic Colorectal Cancer a Gercor Study." Poster presented at ASCO 2015, 6 pages.
Chiesa M, et al., "A Pilot Phase II Study of Chemotherapy with Oxaliplatin, Folinic Acid, 5-Fluorouracil and Irinotecan in Metastatic Gastric Cancer," Tumori. 93(3):244-7 (2007).
Conroy T, et al., "Irinotecan Plus Oxaliplatin and Leucovorin-Modulated Fluorouracil in Advanced Pancreatic Cancer-A Groupe Tumeurs Digestives of the Fédération Nationale des Centres de Lutte Contre le Cancer Study," J Clin Oncol. 23(6):1228-36 (2005).
Dean A, et al., "A Phase 2, Open-Label Dose-Exploration Study of Liposomal Irinotecan (nal-IRI) Plus 5-Flurouracill Leucovorin (5-FU/LV) plus Oxaliplatin (OX) in Patients With Previously Untreated Metastatic Pancreatic Cancer." Poster presented at the American Society of Clinical Oncology Annual Conference, Chicago, IL, Jun. 1-5, 2018, 11 pages.
Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster presented at the Gastrointestinal Cancers Symposium ASCO 2016, 11 pages.
Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster handout at the Gastrointestinal Cancers Symposium ASCO 2016, 2 pages.
Delord J, et al., "Population Pharmacokinetics of Oxaliplatin," Cancer Chemother Pharmacol. 51(2):127-31 (2003), Epub Dec. 4, 2002.
Ducreux M, et al., "Randomized Phase II Study Evaluating Oxaliplatin Alone, Oxaliplatin Combined with Infusional 5-FU, and Infusional 5-FU Alone in Advanced Pancreatic Carcinoma Patients," Ann Oncol. 15(3): 467-73 (2004).
Eloxatin package insert, revision Dec. 28, 2011, retrieved from https://www.accessdata.fda.gov/drugsaffda_docs/label/2011/0214925012lbl_pdf, 51 pages.
Extra J, et al., "Phase I Study of Oxaliplatin in Patients with Advanced Cancer," Cancer Chemother Pharmacol. 25(4):299-303 (1990).
Fischel J, et al., "Ternary Combination of Irinotecan, Fluorouracil-Folinic Acid and Oxaliplatin: Results on Human Colon Cancer Cell Lines," Br J Cancer. 84(4):579-85 (2001).
Gaddy D, "Preclinical Anti-tumor Activity of Nanoliposomal Irinotecan (Nal-IRI, MM-398) + 5-FU + Oxaliplatin in Pancreatic Cancer." Abstract presented at AACR 2016, 1 page.
Gaddy D, et al., "Preclinical Anti-tumor Activity of Nanoliposomal Irinotecan (nal-IRI, MM-398) + 5-FU + Oxaliplatin in Pancreatic Cancer." Poster presented at AACR 2016, 5 pages.
GLOBOCAN Cancer Facts Sheets: All Cancers 2012. Available from: http://globocan.iarc.fr/old/FactSheets/cancers/all-new.asp, accessed on Oct. 3, 2016, 9 printed pages.
Goldstein D, et al., "nab-Paclitaxel Plus Gemcitabine for Metastatic Pancreatic Cancer: Long-Term Survival From a Phase III Trial," J Natl Cancer Inst. 107(2): dju413, pp. 1-10 (2015).

Guichard S, et al., "Combination of Oxaliplatin and Irinotecan on Human Colon Cancer Cell Lines: Activity In Vitro and In Vivo," Anticancer Drugs. 12(9):741-51 (2001).
Hosein P, et al., "A Retrospective Study of Neoadjuvant FOLFIRINOX in Unresectable or Borderline-Resectable Locally Advanced Adenocarcinoma," BMC Cancer. 12:199, pp. 1-7 (2012).
Jacobs A, et al., "A Randomized Phase III Study of Rubitecan (ORA) vs. Best Choice (BC) in 409 Patients with Refractory Pancreatic Cancer Report from a North-American Multi-Center Study," J Clin Oncol., 2004 ASCO Annual Meeting Proceedings 22(14S):4013 (2004).
Kalra A, et al., "Preclinical Activity of Nanoliposomal Irinotecan Is Governed by Tumor Deposition and Intratumor Pro-Drug Conversion," Cancer Res. Author Manuscript Published OnlineFirst Oct. 1, 2014, 31 pages.
Kalra A, et al., "Preclinical Activity of Nanoliposomal Irinolecan Is Governed by Tumor Deposition and Intratumor Prodrug Conversion," Cancer Res. 74(23):7003-13 (2014), published OnlineFirst, OF1-OF11, Oct. 1, 2014, 12 pages.
Kalra A, et al., "Preclinical Activity of Nanoliposomal Irinotecan Is Governed by Tumor Deposition and Intratumor Prodrug Conversion," Cancer Res. Author queries on manuscript, pp. 1-11 (2014), 13 total pages.
Klinz S, et al., "Identifying Differential Mechanisms of Action for MM-398/PEP02, a Novel Nanotherapeutic Eucapsulation of Irinotecan." Poster presented at MCR, Nov. 12-16, 2011, 8 pages.
Ko A, et al., "Excess Toxicity Associated with Docetaxel and Irinotecan in Patients with Metastatic, Gemcitabine-Refractory Pancreatic Cancer: Results of a Phase II Study," Cancer Invest. 26(1):47-52 (2008).
Lee M, et al., "5-Fluorouracil/Leucovorin Combined wtih Irinotecan and Oxaliplatin (FOLFIRINOX) as Second-Line chemotherapy in Patients with Advanced Pancreatic Cancer Who Have Progressed on Gemcitabine-Based Therapy," Chemotherapy. 59(4):273-9 (2013).
Lordick F, et al., "Phase II Study of Weekly Oxaliplatin Plus Infusional Fluorouracil and Folinic Acid (FUFOX Regiment) as First-Line Treatment in Metastatic Gastric Cancer," Br J Cancer. 93(2):190-4 (2005).
Louvet C, et al., "Gemcitabine in Combination With Oxaliplatin Compared With Gemcitabine Alone in Locally Advanced or Metastatic Pancreatic Cancer: Results of a GERCOR and GISCAD Phase III Trial," J Clin Oncol. 23 (15):3509-16 (2005).
Ma W, et al., "Nanoliposomal Irinotecan (nal-IRI, nal-IRI) Population Pharmacokinetics (PK) and Its Association with Efficacy and Safety in Patients with Solid Tumors." Poster presented at 2015 European Cancer Congress, Vienna, Austria, Sep. 25, 2015, 7 pages.
Mahaseth H, et al., "Modified FOLFIRINOX Regimen With Improved Safety and Maintained Efficacy in Pancreatic Adenocarcinoma," Pancreas. 42(8):1311-5 (2013).
Mans D, et al., "Sequence-Dependent Growth Inhibition and DNA Damage Formation by the Irinotecan-5-Fluorouracil Combination in Human Colon Carcinoma Cell Lines," Eur J Cancer. 35(13):1851-61 (1999).
Mathé G, et al., "A Phase I Trial of Trans-1-diamino-cyclohexane Oxalate-platinum (I-OHP)," Biomed Pharmacother, 40(10):372-376 (1986).
Mathé G, et al., "Oxalato-platinum or 1-OHP, a Third-Generation Platinum Complex: An Experimental and Clinical Appraisal and Preliminary Comparison with Cis-platinum and Carboplatinum," Biomed Pharmacother, 43(4):237-50 (1989).
Melis M, et al., "Can We Downstage Regionally Advanced Pancreatic Cancer to Resectable: a Phase I/II Study of Induction Oxaliplatin and 5FU Chemo-Radiation," 52nd Annual Meeting for Society for Surgery of the Alimentary Tract, May 6-10, 2011, http://meetings.ssat.com/abstracts/11ddw/P57.cgi, Abstract P57, 1 printed page.
Mizuno N., "Randomized Phase II Trial of S-1 versus S-1 Plus Irinotecan (IRIS) in Patients with Gemcitabine-Refractory Pancreatic Cancer," J Clin Oncol. 31(Suppl 4):Abstract 263 (2013), 2 printed pages.
Mullany S, et al., "Effect of Adding the Topoisomerase I Poison 7-ethyl-10-hydroxy-camptothecin (SN-38) to 5-Fluorouracil and

(56) References Cited

OTHER PUBLICATIONS

Folinic Acid in HCT-8 Cells: Elevated dTTP Pools and Enhanced Cytotoxicity," Cancer Chemother Pharmacol. 42(5):391-9 (1998).
Neuzillet C, et al., "FOLFIRI Regimen in Metastatic Pancreatic Adenocarcinoma Resistant to Gemcitabine and Platinum-Salts," World J Gastroenterol. 18(33):4533-41 (2012).
Oettle H, et al., "Second-Line Oxaliplatin, Folinic Acid, and Fluorouracil Versus Folinic Acid and Fluorouracil Alone or Gemcitabine-Refractory Pancreatic Cancer: Outcomes From the CONKO-003 Trial," J Clin Oncol. 32(23):2423-9 (2014).
Oh S, et al., "Pilot Study of Irinotecan/Oxaliplatin (IROX) Combination Chemotherapy for Patients with Gemcitabine-and 5-Fluorouracil- Refractory Pancreatic Cancer," Invest New Drugs. 28(3):343-9 (2010), Epub May 15, 2009.
Ohkawa S, et al., "Randomised Phase II Trial of S-1 Plus Oxaliplatin vs S-1 in Patients with Gemcitabine-Refractory Pancreatic Cancer," Br J Cancer 112(9):1428-34 (2015).
Okusaka T, et al., "Phase II Study of FOLFIRINOX for Chemotherapy-Naive Japanese Patients with Metastatic Pancreatic Cancer," Cancer Sci. 105(10):1321-6 (2014).
Oxaliplatin package insert, revision Nov. 2013, retrieved from https://www.accessdata.fda.gov/drugsatfda_docs/label/2013/022160s009lbl_pdf, 43 pages.
Pavillard V, et al., "Combination of Irinotecan (CPT11) and 5-Fluorouracil with an Analysis of Cellular Determinants of Drug Activity," Biochem Pharmacol. 56(10):1315-22 (1998).
Peddi P, et al., "Multi-Institutional Experience with FOLFIRINOX in Pancreatic Adenocarcinoma," Journal of the Pancreas (JOP). 13(5):497-501 (2012), online access, 11 printed pages.
EP2861210: Proprietor's statement of grounds of appeal to opposition decision dated Dec. 30, 2019, 35 pages.
EP2861210: Proprietor's Main and Auxiliary Requests MR, AR1, AR2, and AR3 with Proprietor's Statement of Grounds of Appeal in Opposition Proceedings filed Dec. 30, 2019, 4 pages.
EP2861210: Proprietor's statement of grounds of appeal to opposition decision dated Dec. 30, 2019, D23 (Declaration of Amy McKee M.D.) including D23A (Hoos W, et al., "Pancreatic Cancer Clinical Trials and Accrual in the United Sates." J Clin Oncol. 31(27)3432-8 (2013) and accompanying Appendix Table A1, Table A2, and Figure A1) and D23B (BIO Industry Analysis: Clinical Development Success Rates 2006-2015, Jul. 2016), 44 total pages.
EP2861210: Proprietor's statement of grounds of appeal to opposition decision dated Dec. 30, 2019, D24 (Declaration of Bruce Belanger, Ph.D.), 2 pages.
EP2861210: Reply to grounds of appeal following opposition and cover letter, dated Jul. 27, 2020, 35 pages.
Alagoz M, et al., "DNA Repair and Resistance to Topoisomerase I Inhibitors: Mechanisms, Biomarkers and Therapeutic Targets," Curr Med Chem. 19(23):3874-85 (2012).
American Chemical Society (ACS), http://www.cancer.org/cancer/pancreaticcancer/detailedguide/pancreatic-cancer-what-is-pancreatic-cancer, retrieved Dec. 1, 2016, 4 printed pages.
Amodeo S, et al., "Can we downstage locally advanced pancreatic cancer to resectable? A phase I/II study of Induction oxaliplatin and 5-FU chemoradiation," J Gastrointest Oncol. 9(5):922-35 (2018).
Camptosar package insert, revised May 16, 2002, 37 pages.
Cassileth P, et al., "Antiemetic Efficacy of Dexamethasone Therapy in Patients Receiving Cancer Chemotherapy," Arch Intern Med. 143(7):1347-9 (1983).
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancreatic Cancer (mPAC) Previously Treated with Gemcitabine-based Therapy." Poster handout at the Gastrointestinal Cancers Symposium of the ASCO meeting of Jan. 21-23, 2016, San Francisco, California, 2 pages.
Chen L, et al., "Expanded Analyses of NAPOLI-1: Phase 3 Study of MM-398 (nal-IRI), with or without 5-Fluorouracil and Leucovorin, versus 5-Fluorouracil and Leucovorin, in Metastatic Pancreatic Cancer (mPAC) Previously Treated with Gemcitabine-based Therapy." Presented Jan. 15, 2015, ASCO GI, 17 pages.
Chen L, et al., "Safety Across Subgroups in NAPOLI-1:A Phase 3 Study of nal-IRI (MM-398) ± 5-Fluorouracil and Leucovorin (5-FU/LV) Versus 5-FU/LV in Metastatic Pancreatic Cancer (mPAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 10 pages.
Chen L, et al., Abstract PD-023. "Safety Across Subgroups in NAPOLI-1:A Phase 3 Study of nal-IRI (MM-398) ± 5-Fluorouracil and Leucovorin (5-FU/LV) Versus 5-FU/LV in Metastatic Pancreatic Cancer (mPAC) Previously Treated with Gemcitabine-Based Therapy." Annals of Oncology. 27(Suppl 2):ii102-ii117 (2016), 1 page.
Chiang N-J, et al., "A Phase I Dose-Escalation Study of PEP02 (Irinotecan Liposome Injection) in Combination with 5-Fluorouracil and Leucovorin in Advanced Solid Tumors," BMC Cancer. 16(1):907 (2016). doi: 10.1186/s12885-016-2933-6, pp. 1-8.
Clinical Trials Identifier NCT00364143: Jan. 26, 2012 update, first posted Aug. 15, 2006, "A Phase I Study of IHL-305 (Irinotecan Liposome Injection) in Patients With Advanced Solid Tumors." Retrieved from ClinicalTrials.gov archive, 6 printed pages.
Clinical Trials Identifier NCT00813163: Jan. 11, 2011 update, "A Phase II Study of PEP02 as a Second Line Therapy for Patients With Metastatic Pancreatic Cancer." Retrieved from ClinicalTrials.gov archive, 3 printed pages.
Clinical Trials Identifier NCT00813163: Apr. 6, 2017 update, first posted Dec. 22, 2008, "A Phase II Study of PEP02 as a Second Line Therapy for Patients With Metastatic Pancreatic Cancer." Retrieved from ClinicalTrials.gov archive, 6 printed pages.
Clinical Trials Identifier NCT00940758: Apr. 6, 2017 update, first posted Jul. 16, 2009, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 5 printed pages.
Clinical Trials Identifier NCT01375816: Jul. 4, 2015 update, first posted Jun. 17, 2011, "A Randomized Phase II Study of PEP02 or Irinotecan in Combination With Leucovorin and 5-Fluorouracil in Second Line Therapy of Metastatic Colorectal Cancer." Retrieved from ClinicalTrials.gov archive, 10 printed pages.
Clinical Trials Identifier NCT02551991: Sep. 30, 2019 update, first posted Sep. 16, 2015, "A Randomized, Open-label, Phase 2 Study of Nanoliposomal Irinotecan (Nal-IRI)-Containing Regimens Versus Nab-Paclitaxel Plus Gemcitabine in Patients With Previously Untreated, Metastatic Pancreatic Adenocarcinoma." Retrieved from ClinicalTrials.gov archive, 5 printed pages.
Clinical Trials Identifier NCT02884128: Aug. 30, 2016 update, first posted Aug. 30, 2016, "A Multi-Center, Open-Label Phase I Dose-Escalation Study of PEP02 in Combination With 5-fluorouracil (5-FU) and Leucovorin (LV) in Advanced Solid Tumors." Retrieved from ClinicalTrials.gov archive, 5 printed pages.
Dayyani F, et al., Abstract B14. "CA 19-9 levels in patients with metastatic pancreatic adenocarcinoma receiving first-line therapy with liposomal irinotecan plus 5-fluorouracil/leucovorin and oxaliplatin (NAPOX)," In Proceedings of the AACR Special Conference on Pancreatic Cancer Advances in Science and Clinical Care; Sep. 6-9, 2019; Boston, MA; Cancer Res. 2019; 79(24 Suppl): Abstract nr B14, 3 printed pages.
Dean A, et al., "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Poster presented at the 18th European Society of Medical Oncology World Congress on Gastrointestinal Cancer; Barcelona, Spain; Jun. 29-Jul. 2, 2016, 14 pages.
Dean A, et al., Abstract P-287. "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Annals of Oncology. 27(Suppl 2):ii1-i85 (2016), 1 page.

(56) References Cited

OTHER PUBLICATIONS

Doxil package insert, revision Aug. 30, 2013, retrieved from https://www.accessdata.fda.gov/drugsatfda_docs/label/2013/050718s045lbl.pdf, 35 pages.
Drummond D, et al., "Optimizing Liposomes for Delivery of Chemotherapeutic Agents to Solid Tumors," Pharmacol Rev. 51(4):691-743 (1999).
Hsueh C-T, et al., "Nanovectors for Anti-Cancer Drug Delivery in the Treatment of Advanced Pancreatic Adenocarcinoma," World J Gastroenterol. 22(31):7080-90 (2016).
Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 9 pages.
Hubner R, et al., Abstract O-004. "Effects of nal-IRI (MM-398) ± 5-fluorouracil on Quality of Life (QoL) in NAPOLI-1: A Phase 3 Study in Patients with Metastatic Pancreatic Ductal Adenocarcinoma (mPDAC) Previously Treated with Gemcitabine." Annals of Oncology. 27(Suppl 2):ii118-ii128 (2016), 1 page.
Kalra A, et al., Abstract 5696. "Evaluating Determinants for Enhanced Activity of MM-398/PEP02; A Novel Nanotherapeutic Encapsulation of Irinotecan (CPT-11)." In Proceedings of the 103rd Annual Meeting of the American Association for Cancer Research; Mar. 31-Apr. 4, 2012; Chicago, IL. Cancer Res 2012; 72(8 Suppl):Abstract nr 5696. doi:1538-7445.AM2012-5696, 3 printed pages.
Kalra A, et al., "Evaluating Determinants for Enhanced Activity of MM-398/PEP02; A Novel Nanotherapeutic Encapsulation of Irinotecan (CPT-11)." Poster for abstract 5696 presented at American Association for Cancer Research 103rd Annual Meeting 2012, Mar. 31-Apr. 4, 2012, Chicago, IL, 11 pages.
Kalra A, et al., Abstract 5622. "The Tumor Microenvironment Modulates the Delivery and Activation of Liposomal Encapsulated Irinotecan, MM-398." In Proceedings of the 104th Annual Meeting of the American Association of Cancer Research; Apr. 6-10, 2013. Cancer Res 2013;73(8 Suppl):Abstract nr 5622, doi:10.1158/1538-7445. AM2013-5622, 2 printed pages.
Kalra A, et al., "The Tumor Microenvironment Modulates the Delivery and Activation of Liposomal Encapsulated Irinotecan, MM-398," Poster for abstract 5622 presented at the 104th Annual Meeting of the American Association of Cancer Research, Apr. 6-10, 2013, Washington DC, 10 pages.
Kalra A, et al., "Preclinical Activity of Nanoliposomal Irinotecan Is Governed by Tumor Deposition and Intratumor Prodrug Conversion," Cancer Res. 74(23):7003-13 (2014).
Klinz S, et al., "Identifying Differential Mechanisms of Action for MM-398/PEP02, a Novel Nanotherapeutic Encapsulation of Irinotecan," Mol Cancer Ther. 10(11 Suppl):Abstract C207. Molecular Targets and Therapeutics Meeting (2011), 2 printed pages.
Klinz S, et al., "Nanoliposomal Irinotecan (nal-IRI) is an Active Treatment and Reduces Hypoxia as Measured Through Longitudinal Imaging Using [18F]FAZA-PET in an Orthotopic Patient-Derived Tumorgraft Model of Pancreatic Cancer." Poster presented at AACR Pancreatic meeting Orlando, FL, May 12-15, 2016, 10 pages.
Ko A, "Nanomedicine Developments in the Treatment of Metastatic Pancreatic Cancer: Focus on Nanoliposomal Irinotecan," Int J Nanomedicine. 11:1225-35 (2016).
Maxwell F, et al., "CA 19-9 levels in patients with metastatic pancreatic adenocarcinoma receiving first-line therapy with liposomal irinotecan plus 5-fluorouracil/leucovorin and oxaliplatin (NAPOX)," Poster presented at the American Association for Cancer Research (AACR) Special Conference on Pancreatic Cancer: Advances in Science and Clinical Care, Sep. 6-9, 2019, Boston, MA, 7 pages.
Paz N, et al., "MM-398/PEP02, A Novel Liposomal Formulation of Irinotecan Demonstrates Stromal-Modifying Anti-Cancer Properties," Poster for abstract A643 presenated at the AACR Special Conference on Pancreatic Cancer: Progress and Challenges; Jun. 18-21, 2012; Lake Tahoe, NV, 9 pages.
Paz N, et al., Abstract A63. "MM-398/PEP02, A Novel Liposomal Formulation of Irinotecan, Demonstrates Stromal-Modifying Anti-cancer Properties," in Proceedings of the AACR Special Conference on Pancreatic Cancer: Progress and Challenges; Jun. 18-21, 2012; Lake Tahoe, NV. Cancer Res. 2012;72(12 Suppl):Abstract nr A63, 3 printed pages.
Von Hoff D, et al., "NAPOLI 1: Randomized Phase 3 Study of MM-398 (nal-IRI), With or Without 5-Fluorouracil and Leucovorin, Versus 5-Fluorouracil and Leucovorin, in Metastatic Pancreatic Cancer Progressed on or following Gemcitabine-Based Therapy." Poster presented at the ESMO World Congress on Gastrointestinal Cancer 2014, 11 pages.
Wainberg Z, et al., Abstract SO-005: "A Phase 1/2, Open-Label, Dose-Expansion Study of Liposomal Irinotecan (Nal-IRI) Plus 5-Fluorouracil/Leucovorin (5-FU/LV) and Oxaliplatin (OX) in Patients with Previously Untreated Metastatic Pancreatic Cancer," Ann Oncol. 30(Suppl 4): doi:10.1093/annonc/mdz157| iv123 (Jul. 2019), 1 page.
Wainberg Z, et al., "A phase 1/2, open-label, dose-expansion study of liposomal irinotecan (nal-IRI) plus 5-fluorouracil/leucovorin (5-FU/LV) and oxaliplatin (OX) in patients with previously untreated metastatic pancreatic cancer (mPAC)." Presentation presented at the ESMO 21st World Congress on Gastrointestinal Cancer, Barcelona, Spain, Jul. 3-6, 2019, 13 pages.
Wainberg Z, et al., Abstract LBA-1. "First-line liposomal irinotecan + 5 fluorouracil/leucovorin + oxaliplatin in patients with pancreatic ductal adenocarcinoma: Long-term follow-up results from a phase 1/2 study," Ann Oncol. 31(Suppl 3): S241 doi.org/10.1016/j.annonc.2020.04.076 (2020).
Wainberg Z, et al., "First-line liposomal irinotecan + 5-fluorouracil/leucovorin + oxaliplatin in patients with pancreatic ductal adenocarcinoma: long-term follow-up results from a phase 1/2 study." Presentation presented at the ESMO World Congress on Gastrointestinal Cancer, Jul. 1-4, 2020, 13 pages.
EP2861210: Reply to proprietor's grounds of appeal to opposition decision dated Jul. 27, 2020, D15c (EU clinical trial database for NAPOLI-1 study from Oct. 12, 2012, corresponds to D15b), 10 pages.
EP2861210: Reply to proprietor's grounds of appeal to opposition decision dated Jul. 27, 2020, D25 (Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012).
EP2861210: Reply to proprietor's grounds of appeal to opposition decision dated Jul. 27, 2020, D26 (Drummond D, et al., "Development of a Highly Active Nanoliposomal Irinotecan Using a Novel Intraliposomal Stabilization Strategy," Cancer Res. 66(6):3271-77 (2006)).
EP2861210: Reply to proprietor's grounds of appeal to opposition decision dated Jul. 27, 2020, D27 (Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 :2013)).
EP2861210: Reply to proprietor's grounds of appeal to opposition decision dated Jul. 27, 2020, D28 (Svenson S, "Clinical Translation of Nanomedicines," Current Opinion in Solid State and Materials Science. 16(6)287-294 (2012), article in press version, 7 pages).
EP2861210: Reply to proprietor's grounds of appeal to opposition decision dated Jul. 27, 2020, D29 (Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011)).
EP2861210: Reply to proprietor's grounds of appeal to opposition decision dated Jul. 27, 2020, D30 (Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 6 printed pages.).

(56) References Cited

OTHER PUBLICATIONS

EP2861210: Reply to proprietor's grounds of appeal to opposition decision dated Jul. 27, 2020, D31 (Cunningham D, et al., "Randomized Phase II Study of PEP02, Irinotecan, or Docetaxel as a Second-Line Therapy in Gastric or Gastroesophageal Junction Adenocarcinoma," J Clin Oncol. 29(4_supp):Abstract 6 (2011), 5 printed pages).
EP2861210: Reply to proprietor's grounds of appeal to opposition decision dated Jul. 27, 2020, D32 (Gerber D, "Miscellaneous Agents—Cytotoxics and Hormonal Agents," J Thorac Oncol. 7(12 Suppl 5):S387-9 (2012)).
EP2861210: Reply to proprietor's grounds of appeal to opposition decision dated Jul. 27, 2020, D33 (Noble C, et al., "Novel Nanoliposomal CPT-11 Infused by Convection-Enhanced Delivery in Intracranial Tumors: Pharmacology and Efficacy," Cancer Res. 66(5):2801-6 (2006)).
EP2861210: Reply to proprietor's grounds of appeal to opposition decision dated Jul. 27, 2020, D34 (Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007)).
EP2861210: Reply to proprietors grounds of appeal to opposition decision dated Jul. 27, 2020, D35 (Mullard A, "How Much Do Phase III Trials Cost?" Nat Rev Drug Discov. 17(11):777 (2018)).
EP2861210: Reply to proprietors grounds of appeal to opposition decision dated Jul. 27, 2020, D36 (the Medicines for Human Use (Clinical Trials) Regulations, 2004, 86 pages).
Adiwijaya B, et al., "Population Pharmacokinetics of Liposomal Irinotecan in Patients With Cancer," Clin Pharmacol Ther. 102(6):997-1005 (2017).
Alcindor T, et al., "Oxaliplatin: A Review in the Era of Molecularly Targeted Therapy," Curr Oncol. 18(1):18-25 (2011).
Alfert M, et al., "A Selective Staining Method for the Basic Proteins of Cell Nuclei," Proc Natl Acad Sci USA. 39 (10):991-9 (1953).
Anders C, et aL, "Phase 1 Expansion Study of Irinotecan Liposome Injection (nal-IRI) in Patients with Metastatic Breast Cancer (mBC): Findings from the Cohort with Active Brain Metastasis (BM)." Presentation presented at the Society for Neuro-Oncology Inaugural Conference on Brain Metasteses, Aug. 16-17, 2019, New York, NY, 11 pages.
Anders C, et aL, Abstract TRLS-06. "Phase 1 Expansion Study of Irinotecan Liposome Injection (nal-IRI) in Patients with Metastatic Breast Cancer (mBC): Findings from the Cohort with Active Brain Metastasis (BM)," Neuro-Oncology Advances. 1(Suppl 1):i9 doi.org/10.1093/noajnI/vdz014.039 (2019).
Ardizzoni A, et aL., "Topotecan, A New Active Drug in the Second-Line Treatment of Small-Cell Lung Cancer: a 3hase II Study in Patients with Refractory and Sensitive Disease," J Clin Oncol. 15(5):2090-6 (1997).
Bendell J, et al., "Treatment Patterns and Clinical Outcomes in Patients With Metastatic Colorectal Cancer Initially Treated with FOLFOX-Bevacizumab or FOLFIRI-Bevacizumab: Results From Aries, a Bevacizumab Observational cohort Study," Oncologist. 17(12):1486-95 (2012).
Bernards N, et al., "Liposomal Irinotecan Achieves Significant Survival and Tumor Burden Control in a Triple Negative Breast Cancer Model of Spontaneous Metastasis," Mol Pharm. 15(9):4132-8 (2018).
Bernards N, et al., "Liposomal Irinotecan Injection (nal-IRI) Achieves Significant Survival and Tumor Burden Control in a Triple Negative Breast Cancer Model of Spontaneous Metastasis," Poster presented at the World Molecular Imaging Congress Sep. 13-16, 2017, Philadelphia, Pennsylvania, 5 pages.
Butt R, et al., "Postfractionation for Enhanced Proteomic Analyses: Routine Electrophoretic Methods Increase the Resolution of Standard 2D-Page" J Proteome Res. 4(3):982-91 (2005).
Chan D, et al., "Evaluating the Pharmacodynamics and Pharmacokinetic Effects of MM-398, a Nanoliposomal rIinotecan (nal-IRI) in Subcutaneous Xenograft Tumor Models of Human Squamous Cell Carcinoma and Small Cell Lung Cancers," Cancer Res.74(19 Suppl): Abstract 4626 (2014), 2 printed pages.
Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell Carcinoma and Small Cell Lung Cancers," Poster presented at AACR Annual Meeting Apr. 5-9, 2014, 6 pages.
Chan D, et al., "PEP02 (Liposome Irinotecan) Effectively Inhibits Human Lung Squamous Cell Carcinoma and Small Cell Lung Cancers in Subcutaneous and Orthotopic Xenograft Tumor Models," J Thoracic Oncology. 6(6)(Suppl 2): 3420-1 (2011).
Chan D, et al., "PEP02 (Liposome Irinotecan) Effectively Inhibits Human Squamous Cell Carcinoma and Small Cell Lung Cancers in Subcutaneous and Orthotopic Xenograft Tumor Models." Presentation at the 14th World Conference on Lung Cancer, 2011, 11 pages.
Chan D, et al., "PEP02 (Liposome Irinotecan) Effectively Inhibits Human Squamous Cell Carcinoma and Small Cell Lung Cancers in Subcutaneous and Orthotopic Xenograft Tumor Models." Presentation at Santa Monica Lung Cancer Meeting, 2012, 9 pages.
Cheng L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl)Abstract 613 (2012), 6 printed pages.
Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012.
Chibaudel B, et al., "PEPCOL: a Gercor Randomized Phase II Study of Nanoliposomal Irinotecan PEP02 (MM-398) or Irinotecan with Leucovorin/5-Fluorouracil as Second-Line Therapy in Metastatic Colorectal Cancer", Cancer Med. 5(4):676-83 (2016).
Chiesa MD, et al., "Sequential Chemotherapy with Dose-Dense Docetaxel, Cisplatin, Folinic Acid and 5-Fluorouracil (TCF-dd) Followed by Combination of Oxaliplatin, Folinic acid, 5-Fluorouracil and Irinotecan (COFFI ) in Metastatic Gastric Cancer: Results of a Phase II Trial," Cancer Chemother Pharmacol. 67(1):41-8 (2011), epub 2010.
Clarke J, et al., "A Phase 1 Trial of Intravenous Liposomal Irinotecan in Patients with Recurrent High-Grade Glioma," Cancer Chemother Pharmacol. 79(3):603-10 (2017).
Clinical Trials Identifier NCT00104754: Jul. 20, 2016, update, first posted Mar. 4, 2005, "Phase II Trial of Liposome Encapsulated SN38 (LE-SN38) in the Treatment of Small Cell Lung Cancer." Retrieved from ClinicalTrials.gov archive, 8 printed pages.
Clinical Trials Identifier NCT00311610: Jun. 29, 2016 update, first posted Apr. 6, 2006, "Phase II Trial of LE SN38 in Patients with Metastatic Colorectal Cancer After Progression on Oxaliplatin." Retrieved from ClinicalTrials.gov archive, 3 printed pages.
Clinical Trials Identifier NCT00734682: Jan. 7, 2015 update, first posted Aug. 14, 2008, "A Phase I Trial of Nanoliposomal CPT-11 (NL CPT-11) in Patients With Recurrent High-Grade Gliomas." Retrieved from ClinicalTrials.gov archive, 6 printed pages.
Clinical Trials Identifier NCT00813072: Mar. 2, 2012 update, first posted Dec. 22, 2008, "A Randomized Phase II Study of PEP02, Irinotecan or Docetaxel as a Second Line Therapy in Patients With Locally Advanced or Metastatic Gastric or Gastroesophageal Junction Adenocarcinoma." Retrieved from ClinicalTrials.gov archive, 9 printed pages.
Clinical Trials Identifier NCT01770353: Aug. 9, 2013 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 3 printed pages.
Clinical Trials Identifier NCT01770353: Apr. 26, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.
Clinical Trials Identifier NCT01770353: May 6, 2015 update, "A Pilot Study in Patients Treated with MM-398 to Determine Tumor Drug Levels and to Evaluate the Feasibility of Ferumoxytol Mag-

(56) References Cited

OTHER PUBLICATIONS netic Resonance Imaging to Measure Tumor Associated Macrophages." Retrieved from ClinicalTrials.gov archive, 4 printed pages.

Clinical Trials Identifier NCT01770353: Mar. 22, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.

Clinical Trials Identifier NCT01770353: Jul. 7, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.

Clinical Trials Identifier NCT02013336: Feb. 6, 2017 update, first posted Dec. 17, 2013, "Phase 1 Dose-escalating Study of MM-398 (Irinotecan Sucrosofate Liposome Injection) Plus Intravenous Cyclophosphamide in Recurrent or Refractory Pediatric Solid Tumors" Retrieved from ClinicalTrials.gov archive, 6 printed pages.

Clinical Trials Identifier NCT02022644: May 8, 2017 update, first posted Dec. 30, 2013, "A Phase I Study of Convection-Enhanced Delivery of Liposomal-Irinotecan Using Real-Time Imaging With Gadolinium in Patients With Recurrent High Grade Glioma." Retrieved from ClinicalTrials.gov archive, 9 printed pages.

Clinical Trials Identifier NCT02631733: Dec. 15, 2015 update, "A Phase I Study of a Combination of MM-398 and Veliparib in Solid Tumors." Retrieved from ClinicalTrials.gov archive, 6 printed pages.

Clinical Trials Identifier NCT02631733: Feb. 16, 2016 update, "A Phase I Study of a Combination of MM-398 and Veliparib in Solid Tumors." Retrieved from ClinicalTrials.gov archive, 6 printed pages.

Clinical Trials Identifier NCT02631733: Jun. 20, 2016 update, "A Phase I Study of a Combination of MM-398 and Veliparib in Solid Tumors." Retrieved from ClinicalTrials.gov archive, 6 printed pages.

Clinical Trials Identifier NCT02631733: Jun. 21, 2016 update, "A Phase I Study of a Combination of MM-398 and Veliparib in Stolid Tumors." Retrieved from ClinicalTrials.gov archive, 6 printed pages.

Clinical Trials Identifier NCT02631733: Jul. 6, 2016 update, "A Phase I Study of a Combination of MM-398 and Veliparib in Solid Tumors." Retrieved from ClinicalTrials.gov archive, 6 printed pages.

Clinical Trials Identifier NCT02631733: Jul. 11, 2016 update, "A Phase I Study of a Combination of MM-398 and Veliparib in Solid Tumors." Retrieved from ClinicalTrials.gov archive, 6 printed pages.

Clinical Trials Identifier NCT02631733: 2016-07-19 update, "A Phase I Study of a Combination of MM-398 and Veliparib in Solid Tumors." Retrieved from ClinicalTrials.gov archive, 6 printed pages.

Clinical Trials Identifier NCT02631733: Aug. 7, 2016 update, "A Phase I Study of a Combination of MM-398 and Veliparib in Solid Tumors." Retrieved from ClinicalTrials.gov archive, 6 printed pages.

Clinical Trials Identifier NCT02631733: Sep. 21, 2016 update, "A Phase I Study of a Combination of MM-398 and Veliparib in Solid Tumors." Retrieved from ClinicalTrials.gov archive, 6 printed pages.

Clinical Trials Identifier NCT02631733: Oct. 4, 2017 update, first posted Dec. 16, 2015, "A Phase I Study of a Combination of MM-398 and Veliparib in Solid Tumors." Retrieved from ClinicalTrials.gov archive, 10 printed pages.

Clinical Trials Identifier NCT03088813: Sep. 30, 2019 update, first posted Mar. 32, 2017, "Study of Irinotecan Liposome Injection (ONIVYDE®) in Patients With Small Cell Lung Cancer." Retrieved from ClinicalTrials.gov archive, 8 printed pages.

Cortès J, et al., Abstract CT154. "Multicenter Open-Label, Phase II Trial, to Evaluate the Efficacy and Safety of Liposomal Irinotecan (nal-IRI) for Progressing Brain Metastases in Patients with HER2-Negative Breast Cancer (the Phenomenal Study)," In Proceedings of the American Association for Cancer Research Annual Meeting 2018; Apr. 14-18, 2018; Chicago, Illinois. Cancer Res. 2018;78(13 Suppl):Abstract nr CT154, 3 printed pages.

Davidson D, et al., "The PARP Inhibitor ABT-888 Synergizes Irinotecan Treatment of Colon Cancer Cell Lines," Invest New Drugs. 31(2);461-8 (2013) DOI: 10.1007/s10637-012-9886-7; Epub Oct. 9, 2012, 8 pages.

Dickinson P, et al., "Canine Model of Convection-Enhanced Delivery of Liposomes Containing CPT-11 Monitored with Real-Time Magnetic Resonance Imaging," J. Neurosurg. 108(5):989-98 (2008).

Dickinson P, et al., "Canine Spontaneous Glioma: A Translational Model System for Convection-Enhanced Delivery," Neuro Oncol. 12(9):928-40; Epub 10:1093/neuonc/nog046, 1-13 (2010).

Dósa E, et al., "Magnetic Resonance Imaging of Intracranial Tumors: Intra-Patient Comparison of Gadoteridol and Ferumoxytol," Neuro Oncol. 13(2):251-60 (2011) doi: 10.1093/neuonc/nog172. Epub 2010.

Eckardt J, et al., "Phase III Study of Oral Compared With Intravenous Topotecan As Second-Line Therapy in Small-Cell Lung Cancer," J Clin Oncol. 25(15)2086-92 (2007).

English translation of title and abstract for Hasegawa, Y, "Biomarker as Predictive Safety Testing in Oncology", Igaku No Ayumi (Journal of Clinical and Experimental Medicine), 224(13)1171-4 (2008) (original in Japanese).

Fitzgerald J, et al., "Systems Pharmacology Identification of Tumour Nanoparticle Permeability as Predictor of clinical Anti-Cancer Activity of MM-398, Nanoliposomal Irinotecan, nal-IRI." Poster presented at 15th International conference on Systems Biology. Sep. 14-18, 2014, 10 pages.

Fleming D. "Importance of sequence in chemotherapy administration," retrieved from http://www. oncologynurseadvisor.com/advisor-forum/importance-of-sequence-in-chemotherapy-administration/article/378072/(2014).

Fuchs C, et al., "Phase III Comparison of Two Irinotecan Dosing Regimens in Second-Line Therapy of Metastatic Colorectal Cancer," J Clin Oncol. 21(5):807-14 (2003).

Gahramanov S, et al., "Pseudoprogression of Glioblastoma After Chemo-and Radiation Therapy: Diagnosis by using Dynamic Susceptibility-Weighted Contrast-Enhanced Perfusion MR Imaging with Ferumoxytol versus Gadoteridol and Correlation with Survival," Radiology. 266(3):842-52 (2013). doi: 10.1148/radiol.12111472. Epub Nov. 30, 2012.

Genther Williams S, et al., "Treatment with the PARP Inhibitor, Niraparib, Sensitizes Colorectal Cancer Cell Lines to Irinotecan Regardless of MSI/MSS Status," Cancer Cell Int. 15(1):14, doi: 10.1186/s12935-015-0162-8 (2015), pp. 1-11.

Gilbert D, et al., "Topoisomerase I Inhibition in Colorectal Cancer: Biomarkers and Therapeutic Targets," Br J Cancer. 106(1):18-24 (2012), doi: 10.1038/bjc.2011.498, Epub Nov. 22, 2011.

Hanna N, et al., "Randomized Phase III Trial Comparing Irinotecan/Cisplatin with Etoposide/Cisplatin in Patients with Previously Untreated Extensive-Stage Disease Small-Cell Lung Cancer," J Clin Oncol. 24(13):2038-43 (2006).

Hare J, et al., "Treatment of Colorectal Cancer Using a Combination of Liposomal Irinotecan (Irinophore C(TM)) and 5-Fluorouracil," PLoS One. 8(4):e62349, doi: 10.1371/journal.pone.0062359, 12 pages (2013).

Hayashi H, et al., "Phase II Study of Bi-Weekly Irinotecan for Patients with Previously Treated HER2-Negative Metastatic Breast Cancer: KMBOG0610B," Breast Cancer. 20(2):131-6 (2013); doi: 10.1007/s12282-011-0316-z. Epub Nov. 29, 2011.

Hayes M, et al., "Assembly of Nucleic Acid-Lipid Nanoparticles from Aqueous-Organic Monophases," Biochim Biophys Acta. 1758(4):429-42 (2006).

Honig A, et al., "Brain Metastases in Breast Cancer—an In Vitro Study to Evaluate New Systemic Chemotherapeutic Options," Anticancer Res. 25(3A):1531-7 (2005).

Huber R, et al., "Efficacy of a Toxicity-Adjusted Topotecan Therapy in Recurrent Small Cell Lung Cancer," Eur Respir J. 27(6):1183-9 (2006).

Hycamtin (topotecan hydrochloride) for injection package insert, revision Feb. 28, 2014, retrieved from https:// www.accessdata.fda.gov/drugsaffda_docs/label/2014/020671s0201b1.pdf, 23 pages.

Hycamtin (topotecan) for injection package insert, revision Jun. 2, 2015, retrieved from https://www.accessdata.fda. gov/drugsatfda_docs/label/2015/020671s0211b1_pdf, 21 pages.

(56) References Cited

OTHER PUBLICATIONS

Kalra A, et al., Abstract 2065: "Magnetic Resonance Imaging with an Iron Oxide Nanoparticle Demonstrates Preclinically the Feasibility of Predicting Intratumoral Uptake and Activity of MM-398, a Nanoliposomal Irinotecan (nal-IRI)." Poster presented at American Association for Cancer Research annual meeting 2014, San Diego, CA, 5 pages.

Kalra A., "Magnetic Resonance Imaging (MRI) to Predict Tumor Drug Delivery and Response to Nanoliposomal Therapy." Presentation presented at Tumor Models Boston 2014, 32 pages.

Kang M, et al., "Activity of MM-398, Nanoliposomal Irinotecan (nal-IRI), in Ewing's Family Tumor Xenografts Is Associated with High Exposure of Tumor to Drug and High SLFN11 Expression," Clin Cancer Res. 21(5):1139-50 :2015).

Kim J, et al., "Efficient Prioritization of Potential Diagnostic Biomarkers Using a Systems Pharmacology Approach: case Study of MM-398 (Irinotecan sucrosofate liposome injection)." Presentation presented at the Pharmacokietics UK 2013 Meeting, Oct. 31, 2013, Harrogate, North Yorkshire, 34 pages.

Kim J, et al., "Efficient Prioritization of Potential Diagnostic Biomarkers Using a Systems Pharmacology Approach: case Study of MM-398, an Irinotecan Sucrosofate Liposome Injection." Abstract for Pharmacokietics UK 2013 Meeting, Oct. 30-Nov. 1, 2013, Harrogate, North Yorkshire, 2 pages.

Kim J, et al., "Systems Pharmacology Modeling Identifies Unique Parameters That Drive Tumor SN38 Levels for Liposomal Irinotecan (MM-398) Compared to Irinotecan." Abstract presented at 14th International Conference on Systems Biology; Copenhagen, Denmark; Aug. 29-Sep. 4, 2013, 1 page.

Kim J, et al., "Systems Pharmacology Modeling Identifies Unique Parameters That Drive Tumor SN38 Levels for Liposomal Irinotecan (MM-398) Compared to Irinotecan." Poster presented at 14th International Conference on Systems Biology; Copenhagen, Denmark; Aug. 29-Sep. 4, 2013, 11 pages.

Kim J, et al., Abstract A6. "Sustained Intratumoral Activation of MM-398 Results in Superior Activity Over Irinotecan Demonstrated by Using a Systems Pharmacology Approach, " In: Proceedings of the AACR Special Conference on Chemical Systems Biology: Assembling and Interrogating Computational Models of the Cancer Cell by Chemical Perturbations; Jun. 27-30, 2012; Boston, MA. Cancer Res. 2012;72(13 Suppl):Abstract nr A6, 3 printed pages.

Kim J, et. al., "Systems Pharmacology Based Biomarker Potentially Predicts Clinical Anti-Cancer Activity of MM-398, Nanoliposomal Irinotecan, nal-IRI." Poster presented at American Conference on Pharmacometrics, Oct. 12-15, 2014, 10 pages.

Kirpotin D, et al. "Antibody Targeting of Long-Circulating Lipidic Nanoparticles Does Not Increase Tumor Locatlization but Does Increase Internalization in Animal Models," Cancer Res. 66(13):6732-40 (2006).

Klinz S, et al., Abstract C293: "Irinotecan Sucrosofate Liposome Injection, MM-398, Demonstrates Superior Activity and Control of Hypoxia as Measured Through Longitudinal Imaging Using [18F] FAZA PET Compared to Free Irinotecan in a Colon Adenocarcinoma Xenograft Model." Poster presented at AACR-NCI-EORTC International conference on Molecular Targets and Cancer Therapeutics on Oct. 19, 2013, 7 pages.

Klinz S, et al.,"MM-302 a HER2-targeted Liposomal Doxorubicin, Shows Binding/Uptake and Efficacy in HER2 2+ Cells and Xenograft Models," Cancer Res. 71:Abstract 3637 (2011), 1 printed page.

Korn R, "Advanced Imaging with Ferumoxytol MRI to Predict Drug Delivery." Presentation presented at Pancreatic Cancer 2014, Feb. 22, 2014, 23 pages.

Koshkaryev A, et al., "Differential Tissue Clearance Results in Improved Therapeutic Index for Nanoliposomal Irinotecan (nal-IRI; Onivyde) when Combined with the PARP Inhibitor Veliparib." Poster presented at AACR Meeting on Apr. 16-20, 2016, 5 pages.

Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007).

Kummar S, et al. "Phase I Study of PARP Inhibitor ABT-888 in Combination with Topotecan in Adults with Refractory Solid Tumors and Lymphomas," Cancer Res. 71(17):5626-34 (2011), Epub Jul. 27, 2011.

Landry R, et al., "Pharmacokinetic Study of Ferumoxytol: A New Iron Repalcement Therapy in Normal Subjects and Hemodialysis Patients," Am J Nephrol. 25(4):400-10 (2005).

Lee H, et al., A Novel 64Cu-Liposome PET Agent (MM-DX-929) Predicts Response to Liposomal Chemotherapeutics in Preclinical Breast Cancer Models, Cancer Res. 72(24 Suppl): Abstract nrP4-02-05 (2012), San Antonio Breast cancer Symposium, Dec. 4-8, 2012, 2 printed pages.

Lee H, et al., A Novel 64Cu-Liposome PET Agent (MM-DX-929) Predicts Response to Liposomal Chemotherapeutics in Preclinical Breast Cancer Models, Poster presented at San Antonio Breast Cancer Symposium, Dec. 4-8, 2012, 13 pages.

Lee H, et al., "Delivery and Anti-Tumor Activity of Nanoliposomal Irinotecan (Nal-IRI, MM-398) in Metastatic Xenograft Models of Triple Negative Breast Cancer." Poster presented at 39th Annual San Antonio Breast Cancer Symposium, Dec. 6-10, 2016, 8 pages.

Leonard S, et al., "Extended Topoisomerase 1 Inhibition Through Liposomal Irinotecan Results in Improved Efficacy overr Topotecan and Irinotecan in Models of Small-Cell Lung Cancer," Anti-Cancer Drugs. 28(10):1086-96 (2017).

Leonard S, et al., "Irinotecan Liposome Injection has Greater Anti-Tumor Activity than Topotecan and Irinotecan in Mouse Models of Small Cell Lung Cancer," Poster presented at AACR 110th Annual World Congress 2017, Washington, DC, Apr. 1-5, 2017, 6 pages.

Leonard S, et al., "Preclinical Support for Evaluation of Irinotecan Liposome Injection (nal-IRI, MM-398) in Small Cell Lung Cancer," Abstracts from the IASLC 17th World Conference on Lung Cancer held Dec. 4-7, 2016, J Thoracic Oncology. 12(1)(Suppl):S699 (2016), 1 page.

Leonard S, et al., "Preclinical Support for Evaluation of Irinotecan Liposome Injection (nal-IRI, MM-398) in Small Cell Lung Cancer," Poster presented at 17th World Conference on Lung Cancer, Vienna, Austria, Dec. 4-7, 2016, 5 pages.

Lorusso P, et al., "Abstract CT325: Combination of the PARP Inhibitor Veliparib (ABT888) with Irinotecan in Patients with Triple Negative Breast Cancer: Preliminary Activity and Signature of Response." Proceedings: AACR 106th Annual Meeting, Apr. 18-22, 2015, Philadelphia, PA (2015), 3 printed pages.

Lorusso P, et al., "Phase I Safety, Pharmacokinetic, and Pharmacodynamic Study of the Poly(ADP-ribose) Polymerase (PARP) Inhibitor Veliparib (ABT-888) in Combination with Irinotecan in Patients with Advanced Solid Tumors," Clin Cancer Res. 22(13):3227-37 (2016), Epub Feb. 3, 2016.

Lorusso P, et al., "Phase I Study of the Safety, Pharmacokinetics (PK), and Pharmacodynamics (PD) of the Poly (ADP-ribose) Polymerase (PARP) Inhibitor Veliparib (ABT-888; V) in Combination with Irinotecan (CPT-11; Ir) in Patients (pts) with Advanced Solid Tumors," Supplement ASCO Meeting Library, Jun. 5, 2011, 1 page.

Lorusso P, et al., "Phase I Study of the Safety, Pharmacokinetics (PK), and Pharmacodynamics (PD) of the Poly (ADP-ribose) Polymerase (PARP) Inhibitor Veliparib (ABT-888; V) in Combination with Irinotecan (CPT-11; Ir) in Patients (pts) with Advanced Solid Tumors," Journal of Clinical Oncology 29.15_suppl: Abstract 3000 (2011), 3 printed pages.

Lorusso P, et al., "Phase I Study of the Safety, Pharmacokinetics, and Pharmacodynamics of the Poly(ADP-ribose) Jolymerase (PARP) Inhibitor Veliparib (ABT-888) in Combination with Irinotecan (CPT-11) in Patients with Advanced Solid Tumors," Presentation presented at American Society of Clinical Oncology 2011 Meeting, 37 pages.

Lynparza™ (olaparib) capsules package insert, ©AstraZeneca. 2014, Revised: Dec. 2014, 6 pages.

(56) References Cited

OTHER PUBLICATIONS

Mamot C, et al., "Epidermal Growth Factor Receptor-Targeted Immunoliposomes Significantly Enhance the Efficacy of Multiple Anticancer Drugs in Vivo," Cancer Res. 65(24):11631-8 (2005).
Mamot C, et al., "Extensive Distribution of Liposomes in Rodent Brains and Brain Tumors Following Convection-Enhanced Delivery," J Neurooncol. 68(1):1-9 (2004).
Masuda N, et al., "CPT-11: A New Derivative of Camptothecin for the Treatment of Refractory or Relapsed Small-Cell Lung Cancer," J Clin Oncol. 10(8):1225-9 (1992).
Merrimack Pharmaceuticals, "Merrimack Pharmaceuticals Initiates Cross-Tumor Study to Investigate Potential Predictive Response Markers for a Developmental Nanotherapeutic Chemotherapy," Dec. 19, 2012. Retrieved from http:investors.merrimack.com/news-releases/news-release-details/merrimack-pharmaceuticals-initiates-cross-tumor-study, 2 printed pages.
Messerer C, et al., "Liposomal Irinotecan: Formulation Development and Therapeutic Assessment in Murine Xenograft Models of Colorectal Cancer," Clin Cancer Res. 10(19):6638-49 (2004).
Miller M, et al. "Predicting Therapeutic Nanomedicine Efficacy Using a Companion Magnetic Resonance Imaging Nanoparticule," Sci Transl Med. 7:314ra183 (2015), pp. 1-12, Editor's Summary (1 page), and Supplementary Materials (24 pages).
Miller M, et al., "Tumour-Associated Macrophages Act as a Slow-Release Reservoir of Nano-Therapeutic Pt(IV) Pro-Drug," Nat. Commun. 6:8692, doi: 10.1038/ncomms9692, 13 pages (2015), Supplementary Figures 1-9 (9 pages), Supplementary Table 1 (1 page), and Supplementary References (1 page).
Mirtsching B, et al., "Irinotecan-induced Immune Thrombocytopenia," Am J Med Sci. 347(2):167-9 (2014).
Mohammad A, et al., "Liposomal Irinotecan Accumulates in Metastatic Lesions, Crosses the Blood-Tumor Barrier (BTB), and Prolongs Survival in an Experimental Model of Brain Metastases of Triple Negative Breast Cancer," Pharm Res. 35(2):31; doi.org/10.1007/s11095-017-2278-0 (2018), 10 pages.
Mukhtar R, et al., "Elevated PCNA+Tumor-Associated Macrophages in Breast Cancer are Associated with Early Recurrence and Non-Caucasian Ethnicity," Breast Cancer Res Treat. 130(2):635-44 (2011).
Murai J, et al., "Identification of Novel PARP Inhibitors Using a Cell-Based TDP1 Inhibitory Assay in a Quantitative High-Throughput Screening Platform," Author manuscript; Published in final edited form as: DNA Repair (Amst). 21:177-82 (2014), 13 pages.
Murai J, et al., "Rationale for Poly(ADP-ribose) Ploymerase (PARP) Inhibitors in Combination Therapy with Campothecins or Temozolomide Based on PARP Trapping versus Catalytic Inhibition," J Pharmacol Exp Ther. 349 (3):408-16 (2014).
No authors listed. "5HT3-receptor Antagonists as Antiemetics in Cancer," Drug Ther Bull. 43(8):57-62 (2005).
Noble C, et al., "Novel Nanoliposomal CPT-11 Infused by Convection-Enhanced Delivery in Intracranial Tumors: Pharmacology and Efficacy," Cancer Res. 66(5):2801-6 (2006).
Noble C, et al., "Pharmacokinetics, Tumor Accumulation and Antitumor Activity of Nanoliposomal Irinotecan Following Systemic Treatment of Intracranial Tumors," Nanomedicine. 9(14):2099-108 (2014).
O'Brien M, et al., "Phase III Trial Comparing Supportive Care Alone With Supportive Care With Oral Topotecan in Patients With Relapsed Small-Cell Lung Cancer," J Clin Oncol. 24(34):5441-7 (2006).
Owonikoko T, et al., "A Systematic Analysis of Efficacy of Second-Line Chemotherapy in Sensitive and Refractory Small-Cell Lung Cancer," J Thorac Oncol. 7(5):866-72 (2012).
Pallis A, et al., "A Multicenter Randomized Phase II Study of the Irinotecan/Gemcitabine Doublet Versus Irinotecan Monotherapy in Previously Treated Patients with Extensive Stage Small-Cell Lung Cancer," Lung Cancer. 65 (2):187-91 (2009), Epub Dec. 18, 2008.
Park J, et al., "Anti-HER2 Immunoliposomes: Enhanced Efficacy Atrributable to Targeted Delivery,"Clin Cancer Res. 8 (4):1172-81 (2002).

Patton W, "Detection Technologies in Proteome Analysis", J Chromatogr B. 771(1-2):3-31 (2002).
Paz-Ares L, et al., "Efficacy and Safety of Irinotecan Liposome Injection (nal-IRI) in Patients with Small Cell Lung cancer (SCLC)," Presentation presented at 2019 World Conference on Lung Cancer; Sep. 7-10, 2019; Barcelona, Spain; 9 pages.
Paz-Ares L, et al., "Liposomal Irinotecan vs Topotecan in Patients with Small Cell Lung Cancer Who Have Progressed on/After Platinum-Based Therapy." Poster presented Sep. 23-26, 2018 at 19th World Conference on Lung Cancer meeting, 9 pages.
Paz-Ares L, et al., "Resilient: Study of Irinotecan Liposome Injection (nal-IRI) in Patients with Small Cell Lung cancer—Preliminary Findings from Part 1 Dose-Defining Phase," Poster presented at ASCO in Chicago, IL May 31-Jun. 4, 2019, 6 pages.
Paz-Ares L, et al., "Resilient: Study of Irinotecan Liposome Injection (nal-IRI) in Patients with Small Cell Lung cancer—Preliminary Findings from Part 1 Dose-Defining Phase," Abstract No. 8562, J Clin Oncol. 37(15)(Suppl):8562 (2019), 3 pages.
Paz-Ares Rodriguez L, et al., Abstract OA03.03. "Initial Efficacy and Safety Results of Irinotecan Liposome Injection (NAL-IRI) in Patients With Small Cell Lung Cancer," 2019 World Conference on Lung Cancer Abstracts; Sep. 7-10, 2019; Barcelona, Spain; pp. 220-221.
PCT/GB2017/053293: PCT International Preliminary Report on Patentability dated May 7, 2019, 7 pages.
PCT/GB2017/053293: PCT International Search Report and Written Opinion dated Feb. 2, 2018, 12 pages.
PCT/IB2017/000681: PCT International Preliminary Report on Patentability dated Nov. 20, 2018, 6 pages.
PCT/IB2017/000681: PCT International Search Report and Written Opinion dated Aug. 25, 2017, 8 pages.
PCT/US2013/046914: PCT International Preliminary Report on Patentability dated Dec. 23, 2014, 7 pages.
PCT/US2013/046914: PCT International Search Report dated Sep. 2, 2013, 3 pages.
PCT/US2013/075513: PCT International Preliminary Report on Patentability dated Jun. 16, 2015, 7 pages.
PCT/US2013/075513: PCT International Search Report dated Jun. 6, 2014, 2 pages.
PCT/US2014/062007: PCT International Preliminary Report on Patentability dated Apr. 26, 2016, 10 pages.
PCT/US2014/062007: PCT International Search Report dated Jan. 9, 2015, 3 pages.
PCT/US2015/064491: PCT International Preliminary Report on Patentability dated Jun. 13, 2017, 7 pages.
PCT/US2015/064491: PCT International Search Report dated Feb. 19, 2016, 4 pages.
PCT/US2016/027515: PCT International Preliminary Report on Patentability dated Oct. 17, 2017, 8 pages.
PCT/US2016/027515: PCT International Search Report dated Jun. 27, 2016, 4 pages.
PCT/US2016/047727: PCT International Preliminary Report on Patentability dated Feb. 27, 2018, 6 pages.
PCT/US2016/047727: PCT International Search Report and Written Opinion dated Nov. 16, 2016, 8 pages.
PCT/US2016/047814: PCT International Preliminary Report on Patentability dated Feb. 20, 2018, 6 pages.
PCT/US2016/047814: PCT International Search Report dated Nov. 17, 2016, 3 pages.
PCT/US2016/047827: PCT International Preliminary Report on Patentability dated Feb. 20, 2018, 6 pages.
PCT/US2016/047827: PCT International Search Report dated Nov. 17, 2016, 3 pages.
Peinert S, et al., "Safety and Efficacy of Weekly 5-Fluorouracil/Folinic Acid/Oxaliplatin/Irinotecan in the First-Line Treatment of Gastrointestinal Cancer," Ther Adv Med Oncol. 2(3):161-74 (2010).
Pfizer Background Document on the UGT1A1 Polymorphisms and Irinotecan Toxicity: ACPS Nov. 3, 2004 Advisory Committee Meeting, 19 pages.
Ramanathan R, et al., "Correlation between Ferumoxytol Uptake in Tumor Lesions by MRI and Response to Nanoliposomal Irinotecan in Patients with Advanced Solid Tumors: A Pilot Study," Clin Cancer Res. 23(14):3638-48 (2017).

(56) References Cited

OTHER PUBLICATIONS

Ramanathan R, et al., "Lesion Characterization with Ferumoxytol MRI in Patients with Advanced Solid Tumors and Correlation with Treatment Response to MM-398, Nanoliposomal Irinotecan (nal-IRI)." Poster presented at EORTC-NCI-AACR International Conference on Molecular Targets and Cancer Therapeutics on Nov. 20, 2014, 7 pages.
Ramanathan R, et al., "Lesion Characterization with Ferumoxytol MRI in Patients with Advanced Solid Tumors and Correlation with Treatment Response to MM-398, Nanoliposomal Irinotecan (nal-IRI)," Abstract No. 261. Eur. J. Cancer, 50:87 (2014).
Ramanathan R, et al., "Pilot Study in Patients with Advanced Solid Tumors to Evaluate Feasibility of Ferumoxytol (FMX) As a Tumor Imaging Agent Prior to MM-398, a Nanoliposomal Irinotecan (nal-IRI)." Poster presented at AACR Annual Meeting 2014, San Diego, CA, 9 pages.
Raymond E, et al., "Multicentre Phase II Study and Pharmacokinetic Analysis of Irinotecan in Chemotherapy-Naive Patients with Glioblastoma," Ann Oncol. 14(4):603-14 (2003).
Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013).
Sachdev J, et al., "A Phase 1 Study in Patients with Metastatic Breast Cancer to Evaluate the Feasibility of Magnetic Resonance Imaging with Ferumoxytol as a Potential Biomarker for Response to Treatment with Irinotecan Liposome Injection (nal-IRI, MM-398)." Poster presented at 38th Annual San Antonio Breast Cancer Symposium on Dec. 8, 2015, 10 pages.
Sachdev J, et al., "Characterization of Metastatic Breast Cancer Lesions with Ferumoxytol MRI and Clinical Response to MM-398, Nanoliposomal Irinotecan (nal-IRI), in 3 Subjects." Poster presented at San Antonio Breast cancer Symposium 2014, 8 pages.
Sachdev J, et al., "Characterization of Metastatic Breast Cancer Lesions with Ferumoxytol MRI and Treatment Response to MM-398, Nanoliposomal Irinotecan (nal-IRI)," Cancer Res.75(9 Suppl): Abstract P5-01-06 (2015), 3 printed pages.
Sachdev J, et al., Abstract CT048. "Phase I Expansion Study of Irinotecan Liposome Injection (nal-IRI) in Patients with Metastatic Breast Cancer (mBC)," Cancer Res. In Proceedings of the American Association for Cancer Research Annual Meeting 2019; Mar. 29-Apr. 3, 2019; Atlanta, GA. Cancer Res. 2019; 79(13 Suppl):Abstract nr CT048, 4 printed pages.
Ettrich T, et al., "Liposomal Irinotecan (nal-IRI) Plus 5-Fluorouracil (5-FU) and Leucovorin (LV) or Gemcitabine Plus Cisplatin in Advanced Cholangiocarcinoma: The AIO-NIFE-Trial, an Open Label, Randomized, Multicenter Phase II Trial," Poster presented at the American Society of Clinical Oncology (ASCO) Annual Meeting, Chicago, Illinois, Jun. 1-5, 2018, 5 pages.
Ettrich T, et al., Abstract TPS4145. "Liposomal Irinotecan (nal-IRI) Plus 5-Fluorouracil (5-FU) and Leucovorin (LV) or Gemcitabine Plus Cisplatin in Advanced Cholangiocarcinoma: The AIO-NIFE-Trial, an Open Label, Randomized, Multicenter Phase II Trial," J Clin Oncol. 36(15_Suppl):TPS4145 DOI: 10.1200/JCO.2018.36.15_suppl.TPS4145 (2018), 2 printed pages.
Falcone a, et al., "Sequence Effect of Irinotecan and Fluorouracil Treatment on Pharmacokinetics and Toxicity in Chemotherapy-Naive Metastatic Colorectal Cancer Patients," J Clin Oncol. 19(15):3456-62 (2001).
Fannon M, et al., "Sucrose Octasulfate Regulates Fibroblast Growth Factor-2 Binding, Transport, and Activity: Potential for Regulation of Tumor Growth," J Cell Physiol. 215(2):434-41 (2008), NIH public access author manuscript version, 19 pages.
Farncombe M, "Management of Bleeding in a Patient with Colorectal Cancer: A Case Study," Support Care Cancer. 1(3):159-160 (1993).
FDA, "Draft Guidance on Daunorubicin Citrate," Jul. 2014, 6 pages.
FDA, "Draft Guidance on Doxorubicin Hydrochloride," Recommended Feb. 2010, Revised Nov. 2013, Dec. 2014, 6 pages.

Fioravanti A, et. al., "Metronomic 5-Fluorouracil, Oxaliplatin and Irinotecan in Colorectal Cancer," Eur J Pharmacol. 519(1-3): 8-14 (2009).
Fleming G, et. al., "Phase I and Pharmacokinetic Study of 24-Hour Infusion 5-Fluorouracil and Leucovorin in Patients With Organ Dysfunction," Ann Oncol. 14(7):1142-7 (2003).
Freise C, et al., "Characterization of a Cyclosporine-Containing Liposome," Transplant Proc. 23(1 Pt 1):473-4 (1991).
Freise C, et al., "Increased Efficacy of Cyclosporin Liposomes in a Rat Orthotopic Liver Transplant Model," Surgical Forum. 43:395-7 (1992).
Freise C, et al., "The Increased Efficacy and Decreased Nephrotoxicity of a Cyclosporine Liposome," Transplantation. 57(6):928-932 (1994).
Gaber M, et al., "Thermosensitive Liposomes: Extravasation and Release of Contents in Tumor Microvascular Networks," Int J Radiat Oncol Biol Phys. 36(5)1177-87 (1996).
Gaber M, et al., "Thermosensitive Sterically Stabilized Liposomes: Formulation and in Vitro Studies on the Mechanism of Doxorubicin Release by Bovine Serum and Human Plasma," Pharm Res. 12(10):1407-16 (1995).
Garcia-Alfonso P, et. al., "Capecitabine in Combination with Irinotecan (XELIRI), Administered As a 2-Weekly Schedule, As First-Line Chemotherapy for Patients With Metastatic Colorectal Cancer: A Phase II Study of the Spanish GOTI Group," Br J Cancer. 101(7):1039-43 (2009).
Garcia-Carbonero R and Supko J, "Current Perspectives on the Clinical Experience, Pharmacology, and Continued Development of the Camptothecins," Clin Cancer Res. 8(3):641-61 (2002).
Garufi C, et. al., "A Phase II Study of Irinotecan Plus Chronomodulated Oxaliplatin, 5-Fluorouracil and Folinic Acid in Advanced Colorectal Cancer Patients," Br J Cancer 89(10):1870-5 (2003).
Geddie M, et al., "Improving the Developability of an Anti-EphA2 Single-Chain Variable Fragment for Nanoparticle Targeting," MAbs. 9(1):58-67 (2017). Epub 2016.
Gelmon K, et. al., "A Phase 1 Study of OSI-211 Given As an Intravenous Infusion Days 1, 2, and 3 Every Three Weeks in Patients With Solid Cancers," Invest New Drugs. 22(3):263-75 (2004).
Gemzar (gemcitabine HCI) package insert, revision Apr. 1998, 24 pages.
Giles F, et. al., "Phase I and Pharmacokinetic Study of a Low-Clearance, Unilamellar Liposomal Formulation of Lurtotecan, a Topoisomerase 1 Inhibitor, in Patients with Advanced Leukemia," Cancer. 100(7):1149-58 (2004).
Glimelius B, et. al., "A Randomized Phase III Multicenter Trial Comparing Irinotecan in Combination With the Nordic Bolus 5-Fu and Folinic Acid Schedule or the Bolus/Infused de Gramont Schedule (Lv5FU2) in Patients With Metastatic Colorectal Cancer," Ann Oncol. 19(5):909-14 (2008).
Glimelius B, et. al., "Prediction of Irinotecan and 5-Fluorouracil Toxicity and Response in Patients With Advanced Colorectal Cancer," Pharmacogenomics J. 11(1):61-71 (2011). Epub 2010.
Goldberg R, et. al., "A Randomized Controlled Trial of Fluorouracil Plus Leucovorin, Irinotecan, and Oxaliplatin Combinations in Patients With Previously Untreated Metastatic Colorectal Cancer," J Clin Oncol. 22(1):23-30 (2004). Epub 2003.
Greiner P, et. al., "Pharmacokinetics of (-)-Folinic Acid After Oral and Intravenous Administration of the Racemate," Br J Clin Pharmacol. 28(3):289-95 (1989).
Guichard S, et. al., "Cellular Interactions of 5-Fluorouracil and the Camptothecin Analogue CPT-11 (Irinotecan) in a Human Colorectal Carcinoma Cell Line," Biochem Pharmacol. 55(5):667-76 (1998).
Guichard S, et. al., "Sequence-Dependent Activity of the Irinotecan-5FU Combination in Human Colon-Cancer Model HT-29 In Vitro and In Vivo," Int J Cancer. 73(5):729-34 (1997).
Han S, et al., Abstract ACTR-33. "A Phase I Study of Convection-Enhanced Delivery of Liposomal-Irinotecan Using Real-Time Imaging With Gadolinium In Patients With Recurrent High Grade Glioma," Neuro-Oncology. 18(Suppl_6): vi9 doi.org/10.1093/neuonc/now212.031 (2016).

(56) References Cited

OTHER PUBLICATIONS

Hare J, "Utilization of Liposomes in Combination Cancer Chemotherapy," PhD thesis, University of Alberta, Department of Pharmacology, 2011, 367 pages.

Harker-Murray P, et al., Abstract CT146. "Plasma Pharmacokinetics of Liposomal Irinotecan (nal-iri) in Pediatric Oncology Patients with Recurrent or Refractory Solid Tumors: South Plains Oncology Consortium Study 2012-001," In Proceedings of the American Association for Cancer Research Annual Meeting 2017; Apr. 1-5, 2017. Washington, DC. Cancer Res. 2017;77(13 Suppl):Abstract nr CT146, doi:10.1158/1538-7445.AM2017-CT146, 4 printed pages.

Hashimoto S, et al., "Depletion of Alveolar Macrophages Decreases Neutrophil Chemotaxis to Pseudomonas Airspace Infections," Am J Physiol. 270(5 Pt 1):L819-28 (1996).

Hay M, et. al., "Clinical Development Success Rates for Investigational Drugs," Nature Biotechnol. 32(1):40-51 (2014).

Hayes M, et al., "Genospheres: Self-Assembling Nucleic Acid-Lipid Nanoparticles Suitable for Targeted Gene Delivery," Gene Ther. 13(7):646-51 (2006).

Hayes M, et al., "Increased Target Specificity of Anti-HER2 Genospheres by Modification of Surface Charge and Degree of PEGylation," Mol Pharm. 3(6):726-36 (2006).

Hsu M and Juliano R, "Interactions of Liposomes With the Reticuloendothelial System. II: Nonspecific and Receptor-Mediated Uptake of Liposomes by Mouse Peritoneal Macrophages," Biochim Biophys Acta. 720(4):411-419 (1982).

Huang S, et al., "Liposomes and Hyperthermia in Mice: Increased Tumor Uptake and Therapeutic Efficacy of Doxorubicin in Sterically Stabilized Liposomes," Cancer Res. 54(8):2186-91 (1994).

Huang S, et al., "Light Microscopic Localization of Silver Enhanced Liposome-Entrapped Colloidal Gold in Mouse Tissues," Biochim Biophys Acta. 1069(1):117-21 (1991).

Huang S, et al., "Microscopic Localization of Sterically Stabilized Liposomes in Colon-Carcinoma Bearing Mice," Cancer Res. 52(19):5135-43 (1992).

Huang S, et. al., "Pharmacokinetics and Therapeutics of Sterically Stabilized Liposomes in Mice Bearing C-26 Colon Carcinoma," Cancer Res. 52(24):6774-81 (1992).

Hwang J, et. al., "Improving the Toxicity of Irinotecan/5-FU/Leucovorin: A 21-Day Schedule," Oncology. 17(9):37-43 (2003). Available at cancernetwork.com/view/improving-toxicity-irinotecan5-fu-leucovorin-21-day-schedule, 13 printed pages.

Ignatiadis M, et. al., "A Multicenter Phase II Study of Docetaxel in Combination with Gefitinib in Gemcitabine-Pretreated Patients with Advanced/Metastatic Pancreatic Cancer," Oncology. 71(3-4):159-63 (2006).

Immordino M, et al., "Stealth Liposomes: Review of the Basic Science, Rationale, and Clinical Applications, Existing and Potential," Int J Nanomedicine. 1(3):297-315 (2006).

Jones S, et. al., Abstract 2547. "Phase I and Pharmacokinetic (PK) Study of IHL-305 (Pegylated Liposomal Irinotecan) in Patients With Advanced Solid Tumors," J Clin Oncol. 27(15_suppl):2547 and Table 1 (2009), 6 printed pages.

Kalra A, et al., Abstract 2065. "Magnetic Resonance Imaging with an Iron Oxide Nanoparticle Demonstrates the Preclinical Feasibility of Predicting Intratumoral Uptake and Activity of MM-398, a Nanoliposomal Irinotecan (nal-IRI)." In Proceedings of the 105th Annual Meeting of the American Association for Cancer Research; Apr. 5-9, 2014, Cancer Res 2014;74(19 Suppl):Abstract nr 2065, doi:10.1158/1538-7445.AM2014-2065, 1 printed page.

Khapzory (levoleucovrin) package insert, revised Oct. 2018, accessed from accessdata.fda.gov/drugsaffda_docs/label/2018/211226s000Ib1_pdf, 9 pages.

Kirpotin D, et al., "Building and Characterizing Antibody-Targeted Lipidic Nanotherapeutics," Methods Enzymol. 502:139-66 (2012).

Kirpotin D, et al., "Targeting of Liposomes to Solid Tumors: The Case of Sterically Stabilized Anti-HER2 Immunoliposomes," J Liposome Res. 7:391-417 (1997).

Kirpotin D, et al., Chapter 4.7, "Targeting of Sterically Stabilized Liposomes to Cancers Overexpressing HER2/neu Proto-Oncogene," In Medical Applications of Liposomes, Lasic D and Papahadjopoulos D, eds., pp. 325-345 (1998).

Kline C, et. al., "Preliminary Observations Indicate Variable Patterns of Plasma 5-Fluorouracil (5-FU) Levels During Dose Optimization of Infusional 5-FU in Colorectal Cancer Patients," Cancer Biol Ther. 12(7):557-68 (2011).

Krauss W, et al., "Emerging Antibody-Based HER2 (ErbB2/neu) Therapeutics," Breast Dis. 11:113-24 (2000).

De Jong F, et al., "Effects of nal-IRI (MM-398; a Liposomal Formulation of Irinotecan) ± 5-Fluorouracil (5-FU) on Duality of Life (QoL) in NAPOLI-1: A Phase 3 Study in Patients With Metastatic Pancreatic Ductal Adenocarcinoma Previously Treated With Gemcitabine," Poster presented at the Australian Gastro-Intestinal Trials Group, 18th Annual Scientific Meeting, Melbourne, Australia, Sep. 14-16, 2016, 10 pages.

De Jong F, et al., Abstract. "Effects of nal-IRI (MM-398; a Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma (mPDAC) Previously Treated With Gemcitabine," Australian Gastro-Intestinal Trials Group, 18th Annual Scientific Meeting, Melbourne, Australia, Sep. 14-16, 2016, 2 pages.

Dean A, et al., "First-Line (1L) Liposomal Irinotecan + 5-Fluorouracil/Leucovorin (5-FU/LV) + Oxaliplatin (OX) in Patients With Locally Advanced or Metastatic Pancreatic Ductal Adenocarcinoma: Exploratory Subgroup Analyses of Survival by Changes in CA 19-9 Levels." Poster presented at the European Society for Medical Oncology (ESMO) Virtual Congress 2020, Sep. 19-21, 2020, 7 pages.

Dean A, et al., "First-Line Liposomal Irinotecan + 5-Fluorouracil/Leucovorin + Oxaliplatin in Patients With Pancreatic Ductal Adenocarcinoma: Results From a Phase 1/2 Study." Presentation presented at the Clinical Oncology Society of Australia (COSA): Virtual meeting, Nov. 11-13, 2020, 10 pages.

Dean A, et al., "NAPOLIS-3: An Open-Label, Randomized, Phase III Study of First-Line Liposomal Irinotecan + 5- Fluorouracil/Leucovorin + Oxaliplatin Versus nab-Paclitaxel + Gemcitabine in Patients With Metastatic Pancreatic Ductal Adenocarcinoma." Presentation presented at the Clinical Oncology Society of Australia (COSA): Virtual meeting, Nov. 11-13, 2020, 10 pages.

Dean A, et al., Abstract 1529P. "First-Line (1L) Liposomal Irinotecan + 5-Fluorouracil/Leucovorin (5-FU/LV) + Oxaliplatin (OX) in Patients With Locally Advanced or Metastatic Pancreatic Ductal Adenocarcinoma (mPDAC): Exploratory Subgroup Analyses of Survival by Changes in CA 19-9 Levels," Ann Oncol. 31(Suppl_4):S881-S897 10.1016/annondannonc285 (2020), 3 printed pages.

Dean A, et al., Abstract 222. "First-Line Liposomal Irinotecan + 5-Fluorouracil/Leucovorin + Oxaliplatin in Patients With Pancreatic Ductal Adenocarcinoma: Results From a Phase 1/2 Study," Asia-Pac J Clin Oncol. 16(Suppl. 3):118-119 (2020).

Dean A, et al., Abstract 407. "NAPOLI-3: An Open-Label, Randomized, Phase III Study of First-Line Liposomal Irinotecan + 5-Fluorouracil/Leucovorin + Oxaliplatin Versus nab-Paclitaxel + Gemcitabine in Patients With Metastatic Pancreatic Ductal Adenocarcinoma," Asia-Pac J Clin Oncol. 16(Suppl. 8):202-3 (2020).

Dean A, et al., Abstract 4111 "A Phase 1/2, Open-Label Dose-Escalation Study of Liposomal Irinotecan (nal-IRI) Plus 5- Fluorouracil/Leucovorin (5-FU/LV) and Oxaliplatin (OX) in Patients with Previously Untreated Metastatic Pancreatic cancer (mPAC)," J Clin Oncol. 36(15_Suppl):4111 10.1200/JC0.2018.36.15_suppl.4111 (2018), 1 page.

Dean A, et al., Abstract. "Expanded Analyses of NAPOLI-1: Phase 3 Study of MM-398 (nal-IRI), With or Without 5-Fluorouracil and Leucovorin (5-FU/LV), Versus 5-FU/LV, in Metastatic Pancreatic Cancer (mPAC) Previously Treated With Gemcitabine-Based Therapy," 18th Annual Scientific Meeting of the Australasian Gastro-Intestinal Trials Group (AGITG), Melbourne, Australia, Sep. 14-16, 2016, 2 pages.

Dean A, et al., Abstract. "Liposomal Irinotecan (nal-IRI, MM-398)-Containing Regimens Versus nab-Paclitaxel Plus Gemcitabine as First-Line Therapy in Patients With Metastatic Pancreatic Adenocarcinoma (mPAC): A Randomized, Open-Label Phase 2

(56) References Cited

OTHER PUBLICATIONS

Study," 18th Annual Scientific Meeting of the Australasian Gastro-Intestinal Trials Group (AGITG), Melbourne, Australia, Sep. 14-16, 2016, 2 pages.

Dieguez G, et al., "Real-World Rates of Hematologic Laboratory Abnormalities and Associated Cost Among Metastatic Pancreatic Cancer Therapeutic Regimens," Poster presented at the American Society of Clinical Oncology Gastrointestinal Cancers Symposium (ASCO GI), San Francisco, CA, Jan. 23-25, 2020, 6 pages.

Dieguez G, et al., Abstract 670. "Real-World Rates of Hematology Lab Abnormalities and Associated Cost Among Metastatic Pancreatic Cancer (mPC) Therapeutic Regimens," J Clin Oncol. 38(4_Suppl):670 DOI: 10.1200/ JC0.2020.38.4_suppl.670 (2020), 2 printed pages.

Doris J, et al., Abstract CT12. "The Cost of Adverse Events for FDA-Approved/NCCN Category 1 Treatments for Medicare Fee-For-Service (FFS) Patients With Metastatic Pancreatic Cancer: Focus on Liposomal Irinotecan-Based Regimens," Hematology Oncology Pharmacy Association (HOPA) Annual Conference, Mar. 11-14, 2020, available at eventscribe.com/2020/posters/HOPAahead/SplitViewer.asp?Pid=NjgONzA2NjU1NjE, (2020), 2 pages.

Figer A, et. al., "A Comparison of Two Dose Regimens in Pancreatic Cancer," J Chemother. 12(5):442-5 (2000).

Gaddy D, et al., "A Systematic Literature Review to Identify and Compare Clinical Trials Evaluating Novel Therapeutic Agents in Post-Gemcitabine Advanced Pancreatic Cancer Patients." Poster presented at the International Society for Pharmacoeconomics and Outcomes Research (ISPOR) 18th Annual European Congress, Milan, Italy, Nov. 7-11, 2015, 6 pages.

Gaddy D, et al., "Preclinical Anti-tumor Activity of Nanoliposomal Irinotecan (Nal-IRI, MM-398) Supports Utilization as a Foundation of Front-Line Pancreatic Cancer Regimens." Poster presented at the American Society of Clinical Oncology Gastrointestinal Cancers Symposium (ASCO GI), San Francisco, CA, Jan. 19-21, 2017, 5 pages.

Gaddy D, et al., Abstract 336. "Preclinical Antitumor Activity of Nanoliposomal Irinotecan (Nal-IRI, MM-398) and Utilization as a Foundation of Front-Line Pancreatic Cancer Regimens," J Clin Oncol. 35(4_Suppl):336 DOI: 10.2001 JC0.2017.35.4_suppl.336 (2017), 2 printed pages.

Gaddy D, et al., Abstract PCN29. "A Systematic Literature Review to Identify and Compare Clinical Trials Evaluating Novel Therapeutic Agents in Post-Gemcitabine Advanced Pancreatic Cancer," Value in Health. 18(7):A434 (2015).

Gebbia V, et al., "Second-Line Chemotherapy in Advanced Pancreatic Carcinoma: A Multicenter Survey of the Gruppo Oncologico Italia Meridionale on the Activity and Safety of the FOLFOX4 Regimen in Clinical Practice," Ann Oncol. 18(Suppl 6):vi124-7 (2007).

Gill S, et al., "Pancreox: A Randomized Phase III Study of Fluorouracil/Leucovorin With or Without Oxaliplatin for Second-Line Advanced Pancreatic Cancer in Patients Who Have Received Gemcitabine-Based Chemotherapy," J Clin Oncol. 34(32):3914-20 and Appendix (2016).

Glassman D, et al., "Nanoliposomal Irinotecan With Flurouracil for the Treatment of Advanced Pancreatic Cancer." Poster presented at the American Society of Clinical Oncology Gastrointestinal Cancers Symposium (ASCO GI), San Francisco, CA, Jan. 18-20, 2018, 7 pages.

Glassman D, et al., Abstract 471. "Nano-Liposomal Irinotecan and 5-FU/LV (N+F) for the Treatment of Advanced PDAC: Memorial Sloan Kettering (MSK) Single Cancer Center Evaluation," J Clin Oncol. 36(4_Suppl):471 DOI: 10.1200/JCO.2018.36.4_suppl.471 (2018), 2 printed pages.

Gounaris I, et. al., "Options for the Treatment of Gemcitabine-Resistant Advanced Pancreatic Cancer," JOP. J Pancreas (Online) 11(2):113-23 (2010).

Gourzoulidis G, et al., "The Cost-Effectiveness of Nanoliposomal Irinotecan and 5-Fluorouracil (5-FU)/Leucovorin (LV) for the Treatment of Patients With Metastatic Adenocarcinoma of Pancreas Who Have Progressed Following the Use of Gemcitabine-Related Therapies in Greece." Poster presented at the Virtual International Society for Pharmacoeconomics and Outcomes Research (ISPOR) European Congress, Milan, Italy, Nov. 16-19, 2020, 9 pages.

Gourzoulidis G, et al., Abstract PCN57. "The Cost-Effectiveness of Nanoliposomal Irinotecan and 5-Fluorouracil (5-FU)/Leucovorin (LV) for the Treatment of Patients With Metastatic Adenocarcinoma of Pancreas Who Have Progressed Following the Use of Gemcitabine-Related Therapies in Greece," Virtual International Society for Pharmacoeconomics and Outcomes Research (ISPOR) European Congress, Milan, Italy, Nov. 16-19, 2020, available at ispor.org/heor-resources/presentations-database/presentation/euro2020-3282/105175, 2 printed pages.

Haller D, "Chemotherapy for Advanced Pancreatic Cancer," Int J Radiat Oncol Biol Phys. 56(4 Suppl):16-23 (2003).

Hann B, et. al., Abstract 5648. "Lipidic Nanoparticle CPT-11 in a Bioluminescent Orthotopic Pancreas Cancer Model," Cancer Res. 67(9 Suppl):5648 (2007), 4 printed pages.

Heinemann V, et. al., "Randomized Phase III Trial of Gemcitabine Plus Cisplatin Compared With Gemcitabine Alone in Advanced Pancreatic Cancer," J Clin Oncol. 24(24):3946-52 (2006).

Herrera-Restrepo O, et al., "Budget Impact in the USA of Liposomal Irinotecan as a Post-Gemcitabine Treatment Option for Patients With Metastatic Pancreatic Adenocarcinoma (mPC)." Poster presented at the International Society for Pharmacoeconomics and Outcomes Research (ISPOR) Annual Meeting, New Orleans, LA, May 18-22, 2019, 12 pages.

Herrera-Restrepo O, et al., Abstract PCN80. "Budget Impact in the USA of Liposomal Irinotecan as a Post-Gemcitabine Treatment Option for Patients With Metastatic Pancreatic Adenocarcinoma (mPC)," Value in Health. 22 (Suppl 2):S70 (2019).

Hidalgo M, "Pancreatic Cancer," N Engl J Med. 362(17):1605-17 (2010).

Hirsch J, et al., "Comparing Total Cost of Care for Medicare Fee-For-Service Patients With Pancreatic Cancer, by chemotherapy Regimen." Poster presented at the American Society of Clinical Oncology Gastrointestinal Cancers Symposium (ASCO GI), San Francisco, CA, Jan. 23-25, 2020, 5 pages.

Hirsch J, et al., "Comparing Total Costs of Care for Medicare Fee-For-Service (FFS) Patients With Metastatic Jancreatic Cancer by Chemotherapy Regimen," Poster presented at the Academy of Managed Care Pharmacy, Nexus (AMCP, Nexus): virtual meeting, week of Oct. 19, 2020, 8 pages.

Hirsch J, et al., "The Cost of Adverse Events for FDA-Approved/NCCN Category 1 Treatments for Medicare Fee-For-Service (FFS) Patients With Metastatic Pancreatic Cancer." Poster presented at the Hematology Oncology Pharmacy Association (HOPA) Annual Conference, Tampa, FL, Mar. 11-14, 2020, 6 pages.

Hirsch J, et al., "The Cost of Adverse Events for FDA-Approved/NCCN Category 1 Treatments for Medicare Fee-For-Service Patients With Metastatic Pancreatic Cancer." Poster presented at the American Society of Health-System Pharmacists (ASHP) Midyear 2019 Clinical Meeting and Exhibition, Las Vegas, NV, Dec. 8-12, 2019, 6 pages.

Hirsch J, et al., Abstract 4-138. "The Cost of Adverse Events for FDA-Approved/NCCN Category 1 Treatments for Medicare Fee-For-Service Patients With Metastatic Pancreatic Cancer," American Society of Health-System Pharmacists (ASHP) Midyear Clinical Meeting Professional Poster Abstracts, (2019), 2 pages.

Hirsch J, et al., Abstract 721. "Comparing Total Cost of Care for Medicare FFS Patients With Pancreatic Cancer by Chemotherapy Regimen," J Clin Oncol. 38(4_Suppl):721 DOI: 10.1200/JCO.2020.38.4_suppl.721 (2020), 2 printed pages.

Hirsch J, et al., Abstract e19394. "Comparing Total Cost of Care for Medicare FFS Patients With Pancreatic Cancer by Chemotherapy Regimen," J Clin Oncol. 38(15_Suppl):e19394 DOI: 10.1200/JC0.2020.38.15_suppl.e19394 (2020), 2 printed pages.

Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated With Gemcitabine," Presentation presented at the

(56) References Cited

OTHER PUBLICATIONS

European Society for Medical Oncology (ESMO) World Congress on Gastrointestinal Cancer, Barcelona, Spain, Jun. 29-Jul. 2, 2016, 13 pages.

Hubner R, et al., "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone." Poster presented at the European Society for Medical Oncology (ESMO) Annual Congress, Madrid, Spain, Sep. 8-12, 2017, 5 pages.

Hubner R, et al., "Time Course of Selected Treatment-Emergent Adverse Events in NAPOLI-1: A Phase 3 Study of Liposomal Irinotecan (nal-IRI; MM-398) ± 5-Fluorouracil and Leucovorin (5-FU/LV) vs 5-FU/LV in Metastatic Pancreatic cancer Previously Treated With Gemcitabine-Based Therapy." Poster presented at the European Society for Medical Oncology (ESMO) Annual Congress, Copenhagen, Denmark, Oct. 7-11, 2016, 8 pages.

Hubner R, et al., Abstract 242P. "Effects of nal-IRI (MM-398) ± 5-Fluorouracil on Quality of Life (QoL) of Patients With Metastatic Pancreatic Ductal Adenocarcinoma (mPDAC) Previously Treated With Gemcitabine Based Therapy: Results From NAPOLI-1 ," Ann Oncol. 27(Supp_9):ix76 doi:10.1093 1annonc/mdw582 (2016).

Hubner R, et al., Abstract 3832. "Time Course of Selected Treatment Emergent Adverse Events (TEAES) in NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10_1093/annondmdw371 (2016), 4 printed pages.

Hubner R, et aL, Abstract 741P. "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone," Ann Oncol. 28(Suppl_5):253 loi:10.1093/annonc/mdx369 (2017).

Hubner R, et al., Abstract. "Expanded Analyses of NAPOLI-1: Phase 3 Study of nal-IRI (MM-398), With or Without 5-Fluorouracil (5FU) and Leucovorin (LV), Versus 5-Fluorouracil and Leucovorin (5FU/LV), in Metastatic Pancreatic Cancer (mPAC) Previously Treated With Gemcitabine-Based Therapy," 2015 National Cancer Research Institute (NCRI) Cancer Conference, Nov. 1-4, 2015, 2 printed pages.

Hwang J, et al., Abstract 4618. "A Randomized Phase II Study of FOLFOX or FOLFIRI.3 as Second-Line Therapy in Patients With Advanced Pancreatic Cancer Previously Treated With Gemcitabine-Based Chemotherapy," J Clin Oncol. 27(15_Suppl):4618 (2009), 2 printed pages.

Ignatius R, et al., "Presentation of Proteins Encapsulated in Sterically Stabilized Liposomes by Dendritic Cells Initiates CD8+ T-cell Responses in Vivo," Blood. 96(10)3505-13 (2000).

Ilson D, "Nanolipoosomal Irinotecan Effective for Pancreatic Cancer," NEJM journal Watch, available at jwatch.org/ la39795/2015/12/08/nanoliposomal-irinotecan-effective-pancreatic-cancer, (2015), 7 printed pages.

Ioka T, et al., "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)." Poster presented at the European Society for Medical Oncology (ESMO) Asia 2019 Congress, Singapore, Nov. 22-24, 2019, 9 pages.

Ioka T, et al., Abstract 132P. "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)," Ann Oncol. 30 (Suppl_9):ix47-ix48 doi:10.1093/annonc/mdz422 (2019).

Ioka T, et al., Abstract 274TiP. "A Randomized Phase 2 Study of Nanoliposomal Irinotecan (nal-IRI, BAX2398)-containing Regimen in Japanese Patients With Metastatic Pancreatic Adenocarcinoma (mPAC)," Ann Oncol. 27 (Supp_9):ix84-ix85 doi:10.1093/annonc/mdw582 (2016).

Jameson G, et al., "Adverse Events in Patients with Metastatic Pancreatic Cancer Receiving Liposomal Irinotecan: Understanding the Occurrence and How Management Affects Patient Outcomes." Poster presented at the Oncology Nursing Society (ONS) Annual Conference, Washington, DC, May 17-20, 2018, 7 pages.

Jameson G, et al., Abstract 1. "Adverse Events in Patients with Metastatic Pancreatic Cancer Receiving Liposomal Irinotecan: Understanding the Occurrence and How Management Affects Patient Outcomes," Oncology Nursing Society (ONS) 43rd Annual Congress, available at ons.confex_com/ons/2018/meetingapp.cgi/Paper/2970, (2018), 2 pages.

Kang S and Saif M, "Optimal Second Line Treatment Options for Gemcitabine Refractory Advanced Pancreatic Cancer Patients. Can We Establish Standard of Care with Available Data?," JOP. J Pancreas (Online) 9(2):83-90 :2008).

Katopodis O, et. al., "Second-Line Chemotherapy With Capecitabine (Xeloda) and Docetaxel (Taxotere) in Previously Treated, Unresectable Adenocarcinoma of Pancreas: The Final Results of a Phase II Trial," Cancer Chemother Pharmacol. 67(2):361-8 (2011). Epub 2010.

Kim G, et al., "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens." Poster presented at the European Society for Medical Oncology (ESMO) Virtual Congress 2020, Sep. 19-21, 2020, 6 pages.

Kim G, et al., "Impact of Treatment Sequence on Overall Survival in Metastatic Pancreatic Cancer Patients Treated with Liposomal Irinotecan in the Real-World Setting." Poster presented at the Hematology Oncology Pharmacy Association (HOPA) Annual Conference, Tampa, FL, Mar. 11-14, 2020, 7 pages.

Kim G, et al., Abstract 1564R "Clinical Pathway Implications and Real-World Characteristics and Outcomes for Patients With Metastatic Pancreatic Ductal Adenocarcinoma (mPDAC) Treated With First Line Category 1 National comprehensive Cancer Network (NCCN) Regimens," Ann Oncol. 31(Suppl_4):S881-S897 10.1016/annonc./annonc285 (2020), 2 printed pages.

Kim G, et al., Abstract e16740. "Real-World Use of Liposomal Irinotecan-Based Regimens Among Patients (pts) With Metastatic Pancreatic Adenocarcinoma (mPDAC) in the United States (U.S.)," J Clin Oncol. 38(15_Suppl):e16740 DOI: 10.1200/JC0.2020.38.15_suppl.e16740 (2020), 2 printed pages.

Kim H, et. al., "Phase II Study of Palliative S-1 in Combination With Cisplatin as Second-Line Chemotherapy for Gemcitabine-Refractory Pancreatic Cancer Patients," Oncol Lett. 3(6):1314-8 (2012).

Kim Y, et. al., "Phase II Study of 5-Fluorouracil and Paclitaxel in Patients With Gemcitabine-Refractory Pancreatic Cancer," Cancer Chemother Pharmacol. 63(3):529-33 (2009). Epub 2008.

Kindler H, et. al., "Arsenic Trioxide in Patients With Adenocarcinoma of the Pancreas Refractory to Gemcitabine: A Phase II Trial of the University of Chicago Phase II Consortium," Am J Clin Oncol. 31(6):553-6 (2008).

Kindler H, et. al., "Gemcitabine Plus Bevacizumab Compared With Gemcitabine Plus Placebo in Patients With Advanced Pancreatic Cancer: Phase III Trial of the Cancer and Leukemia Group B (CALGB 80303)," J Clin Oncol. 28 (22):3617-22 (2010).

Kipps E, et. al., "Liposomal Irinotecan in Gemcitabine-Refractory Metastatic Pancreatic Cancer: Efficacy, Safety and Place in Therapy," Ther Adv Med Oncol. 9(3):159-70 (2017).

Klapdor R and Fenner C, "Irinotecan(Campto R): Efficacy as Third/Forth Line Therapy in Advanced Pancreatic Cancer," Anticancer Res. 20(6D): 5209-12 (2000).

Klapdor R, et. al., "Reflections on Treatment Strategies for Palliative Chemotherapy of Pancreatic Cancer," Anticancer Res. 27(4A): 1789-94 (2007).

Klinz S, et al., Abstract e16205. "DNA Ddamage With Liposomal Irinotecan (nal-IRI) in Pancreatic Cancer Xenografts: Multimodal Analysis of Deposition Characteristics," J Clin Oncol. 36(15_Suppl):e16205 DOI: 10.1200/ JCO.2018.36.15_suppl.e16205 (2018), 2 printed pages.

(56) References Cited

OTHER PUBLICATIONS

KO A, et. al., "A Phase II Study of Bevacizumab Plus Erlotinib for Gemcitabine-Refractory Metastatic Pancreatic Cancer," Cancer Chemother Pharmacol. 66(6):1051-7 (2010).

Koeller J, et al., Abstract e16751. "Trends in Real-World Clinical Outcomes Among Patients (pts) With Metastatic Pancreatic Adenocarcinoma (mPDAC) Treated With Liposomal Irinotecan Based Regimens in the United States (US)," J Clin Oncol. 38(15_Suppl):e16751 DOI: 10.1200/JC0.2020.38.15_suppl.e16751 (2020), 2 printed pages.

Kulke M, et. al., "Capecitabine Plus Erlotinib in Gemcitabine-Refractory Advanced Pancreatic Cancer," J Clin Oncol. 25(30):4787-92 (2007).

Kulke M, et. al., "Randomized Phase II Study of Gemcitabine Administered at a Fixed Dose Rate or in Combination With Cisplatin, Docetaxel, or Irinotecan in Patients With Metastatic Pancreatic Cancer: CALGB 89904," J Clin Oncol. 27(33):5506-12 (2009).

Lakatos G, et al., "Prognostic Value of Baseline Biliary Stents on Outcomes in Patients With Metastatic Pancreatic Ductal Adenocarcinoma (mPDAC) in the NAPOLI-1 Trial." Poster presented at the European Society for Medical Oncology 20th World Congress on Gastrointestinal Cancer, Barcelona, Spain, Jun. 20-23, 2018, 10 pages.

Lakatos G, et al., Abstract P-151. "Prognostic Value of Baseline Biliary Stents on Outcomes in Patients With Metastatic Pancreatic Ductal Adenocarcinoma (mPDAC) in the NAPOLI-1 Trial," Ann Oncol. 29(Suppl_5):v42 doi:10.1093/annonc/mdy151 (2018).

Latimer H, et al., Abstract C5. "Utilization of Hospital Inpatient Services Among Patients With Metastatic Pancreatic Cancer With Commercial and Medicare Insurance Treated With FDA-Approved/NCCN Category 1 Regimens," J Manag Care Spec Pharm. 26(10-a):S20 (2020).

LE A, et.al., "Conceptual Framework for Cutting the Pancreatic Cancer Fuel Supply," Clin Cancer Res. 18 (16):4285-90 (2012).

Lee K, et al., Abstract P-153. "Decreased Appetite (DA) at Baseline Impacts Prognosis in the NAPOLIS-1 Phase 3 Study in Metastatic Pancreatic Ductal Adenocarcinoma (mPDAC)," Ann Oncol. 29(Suppl_5):v42-v43 doi:10.1093/ annonc/mdy151 (2018).

Lee K-H, et al., "Decreased Appetite (DA) at Baseline Impacts Prognosis in the NAPOLI-1 Phase 3 Study in Metastatic Pancreatic Ductal Adenocarcinoma (mPDAC)." Poster presented at the European Society for Medical Oncology 20th World Congress on Gastrointestinal Cancer, Barcelona, Spain, Jun. 20-23, 2018, 9 pages.

Leonard S, et al., "Deposition Characteristics and Resulting DNA Damage Patterns of Liposomal Irinotecan (nal-IRI) in Pancreatic Cancer Xenografts." Poster presented at the American Society of Clinical Oncology Gastrointestinal cancers Symposium (ASCO GI), San Francisco, CA, Jan. 18-20, 2018, 9 pages.

Leonard S, et al., Abstract 335. "Deposition Characteristics and Resulting DNA Damage Patterns of Liposomal rinotecan (nal-IRI) in Pancreatic Cancer Xenografts," J Clin Oncol. 36(4_Suppl):335 DOI: 10.1200/JCO.2018.36.4_suppl.335 (2018), 2 printed pages.

Li J and Saif M, "Any Progress in the Management of Advanced Pancreatic Cancer? Highlights from the 45th ASCO Annual Meeting." JOP. J Pancreas (Online) 10(4):361-5 (2009).

Li J, et al.' "Any Second-Line Therapy for Advanced Pancreatic Cancer? Highlights from the 2010 ASCO Gastrointestinal Cancers Symposium." JOP. J Pancreas (Online). 11(2):151-3 (2010).

Löhr J, et. al., "Cationic Liposomal Paclitaxel Plus Gemcitabine or Gemcitabine Alone in Patients With Advanced Pancreatic Cancer: a Randomized Controlled Phase II Trial," Ann Oncology. 23(5):1214-22 (2012). Epub 2011.

Ma W, et al., Abstract 2365. "Nanoliposomal Irinotecan (MM-398, nal-IRI) Population Pharmacokinetics (PK) and its Association With Efficacy and Safety in Patients With Solid Tumors Based on the Phase 3 Study NAPOLI-1 and Five Phase 1 and 2 Studies," Eur J Cancer. 51(3):S458 10.1016/S0959-8049(16)31281-3 (2015).

Macarulla MercadéT, et al., "NAPOLI-1 Phase 3 Trial Outcomes by Prior Surgery, and Disease Stage, in Patients With Metastatic Pancreatic Ductal Adenocarcinoma (mPDAC)." Poster presented at the European Society for Medical Oncology Annual Congress, Munich, Germany, Oct. 19-23, 2018, 7 pages.

Macarulla MercadéT, et al., "Prognostic Effect of Primary Tumour Location in the NAPOLI-1 Phase 3 Study in Metastatic Pancreatic Ductal Adenocarcinoma (mPDAC)." Poster presented at the European Society for Medical oncology 19th World Congress on Gastrointestinal Cancer, Barcelona, Spain, Jun. 20-23, 2018, 10 pages.

Macarulla Mercadé T, et al., "Selected Subgroup Analyses of Liposomal Irinotecan in Patients With Metastatic Pancreatic Ductal Adenocarcinoma in the Global NAPOLI-1 Phase III Trial." Presentation presented at the European Society for Medical Oncology (ESMO) 20th World Congress on Gastrointestinal Cancer, Barcelona, Spain, Jun. 20-23, 2018, 16 pages.

Macarulla Mercadé T, et al., "Subgroup Analysis by Baseline Pain Intensity (BPI) and Baseline Analgesic Use (BAU) in NAPOLI-1, A phase 3 Study of Liposomal Irinotecan (nal IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 8 pages.

Macarulla Mercadé T, et al., "Subgroup Analysis by Baseline Weight-Associated Parameters: A phase 3 Study of Liposomal Irinotecan (nal-IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of clinical Oncology Gastrointestinal Cancers Symposium (ASCO GI), San Francisco, CA, Jan. 18-20, 2018, 7 pages.

Macarulla MercadéT, et al., "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy." Poster presented at the European Society for Medical Oncology 20th World Congress on Gastrointestinal Cancer, Barcelona, Spain, Jun. 20-23, 2018, 10 pages.

Macarulla MercadéT, et al., Abstract 379. "Subgroup Analysis by Baseline Pain Intensity (BPI) and Analgesic Use (BAU) in NAPOLI-1: A phase III Study of Liposomal Irinotecan (nal IRI)±5-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):379 DOI: 10.1200/JCO.2018.36.4_suppl.379 (2018), 4 printed pages.

Macarulla MercadéT, et al., Abstract 410. "Subgroup Analysis by Baseline (BL) Weight-Associated Parameters: A phase III Study of Liposomal Irinotecan (nal-IRI)±5-FluorouracilILeucovorin (5-FU/LV) in Patients (pts) With Metastatic Pancreatic Ductal Adenocarcinoma (mPDAC) Previously Treated With Gemcitabine-Based (Gem) Therapy," J Clin Oncol. 36(4_Suppl):410 DOI: 10.1200/JC0.2018.36.4_suppl.410 (2018), 6 printed pages.

Macarulla MercadéT, et al., Abstract 733P. "NAPOLI-1 Phase III Trial Outcomes by Prior Surgery, and Disease Stage, in Patients With Metastatic Pancreatic Ductal Adenocarcinoma (mPDAC)," Ann Oncol. 29(Supp_8)viii249-riii250 doi:10_1093/annondmdy282 (2018).

Macarulla MercadéT, et al., Abstract O-004. "Selected Subgroup Analyses of Liposomal Irinotecan (nal-IRI) in Patients With Metastatic Pancreatic Ductal Adenocarcinoma (mPDAC) in the Global NAPOLI-1 Phase III Trial," Ann Oncol. 29(Suppl_5)v101 doi:10.1093/annondmdy149 (2018).

Macarulla MercadéT, et al., Abstract P-150. "Prognostic Effect of Primary Tumour Location in the NAPOLI-1 Phase 3 Study in Metastatic Pancreatic Ductal Adenocarcinoma (mPDAC)," Ann Oncol. 29(Suppl_5)v41-v42 doi:10.1093/annonc/mdy151 (2018).

Macarulla MercadéT, et al., Abstract P-152. "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy," Ann Oncol. 29(Suppl_5):v42 doi:10.1093/annonc/mdy151 (2018).

Macarulla T, et al., "Integrated Population Pharmacokinetic Modelling of Liposomal Irinotecan in Patients With Various Tumour

(56) References Cited

OTHER PUBLICATIONS

Types, Including Untreated Metastatic Pancreatic Cancer (mPC)." Poster presented at the European Society for Medical Oncology (ES,P) Congress 2019, Barcelona, Spain, Sep. 27-Oct. 1, 2019, 6 pages.
Macarulla T, et al., "Subgroup Analysis by Prior Lines of Metastatic Therapy in NAPOLI-1, A Global, Randomized Phase 3 Study of Liposomal Irinotecan ± 5-Fluorouracil and Leucovorin, vs. 5-Fluorouracil and Leucovorin in Patients With Metastatic Pancreatic Ductal Adenocarcinoma Who Have Progressed Following Gemcitabine-Based Therapy." Poster presented at the American Society of Clinical Oncology (ASCO) Annual Conference, Chicago, IL, Jun. 2-6, 2017, 7 pages.
Macarulla T, et al., Abstract 4127. "Subgroup Analysis by Prior Lines of Metastatic Therapy (mtx) in NAPOLI-1: A Global, Randomized Phase 3 Study of Liposomal Irinotecan (nal-IRI) ± 5-Fluorouracil and Leucovorin (5-FU/LV), vs. 5-FU/LV in Patients (pts) With Metastatic Pancreatic Ductal Adenocarcinoma (mPDAC) Who Have Progressed 7ollowing Gemcitabine-Based Therapy," J Clin Oncol. 35(15_Suppl):4127 DOI: 10.1200/JC0.2017.35.15_supplA127 2017), 2 printed pages.
Macarulla T, et al., Abstract 691P. "Integrated Population Pharmacokinetic Modelling of Liposomal Irinotecan in Patients With Various Tumour Types, Including Untreated Metastatic Pancreatic Cancer (mPC)," Ann Oncol. 30 (Suppl_5):v263 doi:10.1093/annonc,/mdz247 (2019).
Kraut E, et. al., Abstract 2017. "Final Results of a Phase I Study of Liposome Encapsulated SN-38 (LE-SN38): Safety, Pharmacogenomics, Pharmacokinetics, and Tumor Response," J Clin Oncol. 23(16_Suppl):2017 (2005), 3 printed pages.
Kulke M, et. al., "A Phase II Trial of Irinotecan and Cisplatin in Patients with Metastatic Neuroendocrine Tumors," Dig its Sci. 51(6):1033-8 (2006).
Lamichhane N, et. al., "Liposomes: Clinical Applications and Potential for Image-Guided Drug Delivery," Molecules. 23(2):288 doi: 10.3390/molecules2302028 (2018), 17 pages.
Larsen A, et al., "Influence of Liposomal Irinotecan (nal-IRI) and Non-Liposomal Irinotecan, Alone and in combination, on Tumor Growth and Angiogenesis in Colorectal Cancer (CRC) Models." Poster presented at the American Society of Clinical Oncology Gastrointestinal Cancers Symposium (ASCO GI), San Francisco, CA, Jan. 18-20, 2018, 9 pages.
Larsen A, et al., Abstract 771 "Influence of Liposomal Irinotecan (nal-IRI) and Non-Liposomal Irinotecan, Alone and in Combination, on Tumor Growth and Angiogenesis in Colorectal Cancer (CRC) Models," J Clin Oncol. 36 (4_Suppl):711 DOI: 10.1200/JC0.2018.36.4_supp1.711 (2018), 2 printed pages.
Lecovorin Calcium package insert, Teva, revised Oct. 2009, 6 pages.
Lee H, et al., "(64)Cu-MM-302 Positron Emission Tomography Quantifies Variability of Enhanced Permeability and Retention of Nanoparticles in Relation to Treatment Response in Patients with Metastatic Breast Cancer," Clin Cancer Res. 23(15):4190-4202 (2017).
Lee H, et al., "A Gradient-Loadable (64)Cu-Chelator for Quantifying Tumor Deposition Kinetics of Nanoliposomal Therapeutics by Positron Emission Tomography," Nanomedicine. 11(1):155-65 (2015). Epub 2014.
Liu B, et al., "Mapping Tumor Epitope Space by Direct Selection of Single-Chain Fv Antibody Libraries on Prostate Cancer Cells," Cancer Res. 64(2):704-10 (2004).
Liu et al. "Recombinant Full-Length Human IgGis Targeting Hormone-Refractory Prostate Cancer," J Mol Med (Berl). 85(10):1113-23 (2007).
Liu J-J, et al. "Simple and Efficient Liposomal Encapsulation of Topotecan by Ammonium Sulfate Gradient: Stability, Pharmacokinetic and Therapeutic Evaluation," Anticancer Drugs. 13(7):709-17 (2002).
Lundberg B, et al., "Conjugation of Apolipoprotein B with Liposomes and Targeting to Cells in Culture," Biochim Biophys Acta. 1149(2):305-12 (1993).

Ma W, et al., Abstract e13588. "Population Pharmacokinetics and Exposure-Safety Relationship of Nanoliposomal Irinotecan (MM-398, nal-IRI) In Patients With Solid Tumors," J Clin Oncol. 33(15_Suppl):e13588 DOI: 10.1200/ c,o.2015.33.15_suppl.e13588 (2015), 2 printed pages.
Mabro M, et. al., "A Phase II Study of FOLFIRI-3 (Double Infusion of Irinotecan Combined With LV5FU) After FOLFOX in Advanced Colorectal Cancer Patients," Br J Cancer. 94(9):1287-92 (2006).
Mabro M, et. al., "Bimonthly Leucovorin, Infusion 5-Fluorouracil, Hydroxyurea, and Irinotecan (FOLFIRI-2) for Pretreated Metastatic Colorectal Cancer," Am J Clin Oncol. 26(3):254-8 (2003).
Mackenzie M, et. al., "A Phase I Study of OSI-211 and Cisplatin as Intravenous Infusions Given on Days 1, 2 and 3 Every 3 Weeks in Patients With Solid Cancers," Ann Oncol. 15(4):665-70 (2004).
Malet-Martino M and Martino R, "Clinical Studies of Three Oral Prodrugs of 5-Fluorouracil (Capecitabine, UFT, S-1): A Review," Oncologist. 7(4):288-323 (2002).
Mamot C, et al. "Epidermal Growth Factor Receptor (EGFR)-Targeted Immunoliposomes Mediate Specific and Efficient Drug Delivery to EGFR- and EGFRvIII-Overexpressing Tumor Cells," Cancer Res. 63(12):3154-61 (2003).
Mamot C, et al., "Liposome-Based Approaches to Overcome Anticancer Drug Resistance," Drug Resist Updat. 6 (5)271-9 (2003).
Mancini R and Modlin J, "Chemotherapy Administration Sequence: A Review of the Literature and Creation of a Sequencing Chart," J Hematol Oncol Pharm. 1(1):17-25 (2011).
Martin L, et. al., "VEGF Remains an Interesting Target in Advanced Cancreas Cancer (APCA): Results of a Multi-institutional Phase II Study of Bevacizumab, Gemcitabine, and Infusional 5-Fluorouracil in Patients With APCA," Ann Oncol. 23(11):2812-20 (2012).
Mathijssen R, et. al., "Clinical Pharmacokinetics and Metabolism of Irinotecan (CPT-11)," Clin Cancer Res. 7 (8)2182-94 (2001).
Matsusaka S, et. al., "Differential Effects of Two Fluorouracil Administration Regimens for Colorectal Cancer," Oncol Rep. 10(1):109-13 (2003).
Mayer L, et. al.,"Ratiometric Dosing of Anticancer Drug Combinations: Controlling Drug Ratios After Systemic Administration Regulates Therapeutic Activity in Tumor-Bearing Mice," Mol Cancer Ther. 5(7):1854-63 (2006).
McNamara M, et al., "NET-02: A Multi-Centre, Randomized, Phase II Trial of Liposomal Irinotecan (nal-IRI) and 5-Fluorouracil (5-FU)/ Folinic Acid or Docetaxel as Second-Line Therapy in Patients (pts) With Progressive Poorly Differentiated Extra-Pulmonary Neuroendocrine Carcinoma (PD-EP-NEC)." Poster presented at the 17th Annual European Neuroendocrine Tumor Society (ENETS) Conference for the Diagnosis and Treatment of Neuroendocrine Tumor Disease, Virtual Conference, Mar. 11-13, 2020, 4 pages.
McNamara M, et al., Abstract PO4. "NET-02: A Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-pulmonary Neuroendocrine Carcinoma (PD-EP-NEC)," in Abstracts of the 17th Annual European Neuroendocrine Tumor Society (ENETS) Conference for the Diagnosis and Treatment of Neuroendocrine Tumor Disease, Virtual Conference, Mar. 11-13, 2020, p. 374.
Meerum Terwogt J, et. al., "Phase I and Pharmacokinetic Study of SPI-77, a Liposomal Encapsulated Dosage Form of Cisplatin," Cancer Chemother Pharmacol. 49(3):201-10 (2002).
Messerer C, et. al., "Liposomal Encapsulation of Irinotecan and Potential for the Use of Liposomal Drug in the Treatment of Liver Metastases Associated with Advanced Colorectal Cancer," MS Thesis, University of British Columbia, 2000, 90 pages.
Munzone E, "Adverse Side Effects Associated to Metronomic Chemotherapy," Presentation presented at Aiom Cancer Metronomic Therapy, Feb. 26, 2016, Milan, 32 pages.
Myocet liposomal, Summary of product characteristics and labelling and package leaflet, European Medicines Agency, available at ema.europa.eu/en/documents/product-informationimyocet-liposomal-previously-myocet-epar-product-nformation_en.pdf, Date of first authorisation: Jul. 13, 2000, Date of latest renewal: Jul. 2, 2010, 37 pages.
Nakajima T, et. al., "Synergistic Antitumor Activity of the Novel SN-38-Incorporating Polymeric Micelles, NK012, combined With

(56) References Cited

OTHER PUBLICATIONS

5-Fluorouracil in a Mouse Model of Colorectal Cancer, As Compared With That of Irinotecan Plus 5-fluorouracil," Int J Cancer. 122(9):2148-53 (2008).
Nardi M, et. al., Abstract 14520. "Metronomic Irinotecan and Standard FOLFIRI Regimen as First-Line Chemotherapy in Metastatic Colorectal Cancer (MCRC). Final Results of Phase II Study," J Clin Oncol. 25(18_suppl):14520 (2007), 1 printed page.
National Cancer Institute, "Irinotecan Hydrochloride Liposome,"Posted: Oct. 27, 2015, Updated:Mar. 28, 2019, available at cancer.gov/about-cancer/treatment/drugshrinotecan-hydrochloride-liposome, 2 pages.
Noble C, et al, "Development of Ligand-Targeted Liposomes for Cancer Therapy," Expert Opin Ther Targets. 8 (4):335-53 (2004).
Noordhuis P, et. al., "5-Fluorouracil Incorporation into RNA and DNA in Relation to Thymidylate Synthase Inhibition of Human Colorectal Cancers," Ann Oncol. 15(7):1025-32 (2004).
Ogata Y, et. al., "Dosage Escalation Study of S-1 and Irinotecan in Metronomic Chemotherapy against Advanced colorectal Cancer," Kurume Med J. 56(1-2):1-7 (2009).
Oncology News International, "Experts Debate Bolus vs Continuous Infusion 5-FU." Feb. 1, 2003, vol. 12, Issue 2, 3 printed pages.
O'Reilly S, "Topotecan: What Dose, What Schedule, What Route'?" Clin Cancer Res. 5(1):3-5 (1999).
Pal A, et. al., "Preclinical Safety, Pharmacokinetics and Antitumor Efficacy Profile of Liposome-Entrapped SN-38 Formulation," Anticancer Res. 25(1A):331-41 (2005).
Papahadjopoulos D, et al., "Targeting of Drugs to Solid Tumors Using Anti-HER2 Immunoliposomes," J Liposome Res. 8(4):425-42 (1998).
Papahadjopoulos D, et. al., "Sterically Stabilized Liposomes: Improvements in Pharmacokinetics and Antitumor Therapeutic Efficacy," Proc Natl Acad Sci USA. 88(24):11460-4 (1991).
Papi M, et. al., "Clinically Approved PEGylated Nanoparticles Are Covered by a Protein Corona That Boosts the Uptake by Cancer Cells," Nanoscale. 9(29):10327-34 (2017).
Park J, et al., "Anti-HER2 Immunoliposomes for Targeted Therapy of Human Tumors," Cancer Lett. 118(2):153-60 :1997).
Park J, et al., "Development of Anti-p185HER2 Immunoliposomes for Cancer Therapy," Proc Natl Acad Sci U S A. 92 (5):1327-31 (1995).
Park J, et al., "Immunoliposomes for Cancer Treatment," Adv Pharmacol. 40:399-435 (1997).
Park J, et al., "Sterically Stabilized Immunoliposomes: Formulations for Delivery of Drugs and Genes to Tumor Cells In Vivo," In Targeting of Drugs 6: Strategies for Stealth Therapeutic Systems, Gregoriadis G, et al., eds., Plenum Press, New York, pp. 41-47 (1998).
Park J, et al., "Tumor Targeting Using Anti-HER2 Immunoliposomes," J Control Release. 74(1-3):95-113 (2001).
Park J, el al., "Anti-HER2 Immunoliposomes for Targeted Drug Delivery," Med Chem Res. 8(718):383-91 (1998).
Patankar N, et. al., "Topophore C: A Liposomal Nanoparticle Formulation of Topotecan for Treatment of Ovarian Cancer," Invest New Drugs. 31(1):46-58 (2013). Epub 2012.
Patel M, et al., "Effects of Oxaliplatin and CPT-11 on Cytotoxicity and Nucleic Acid Incorporation of the Fluoropyrimidines," J Cancer Res Clin Oncol. 130(8):453-9 (2004).
Yang, et_ al., "Oxaliplatin Long-Circulating Liposomes Improved Therapeutic Index of Colorectal Carcinoma," BMC Biotechnology. 11:21 doi: 10.1186/1472-6750-11-21 (2011), 8 pages.
Yoo C, et al., "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): Nifty Trial." Poster presented at the European Society for Medical Oncology (ESMO) 2019 Congress, Barcelona, Spain, Sep. 27-Oct. 1, 2019, 6 pages.
Yoo C, et al., Abstract 829TiP. "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): Nifty Trial," Ann Oncol. 30(Supp_5):v318 /doi.org/10.1093/ annondmdz247.155 (2019).
Younis I, et. al., "Enterohepatic Recirculation Model of Irinotecan (CPT-11) and Metabolite Pharmacokinetics in Patients With Glioma," Cancer Chemother Pharmacol. 63(3):517-24 (2009), author manuscript version, 16 pages.
Zamboni W, et. al., "Phase I and Pharmacokinetic Study of Pegylated Liposomal CKD-602 in Patients with Advanced Malignancies," Clin Cancer Res. 15(4):1466-72 (2009) and correction found at Clin Cancer Res. 15(8):2949-50 (2009).
Zhang K, et aL, "Comprehensive Optimization of a Single-Chain Variable Domain Antibody Fragment as a Targeting Ligand for a Cytotoxic Nanoparticle," MAbs. 7(1):42-52 (2015).
Markham C, et al., "A Phase Ii Irinotecan—Cisplatin Combination in Advanced Pancreatic Cancer," Br J Cancer. 89 (10):1860-4 (2003).
Matrisian , et. al., "The Past, Present, and Future of Pancreatic Cancer Clinical Trials," American Society of Clinical Oncology Educational Book. 35:e205-15 (2016).
Melisi D, et al., Abstract B04. "Effects of Nanoliposomal Irinotecan (nal-IRI; MM-398) ± 5-Fluorouracil and Leucavorin (5-FU/LV) on Quality of Life (QoL) in Patients (pts) With Metastatic Pancreatic Adenocarcinoma (mPAC) Previously Treated With Gemcitabine-Based Therapy: Results From the Phase 3 NAPOLI-1 Study," Ann Oncol. 27(Supp_4):iv18 doi:10.1093/annoncirndw333.4 (2016).
Moore M, et. al., "Erlotinib Plus Gemcitabine Compared With Gemcitabine Alone in Patients With Advanced Pancreatic Cancer: A Phase III Trial of the National Cancer Institute of Canada Clinical Trials Group," J Clin Oncol. 25 (15):1960-6 (2007).
Muldoon L, et al., "Comparing Service Utilization and Costs for Medicare FFS Patients With Metastatic Pancreatic cancer by Chemotherapy Regimen and Line of Therapy." Poster presented at the International Society for Pharmacoeconomics and Outcomes Research (ISPOR) Annual Meeting, New Orleans, LA, May 18-22, 2019, 6 pages.
Muldoon L, et al., Abstract e18357. "Treatment Patterns, Survival Rate, and Parts A and B Costs by Line of Therapy or FDA-Approved/NCCNCategory 1 Treatments for Patients With Metastatic Pancreatic Cancer," J Clin Oncol. 37 (15_Suppl):e18357 DOI: 10.1200/JC0.2019.37.15_suppl.e18357 (2019), 2 printed pages.
Muldoon L, et al., Abstract PCN302. "Comparing Service Utilization and Costs for Medicare FFS Patients With Metastatic Pancreatic Cancer by Chemotherapy Regimen and Line of Therapy," Value in Health. 22(Suppl 2):S113-114 (2019).
Nakai Y, et. al., "Inhibition of Renin—Angiotensin System Affects Prognosis of Advanced Pancreatic Cancer Receiving Gemcitabine," Br J Cancer 103(11):1644-8 (2010).
Neesse A, et al., "Stromal Biology and Therapy in Pancreatic Cancer," Gut. 60(6):861-8 (2011). Epub 2010.
Nelson R, "Lipsomal Irinotecan Boosts Survival in Pancreatic Cancer," Medscape, available at medscape.com/viewarticle/838501, 2015, 2 printed pages.
Nieto J, et. al., "Metastatic Pancreatic Cancer 2008: Is the Glass Less Empty?," Oncologist. 13(5):562-76 (2008) and erratum found at Oncologist 13(6):738 (2008).
Novarino A, et. al., "Oxaliplatin, 5-Fluorouracil, and Leucovorin as Second-Line Treatment for Advanced Pancreatic Cancer," Am J Clin Oncol. 32(1):44-8 (2009).
Oberstein P And Olive K, "Pancreatic Cancer: Why Is It So Hard to Treat?" Ther Adv Gastroenterol. 6(4):321-37 (2013).
Oettle H and Lehmann T, "Gemcitabine-Resistant Pancreatic Cancer: A Second-Line Option," Lancet. 387 (10018):507-8 (2016). Epub 2015.
Olszewski A, et. al., "Phase I Study of Oxaliplatin in Combination with Gemcitabine, Irinotecan, and 5-Fluorouracil/Leucovorin(G-FLIE) in Patients with Metastatic Solid Tumors Including Adenocarcinoma of the Pancreas," J Gastrointest Cancer. 44(2):182-9 (2013).
O'Reilly E, et al., "Impact of Prior Irinotecan Exposure on Outcomes of Metastatic Pancreatic Cancer Patients." Poster presented

(56) References Cited

OTHER PUBLICATIONS at the American Society of Clinical Oncology Gastrointestinal Cancers Symposium (ASCO GI), San Francisco, CA, Jan. 23-25, 2020, 6 pages.

O'Reilly E, et al., "Real-World Patterns of Care Among Patients With Metastatic Pancreatic Cancer." Poster presented at the American Society of Clinical Oncology Gastrointestinal Cancers Symposium (ASCO GI), San Francisco, CA, Jan. 23-25, 2020, 6 pages.

O'Reilly E, et al., Abstract 666. "Real-World Patterns of Care Among Patients With Metastatic Pancreatic Cancer (mPC)," J Clin Oncol. 38(4_Suppl):666 DOI: 10.1200/JC0.2020.38.4_suppl_666 (2020), 2 printed pages.

O'Reilly E, et al., Abstract 667. "Impact of Prior Irinotecan Exposure on Outcomes of Metastatic Pancreatic Cancer (mPC) Patients," J Clin Oncol. 38(4_Suppl):667 DOI: 10.1200/JC0.2020.38.4_suppl. 667 (2020), 2 printed pages.

O'Reilly E, et. al., "A Cancer and Leukemia Group B Phase II Study of Sunitinib Malate in Patients with Previously Treated Metastatic Pancreatic Adenocarcinoma (CALGB 80603)," Oncologist. 15(12):1310-9 (2010).

Pan-Canadian Oncology Drug Review (pCODR) Expert Review Committee (pERC) Final Recommendation for rinotecan Liposome (Onivyde) for Metastaic Pancreatic Cancer, pERC Meeting: Oct. 19, 2017, pERC Reconsideration Meeting: Dec. 17, 2017, pp. 1-14.

Papadatos-Pastos D, et.al., "FOLFIRINOX-A New Paradigm in the Treatment of Pancreatic Cancer," Expert Rev Anticancer Ther. 14(10):1115-25 (2014).

Parekh H, et al., "A Phase II, Open-Label Pilot Study Evaluating the Safety and Activity of Nal-IRI in Combination With 5-FU and Oxaliplatin in Preoperative Treatment of Pancreatic Adenocarcinoma (NEO-Nal-IRI Study)." Poster presented at the American Society of Clinical Oncology Gastrointestinal Cancers Symposium (ASCO GI), San Francisco, CA, Jan. 23-25, 2020, 3 pages.

Parekh H, et al., Abstract TPS790. "A Phase II, Open-Label Pilot Study Evaluating the Safety and Activity of Nal-IRI in Combination With 5 -FU and Oxaliplatin in Preoperative Treatment of Pancreatic Adenocarcinoma (NEO-Nal-IRI Study) (NCT03483038)," J Clin Oncol. 38(4_Suppl):TPS790 (2020), 2 printed pages.

Park J, English abstract and Table 1 and Figure 1 of "Second Line Chemotherapy for Pancreatic Cancer," Korean J Gastroenterol. 57(4):207-12 (2011).

Pellino A, et al., "Observational Retrospective Evaluation of Treatment With Liposomal Irinotecan Plus Fluorouracil/Leucovorin for Metastatic Pancreatic Cancer Patients: An Italian Large Real-World Analysis." Poster presented at the American Society of Clinical Oncology Gastrointestinal Cancers Symposium (ASCO GI), San Francisco, CA, Jan. 23-25, 2020, 5 pages.

Pellino A, et al., Abstract 660. "Observational Retrospective Evaluation of Treatment With Liposomal Irinotecan Plus Fluorouracil/Leucovorin for Metastatic Pancreatic Cancer Patients: An Italian Large Real-World Analysis," J Clin Oncol. 38(4_Suppl):660 DOI: 10.1200/JC0.2020.38.4_suppl.660 (2020), 2 printed pages.

Pelzer U, et al., "A Randomized Trial in Patients With Gemcitabine Refractory Pancreatic Cancer. Final Results of the CONKO-003 Study." Presentation presented at the American Society of Clinical Oncology (ASCO) Annual Meeting, Chicago, Illinois, May 30-Jun. 3, 2008, 18 pages.

Pelzer U, et al., "Best Supportive Care (BSC) Versus Oxaliplatin, Folinic Acid and 5-Fluorouracil (OFF) Plus BSC in Patients for Second-Line Advanced Pancreatic Cancer: A Phase III-Study from the German CONKO-Study Group," Eur J Cancer. 47(11):1676-81 (2011).

Pelzer U, et al., Abstract P865. "Quality-Adjusted Time Without Symptoms or Toxicity (Q-TWiST) of Nanoliposomal Irinotecan (nal-IRI;MM-398) Plus 5-Fluorouracil and Leucovorin (5-FU/LV) vs 5-FU/LV alone in patients (pts) With Metastatic Pancreatic Adenocarcinoma (mPAC) Previously Treated With Gemcitabine-Based Therapy," Oncol Res Treat. 39(Suppl 3):260 (2016).

Petrelli F, et al., "What Else in Gemcitabine-Pretreated Advanced Pancreatic Cancer? An Update of Second Line Therapies," Rev Recent Clin Trials. 5(1):43-56 (2010).

Philip P, et al., "Consensus Report of the National Cancer Institute Clinical Trials Planning Meeting on Pancreas Cancer Treatment," J Clin Oncol. 27(33):5660-9 (2009).

Picozzi V, et al., "An Assessment of the Total Cost of Pancreatic Cancer Using Real-World Evidence." Poster presented at the American Society of Clinical Oncology Gastrointestinal Cancers Symposium (ASCO GI), San Francisco, CA, Jan. 23-25, 2020, 6 pages.

Picozzi V, et al., Abstract 773. "An Assessment of the Total Cost of Pancreatic Cancer Using Real-World Evidence," J Clin Oncol. 38(4_Suppl):773 DOI: 10.1200/JCO.2020.38.4_suppl.773 (2020), 2 printed pages.

Pino M, et. al., "Capecitabine and Celecoxib as Second-Line Treatment of Advanced Pancreatic and Biliary Tract Cancers," Oncology. 76(4):254-61 (2009).

Poplin E, et. al., "Phase III, Randomized Study of Gemcitabine and Oxaliplatin Versus Gemcitabine (Fixed-Dose Rate Infusion) Compared With Gemcitabine (30-Minute Infusion) in Patients With Pancreatic Carcinoma E6201: A Trial of the Eastern Cooperative Oncology Group," J Clin Oncol. 27(23):3778-85 (2009).

Rahib L, et. al., "Evaluation of Pancreatic Cancer Clinical Trials and Benchmarks for Clinically Meaningful Future Trials: A Systematic Review," JAMA Oncol. 2(9):1209-16 (2016).

Ramnani K, et al., Abstract CT13. "Impact of Treatment Sequence on Overall Survival in Metastatic Pancreatic Cancer Patients Treated with Liposomal Irinotecan in the Real-World Selling," Hematology Oncology Pharmacy Association (HOPA) Annual Conference, Mar. 11-14, 2020, available at eventscribe.com/2020/posters/HOPAahead/ SplitViewerasp?Pid=NjgONzMy0DlyNzY, (2020), 2 pages.

Reni M, et. al., "Raltitrexed—Eloxatin Salvage Chemotherapy in Gemcitabine-Resistant Metastatic Pancreatic Cancer," Br J Cancer. 94(6):785-91 (2006).

Renouf D, et. al., "A Phase II Study of Erlotinib in Gemcitabine Refractory Advanced Pancreatic Cancer," Eur J Cancer. 50(11):1909-15 (2014).

Rocha Lima C, et al., "Irinotecan Plus Gemcitabine Results in No Survival Advantage Compared With Gemcitabine Monotherapy in Patients With Locally Advanced or Metastatic Pancreatic Cancer Despite Increased Tumor Response Rate," J Clin Oncol. 22(18):3776-83 (2004).

Sancho A, et. al., Abstract 15625. "Oxaliplatin and Capecitabine After Gemcitabine Failure in Patients With Advanced Pancreatic, Biliary, and Gallbladder Adenocarcinoma (APBC)," J Clin Oncol. 26(15_suppl):15625 (2008), 5 printed pages.

Shi S, et al., "Combinational Therapy: New Hope for Pancreatic Cancer?" Cancer Lett. 317(2):127-35 (2012). Epub 2011.

Siveke J, et al., "Subgroup Analysis by Measurable Metastatic Lesion (ML) Number and Selected Lesion Locations (LL) at Baseline (BL) in NAPOLI-1: A Phase 3 Study of Liposomal Irinotecan (nal-IRI)±5-Fluorouracil/Leuc,ovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 8 pages.

Siveke J, et al., Abstract 460. "Subgroup Analysis by Measurable Metastatic Lesion (ML) Number and Selected Lesion Locations (LL) at Baseline (BL) in NAPOLI-1: A Phase III Study of Liposomal Irinotecan (nal-IRI) 15-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):460 Doi: 10.1200/JCO.2018.36.4_suppl.460 (2018), 2 printed pages.

Siveke J, et al., Abstract ID0596. "Expanded Analyses of Napoli-1: Phase 3 Study of nal-IRI (MM-398), With or Without 5-Fluorouracil (5FU) and Leucovorin (LV), Versus 5-Fluorouracil and Leucovorin (5FU/LV), in Metastatic Pancreatic Cancer (mPAC) Previously Treated With Gemcitabine-Based Therapy," Oncol Res Treat 39(Suppl 1):170 2016).

(56) References Cited

OTHER PUBLICATIONS

Siveke J, et al., Abstract P863. "Effects of Nanoliposomal Irinotecan (nal-IRI;MM-398) ± 5-Fluorouracil and Leucovorin (5-FU/LV) on Quality of Life (QoL) in NAPOLI-1: A Phase 3 Study in Patients (pts) With Metastatic Pancreatic Adenocarcinoma (mPAC) Previously Treated With Gemcitabine-Based Therapy," Oncol Res Threat. 39 (Suppl 3):259 (2016).

Soares H, et. al., "A Phase II Study of Capecitabine Plus Docetaxel in Gemcitabine-Pretreated Metastatic Pancreatic Cancer Patients: CapTere," Cancer Chemother Pharmacol. 73(4):839-45 (2014).

Sohal D et. al., "Metastatic Pancreatic Cancer: ASCO Clinical Practice Guideline Update," J Clin Oncol. 36 (24):2545-2556 and appendix (2018).

Sohal D, et. al., "Metastatic Pancreatic Cancer: American Society of Clinical Oncology Clinical Practice Guideline," J Clin Oncol. 34(23):2784-96 and Appendix (2016).

Abrams T, et al., "Patterns of Chemotherapy Use in a U.S.-Based Cohort of Patients with Metastatic Pancreatic Cancer," Oncologist. 22(8):925-933 (2017).

Abushahin L, et al., "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan." Poster presented at the European Society for Medical Oncology Virtual Congress Sep. 19-21, 2020, 3 pages.

Abushahin L, et al., Abstract 1534P. "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan" Ann Oncol. 31(Suppl_4):S881-S897 10.1016/annondannonc285 (2020), 2 printed pages.

Abushahin L, et al., Abstract e16780. "Real-World Dosing, Management, and Clinical Outcomes of Patients (pts) With Metastatic Pancreatic Adenocarcinoma (mPDAC) Treated With Liposomal Irinotecan," J Clin Oncol. 38 (15_Suppl):e16780 DOI: 10.1200/JCO.2020.38.15_suppLe16780 (2020), 2 printed pages.

Ahn D, et aL, "Real-World Dosing Patterns of Patients With Metastatic Pancreatic Cancer (mPC) Treated With Liposomal Irinotecan (nal-IRI) in US Oncology Clinics." Poster presented at the European Society for Medical oncology (ESMO), Munich, Germany, Oct. 19-23, 2018, 8 pages.

Ahn D, et aL, Abstract 735P. "Real-World Dosing Patterns of Patients (pts) With Metastatic Pancreatic Cancer (mPC) Treated With Liposomal Irinotecan (nal-IRI) in US Oncology Clinics," Ann Oncol. 29(Suppl_8):viii251 doi:10.1093/annonc/mdy282 (2018).

Amzal B, et al., "Imputing Missing Values to Estimate Health-Related Quality of Life (HR-QoL) in Metastatic Pancreatic Cancer Treated With 5-Fluorouracil and Leucovorin, With and Without Liposomal Irinotecan (nal-IRI)." Poster presented at the International Society for Pharmacoeconomics and Outcomes Research (ISPOR) Annual Meeting, Boston, MA, May 20-24, 2017, 6 pages.

Amzal B, et al., Abstract PCN179. "Imputing Missing Values to Estimate Health-Related Quality of Life (HR-QoL) in Metastatic Pancreatic Cancer (mpc) Treated With 5-Fluorouracil and Leucovorin, With and Without Liposomal Irinotecan (nal-IRI)," Value in Health. 20(5):A119 (2017).

Araneo M, et. al., "Biweekly Low-Dose Sequential Gemcitabine, 5-Fluorouracil, Leucovorin, and Cisplatin (GFP): A Highly Active Novel Therapy for Metastatic Adenocarcinoma of the Exocrine Pancreas," Cancer Invest. 21(4):489-96 :2003).

Atkins K, et al., "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)." Poster presented at the American Society of Clinical Oncology Gastrointestinal Cancers Symposium (ASCO GI), San Francisco, CA, Jan. 23-25, 2020, 1 page.

Atkins K, et al., Abstract TPS780. "A Phase I Study of Nanoliposomal Irinotecan and 5-Fluorouracil/Folinic Acid in combination With Interleukin-1-alpha Antagonist for Advanced Pancreatic Cancer Patients With Cachexia (OnFX)," J Clin Oncol. 38(4_Suppl):TPS780 DOI: 10.1200/JC0.2020.38.4_suppl.TPS780 (2020), 2 printed page.

Barbier S, et al., Abstract e16724. "Differentiation of Liposomal Irinotecan From Dose-Dense Non-Liposomal Irinotecan in Patient-Derived Pancreatic Cancer Xenograft Tumor Models," J Clin Oncol. 38(15_Suppl):e16724 DOI: 10.1200/JC0.2020.38.15_suppl.e16724 (2020), 5 printed pages.

Barzi A, et al., Abstract e16229. "Real World Outcomes of Metastatic Pancreatic Cancer (mPC) Patients (pts) Treated With Liposomal Irinotecan (nal-IRI) in the US," J Clin Oncol. 36(15_Suppl):e16229 DOI: 10.1200/JCO.2018.36.15_suppl.e16229 (2018), 2 printed pages.

Becker C, et al., "Multivariate Analysis of Health-Related Quality of Life (HR-QoL) in Metastatic Pancreatic Cancer Treated with 5-Fluorouracil and Leucovorin (5-FU/LV), With and Without Liposomal Irinotecan (nal-IRI)." Poster presented at the International Society for Pharmacoeconomics and Outcomes Research (ISPOR) Annual Meeting, Boston, MA, May 20-24, 2017, 7 pages.

Becker C, et al., Abstract PCN182. "Multivariate Analysis of Health-Related Quality of Life (HR-QoL) in Metastatic Pancreatic Cancer (mPC) Treated with 5-Fluorouracil and Leucovorin, With and Without Liposomal Irinotecan (nal-IRI)," Value in Health. 20(5):A120 (2017).

Becker C, et al., Abstract PCN58. "Budget Impact Analysis of Nanoliposomal Irinotecan for Treatment of Pancreatic Cancer Following Progression on Gemcitabine-A US Payer Perspective," Value in Health. 19(7):A718-A719 (2016).

Blanc J, et al., "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy." Poster presented at the European Society for Medical Oncology Asia 2017 Congress, Singapore, Nov. 17-19, 2017, 8 pages.

Blanc J, et al., Abstract 228P. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy," Ann Oncol. 28(Suppl_10):x67-x68 doi:10.1093/annonc/mdx660 :2017).

Blanc J, et al., Abstract PD-18. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated With Gemcitabine-Based Therapy," Ann Oncol. 28(Suppl_3):7 doi:10.1093/annonc/mdx263 (2017).

BlueCross Blue Shield of North Carolina Corporate Medical Policy, Bevacizumab in Advanced Adenocarcinoma of the Pancreas, File Name: bevacizumab_in_advanced_adenocarcinoma_of the_pancreas, Origination: Mar. 2010, Last review: Feb. 2019, 5 pages.

Boeck S and Heinemann V, "Second-Line Therapy in Gemcitabine-Pretreated Patients With Advanced Pancreatic Cancer," J Clin Oncol. 26(7):1178-9 (2008).

Brus C and Saif M, "Second Line Therapy for Advanced Pancreatic Adenocarcinoma: Where Are We and Where Are We Going?," J Pancreas (Online) 11(4):321-3 (2010).

Burris H and Rocha-Lima C, "New Therapeutic Directions for Advanced Pancreatic Cancer: Targeting the Epidermal Growth Factor and Vascular Endothelial Growth Factor Pathways," Oncologist. 13(3):289-98 (2008).

Casinu S, et al., "Pancreatic Cancer: ESMO Clinical Practice Guidelines for Diagnosis, Treatment and Follow-up," Ann Oncol. 21(Suppl 5):v55—v58 (2010).

Cerenzia W, et al., Abstract e16233. "Identifying Continuing Educational Needs Among Oncologists in Managing Patients With Pancreatic Cancer," J Clin Oncol. 36(15_Suppl):e16233 DOI: 10.1200/JC0.2018.36.15_suppl.e16233 :2018), 2 printed pages.

Chen L-T, et al., "CA19-9 Decrease and Overall Survival (OS) in the NAPOLI-1 Trial of Liposomal Irinotecan (nal-IRI) 5-Fluorouracil and Leucovorin (5-FU/LV) in Metastatic Pancreatic Ductal Adenocarcinoma (mPDAC) Previously Treated With Gemcitabine-Based Therapy." Poster presented at the European Society for Medical Oncology (ESMO) World Congress on Gastrointestinal Cancer, Barcelona, Spain, Jun. 28-Jul. 1, 2017, 5 pages.

(56) References Cited

OTHER PUBLICATIONS

Chen L-T, et al., "CA19-9 Decrease and Overall Survival in the NAPOLI-1 Trial of Liposomal Irinotecan (nal-IRI) ± 5-Fluorouracil and Leucovorin (5-FU/LV) in Metastatic Pancreatic Ductal Adenocarcinoma Previously Treated With Gemcitabine-Based Therapy." Poster presented at the European Society for Medical Oncology Asia 2017 Congress, Singapore, Nov. 17-19, 2017, 8 pages.
Chen L-T, et al., "Early Dose Reduction/Delay and the Efficacy of Liposomal Irinotecan With Fluorouracil and Leucovorin in Metastatic Pancreatic Ductal Adenocarcinoma (mPDAC): A Post Hoc Analysis of NAPOLI-1," Pancreatology. 21(1):192-9 (2021). Epub 2020.
Chen L-T, et al., "Efficacy and Safety of Liposomal Irinotecan (nal-IRI) + 5-Fluorouracil and Leucovorin in Patients With Metastatic Pancreatic Ductal Adenocarcinoma Who Previously Received Gemcitabine-Based Therapy: Post Hoc Analysis of the NAPOLI-1 Trial." Poster presented at the American Society of Clinical Oncology Gastrointestinal Cancers Symposium (ASCO GI), San Francisco, CA, Jan. 19-21, 2017, 9 pages.
Chen L-T, et al., "Final Results of NAPOLI-1: A Phase 3 Study of nal-IRI (MM-398) ± 5-Fluorouracil and Leucovorin (5-FU/LV) vs 5-FU/LV in Metastatic Pancreatic Ductal Adenocarcinoma (mPDAC) Previously Treated With Gemcitabine-Based Therapy." Poster presented at the European Society for Medical Oncology (ESMO) Annual congress, Copenhagen, Denmark, Oct. 7-11, 2016, 8 pages.
Chen L-T, et al., "Impact of Dose Reduction or Dose Delay on the Efficacy of Liposomal Irinotecan (nal-IRI)+5 -Fluorouracil/Leucovorin (5-FU/LV): Survival Analysis From NAPOLI-1." Poster presented at the European Society for Medical Oncology (ESMO) Annual Congress, Munich, Germany, Oct. 19-23, 2018, 9 pages.
Chen L-T, et al., "The Prognostic Value of the Modified Glasgow Prognostic Score (mGPS) in Predicting Overall Survival (OS) in Patients With Metastatic Pancreatic Ductal Adenocarcinoma (mPDAC) Receiving Liposomal rinotecan (nal-IRI)+5-Fluorouracil and Leucovorin (5-FU/LV)." Poster presented at the European Society for Medical Oncology (ESMO) Annual Congress, Munich, Germany, Oct. 19-23, 2018, 9 pages.
Chen L-T, et al., Abstract 221PD. "Efficacy and Safety of Nanoliposomal Irinotecan (nal-IRI, MM-398, PEP02, BAX-2398) in Patients With Metastatic Pancreatic Cancer in Asia: A Subgroup Analysis of the Phase 3 NAPOLI-1 Study," Ann Oncol. 27(Supp_9):ix69-ix70 doi:10.1093/annonc/mdw582 (2016).
Chen L-T, et al., Abstract 227P. "CA19-9 Decrease and Overall Survival (OS) in the NAPOLI-1 Trial of Liposomal Irinotecan (nal-IRI)± 5-Fluorouracil and Leucovorin (5-FU/LV) in Metastatic Pancreatic Ductal Adenocarcinoma (mPDAC) Previously Treated With Gemcitabine-Based Therapy," Ann Oncol. 28(Suppl_10):x66-x67 doi: 10.1093/ annondmdx660 (2017).
Chen L-T, et al., Abstract 303. "Efficacy and Safety of Liposomal Irinotecan (nal-IRI) + 5-Fluorouracil and Leucovorin (5-FU/LV) in Patients (pts) With Metastatic Pancreatic Ductal Adenocarcinoma (mPDAC) Who Previously Received Gemcitabine (Gem)-Based Therapy: Post Hoc Analysis of the NAPOLI-1 Trial," J Clin Oncol. 35(4_Suppl):303 DOI: 10.1200/JC0.2017.35.4_suppl.303 (2017), 2 printed pages.
Chen L-T, et al., Abstract 3707. "Final Results of NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6)207-242 10.1093/annondmdw371 (2016), 4 printed pages.
Chen L-T, et al., Abstract 734P. "Impact of Dose Reduction or Dose Delay on the Efficacy of Liposomal Irinotecan (nal-IRI)+5-Fluorouracil/Leucovorin (5-FU/LV): Survival Analysis From NAPOLI-1," Ann Oncol. 29(Suppl_8):viii250-viii251 doi:10.1093/annondmdy282 (2018).
Chen L-T, et al., Abstract 749P. "The Prognostic Value of the Modified Glasgow Prognostic Score (mGPS) in ?Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)," Ann Oncol. 29(Suppl_8):viii255-viii256 doi:10.1093/annondmdy282 (2018).

Chen L-T, et al., Abstract PD-017. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy," Ann Oncol. 28(Supp_3):6-7 doi:10.1093/annonc/mdx263 (2017).
Chen V, eL al., "Chemotherapy and Radiotherapy for Advanced Pancreatic Cancer (Review)," Cochrane Database Syst Rev. 3(3):CD011044 doi: 10.1002/14651858.CD011044.pub2 (2018), 143 pages.
Choi C, et al., "Effects of 5-Fluorouracil and Leucovorin in the Treatment of Pancreatic-Biliary Tract Adenocarcinomas," Am J Clin Oncol. CCT 23(4): 425-8 (2000), 7 printed pages.
Clinical Trials Identifier NCT00426127: Dec. 29, 2017 update, first posted Jan. 24, 2007, "Docetaxel and Liposomal Doxorubicin Chemotherapy With Enoxaparin in Patients With Advanced Pancreatic Cancer," Retrieved from ClinicalTrials.gov archive, 8 printed pages.
Cockrum P, et al., "Impact of Dose Reductions on Clinical Outcomes Among Patients With Metastatic Pancreatic cancer Treated With Liposomal Irinotecan in Oncology Clinics in the US." Poster presented at the American Society of Clinical Oncology Gastrointestinal Cancers Symposium (ASCO GI), San Francisco, CA, Jan. 23-25, 2020, 8 pages.
Cockrum P, et al., Abstract 665. "Impact of Dose Reductions on Clinical Outcomes Among Patients (pts) With Metastatic Pancreatic Cancer (mPC) Treated With Liposomal Irinotecan (nal-IRI) in Oncology Clinics in the United States," J Clin Oncol. 38(4_Suppl):665 DOI: 10.1200/JC0.2020.38.4_suppl.665 (2020), 2 printed pages.
Cockrum P, et al., Abstract e16739. "National Comprehensive Cancer Network (NCCN) Category I/FDA-Approved Metastatic Pancreatic Adenocarcinoma (mPDAC) Treatments in Commercially Insured Patients: An Analysis of Inpatient (IP) and Emergency Room (ER) Admissions," J Clin Oncol. 38(15_Suppl):e16739 DOI: 10.1200/JCO.2020.38.15_suppl.e16739 (2020), 2 printed pages.
Cockrum P, et al., Abstract PCN134. "An Examination of Quality Metrics: Inpatient and Emergency Department Burden of Commercially Insured Treated Metastatic Pancreatic Cancer (mPC) Patients in the United States (US)," Value in Health. 23(Suppl 1):S46 (2020).
Cockrum P, et al., Abstract PCN167. "An Integrated Delivery Network Focus on Cost Drivers in Chemotherapy: The Economic Burden of Neutropenia and Inpatient Admissions Among Commercially Insured Metastatic Pancreatic Cancer Patients (mPC)," Value in Health. 23(Suppl 1):S52 (2020).
Colucci G, et. aL, "Randomized Phase III Trial of Gemcitabine Plus Cisplatin Compared With Single-Agent Gemcitabine as First-Line Treatment of Patients With Advanced Pancreatic Cancer: The GIP-1 Study," J Clin Oncol. 28(10)1645-51 (2010).
Conroy T et al., Abstract 4010. "Randomized Phase III Trial Comparing FOLFIRINOX (F: 5FU/Leucovorin [LV], Irinotecan [I}, and Oxaliplatin [O]) Versus Gemcitibine (G) as First-Line Treatment for Metastatic Pancreatic Adenocarcinoma (MPA): Preplanned Interim Analysis Results of the Prodige 4/Accord 11 Trial" J Clin Oncol. 28 '15_Suppl):4010 (2010), 3 printed pages.
Custodio A, et. al., "Second-Line Therapy for Advanced Pancreatic Cancer: A Review of the Literature and Future Directions," Cancer Treat Rev. 35(8):676-84 (2009).
Pavai S and Yap S, "The Clinical Significance of Elevated Levels of Serum CA19-9," Med J Malaysia. 58(5):667-72 ;2003).
Paz-Ares L, et aL, "Resilient part 2: An Open-Label, Randomized, Phase 3 Study of Liposomal Irinotecan Injection in Patients With Small-Cell Lung Cancer Who Have Progressed With Platinum-Based First-Line Therapy." Poster presented at the American Society of Clinical Oncology (ASCO) Annual Conference, virtual format, May 29-Jun. 2, 2020, 7 pages.
Paz-Ares L, et al., Abstract TPS9081. "Resilient part II: An Open-Label, Randomized, Phase III Study of Liposomal Irinotecan Injection in Patients With Small-Cell Lung Cancer Who Have Progressed With Platinum-Based First-Line Therapy," J Clin Oncol. 38(15_Suppl):TPS9081 DOI: 10.1200/JCO.2020.38.15_suppl.TPS9081 (2020), 2 printed pages.

(56) References Cited

OTHER PUBLICATIONS

Pillai G, "Nanomedicines for Cancer Therapy: An Update of FDA Approved and Those under Various Stages of Development," SOJ Pharm Pharm Sci. 1(2):13 (2014), 13 pages.
Pounce S, et al., "Resilient Part 1: Pharmacokinetics of Second-Line (2L) Liposomal Irinotecan in Patients with Small Cell Lung Cancer (SCLC)," Poster presented at the European Society for Medical Oncology (ESMO) Virtual Congress 2020, virtual format, Sep. 19-21, 2020, 8 pages.
Pounce S, et al., Abstract 1793P. "Resilient Part 1: Pharmacokinetics of Second-Line (2L) Liposomal Irinotecan in Patients with Small Cell Lung Cancer (SCLC)," Ann Oncol. 31(S4):S1038-S1039 (2020).
Poplin E, et. al.,"Phase III Southwest Oncology Group 9415/Intergroup 0153 Randomized Trial of Fluorouracil, Leucovorin, and Levamisole Versus Fluorouracil Continuous Infusion and Levamisole for Adjuvant Treatment of Stage III and High-Risk Stage II Colon Cancer," J Clin Oncol. 23(9):1819-25 (2005).
Ramsay E, et. al., "Irinophore C: A Liposome Formulation of Irinotecan With Substantially Improved Therapeutic Efficacy Against a Panel of Human Xenograft Tumors," Clin Cancer Res. 14(4):1208-17 (2008).
Rea D, et al., "A Phase I/II and Pharmacokinetic Study of Irinotecan in Combination with Capecitabine as First-Line Therapy for Advanced Colorectal Cancer," Ann Oncol. 16(7):1123-32 (2005).
Reynolds J, et al., "HER2-Targeted Liposomal Doxorubicin Displays Enhanced Anti-Tumorigenic Effects Without Associated Cardiotoxicity," Toxicol Appl Pharmacol. 262(1):1-10 (2012).
Rosenecker J, et al., "Increased Liposome Extravasation in Selected Tissues: Effect of Substance P," Proc Natl Acad Sci U S A. 93(14):7236-41 (1996).
Roth A, et al., "Anti-CD166 Single Chain Antibody-Mediated Intracellular Delivery of Liposomal Drugs to Prostate Cancer Cells," Mol Cancer Ther. 6(10):2737-46 (2007).
Rothenberg M, et_al., "Alternative Dosing Schedules for Irinotecan," Oncology. 12(8 Suppl 6):68-71 (1998). Available at cancernetwork.com/view/alternative-dosing-schedules-irinotecan, 16 printed pages.
Rubesova E, et al., "Gd-Labeled Liposomes for Monitoring Liposome-Encapsulated Chemotherapy: Quantification of Regional Uptake in Tumor and Effect on Drug Delivery," Acad Radio!. 9(Suppl 2):S525-7 (2002).
Saif M, et. al., "Pharmacokinetically Guided Dose Adjustment of 5-Fluorouracil: A Rational Approach to Improving Therapeutic Outcomes," J Natl Cancer Inst. 101(22):1543-52 (2009).
Saltz L, "Clincial Use of Irinotecan: Current Status and Future Considerations," Oncologist. 2(6):402-9 (1997).
Saltz LB, et. al., "Phase I Clinical and Pharmacokinetic Study of Irinotecan, Fluorouracil, and Leucovorin in Patients With Advanced Solid Tumors," J Clin Oncol. 14(11):2959-67 (1996).
Satoh T, et. al., "Pharmacokinetic Assessment of Irinotecan, SN-38, and SN-38-Glucuronide: A Substudy of the FIRIS Study," Anticancer Res. 33(9):3845-53 (2013).
Scheithauer W, et. al., "Fluorouracil Plus Racemic Leucovorin Versus Fluorouracil Combined With the Pure I-Isomer of Leucovorin for the Treatment of Advanced Colorectal Cancer: A Randomized Phase III Study," J Clin Oncol. 15(3):908-14 (1997).
Schroen A, et. al., "Challenges to Accrual Predictions to Phase III Cancer Clinical Trials: A Survey of Study Chairs and Lead Statisticians of 248 NCI Sponsored Trials," Clin Trials. 8(5):591-600 (2011), author manuscript version, 14 pages.
Serwer L, et al., "Investigation of Intravenous Delivery of Nanoliposomal Topotecan for Activity Against Orthotopic Glioblastoma Xenografts," Neuro Oncol. 13(12):1288-95 (2011).
Skof E, et. al., "Capecitabine Plus Irinotecan (XELIRI Regimen) Compared to 5-F/LV Plus Irinotecan (FOLFIRI Regimen) As Neoadjuvant Treatment for Patients With Unresectable Liver-Only Metastases of Metastatic Colorectal Cancer: A Randomised Prospective Phase II Trial," BMC Cancer. 9:120 doi: 10.1186/1471-2407-9-120 (2009), 9 pages.
Spigel D, et al., "Liposomal Irinotecan in Adults with Small Cell Lung Cancer Who Progressed on Platinum-Based Therapy: Subgroup Analyses by Platinum Sensitivity." Poster presented at the International Association for the Study of Lung Cancer (IASLC) 2020 North America Conference on Lung Cancer (NACLC): virtual meeting, Oct. 16-17, 2020, 9 pages.
Spigel D, et al., "Resilient Part 1, An Open-Label, Safety Run-In of Liposomal Irinotecan in Adults With Small Cell Lung Cancer (SCLC) Who Have Progressed With Platinum-Based First-Line Therapy: Subgroup Analyses by Platinum Sensitivity." Poster presented at the American Society of Clinical Oncology (ASCO) Annual Conference, virtual format, May 29-Jun. 2, 2020, 6 pages.
Spigel D, et al., Abstract 9069. "Resilient Part I, An Open-Label, Safety Run-In of Liposomal Irinotecan in Adults With Small Cell Lung Cancer (SCLC) Who Have Progressed With Platinum-Based First-Line (10 Therapy: Subgroup Analyses by Platinum Sensitivity," J Clin Oncol. 38(15_Suppl):9069 Doi: 10.1200/JCO.2020.38_15_suppl.9069 (2020), 2 printed pages.
Spigel D, et al., Abstract M001.39. "Liposomal Irinotecan in Adults with Small Cell Lung Cancer Who Progressed on Platinum-Based Therapy: Subgroup Analyses by Platinum Sensitivity," IASLC 2020 North America Conference on Lung Cancer Abstracts, p. 80 (2020).
Stathopoulos G and Boulikas T, "Lipoplatin Formulation Review Article," J Drug Deliv. 2012:581363, Article ID 581363, doi:10.1155/20121581363, Epub 2011, 10 pages.
Stathopoulos G, et. al., "Liposomal Oxaliplatin in the Treatment of Advanced Cancer: A Phase I Study," Anticancer Res. 26(2B):1489-93 (2006).
Stylianopoulos T and Jain R, "Combining Two Strategies to Improve Perfusion and Drug Delivery in Solid Tumors," Proc Natl Acad Sci USA. 110(46):18632-7 (2013).
Takano S, et. al., "Metronomic Treatment of Malignant Glioma Xenografts with Irinotecan (CPT-11) Inhibits Angiogenesis and Tumor Growth," J Neurooncol. 99(2):177-85 (2010).
Tardi P, et. al., "Coencapsulation of Irinotecan and Floxuridine Into Low Cholesterol-Containing Liposomes That Coordinate Drug Release in Vivo," Biochim Biophys Acta. 1768(3):678-87 (2007). Epub 2006.
Toutain P And Bousquet-Melou A, "Plasma terminal half-life," J Vet Pharmacol Ther. 27(6):427-39 (2004).
Tsavaris N, et. al., "Second-Line Treatment With Oxaliplatin, Leucovorin and 5-Fluorouracil in Gemcitabine-Pretreated Advanced Pancreatic Cancer: A Phase II Study," Invest New Drugs. 23(4):369-75 (2005).
U.S. Appl. No. 15/664,976: dated Oct. 13, 2020 Notice of Allowance including Examiner's Reasons for Allowance, 13 pages.
U.S. Appl. No. 16/586,609: dated Oct. 5, 2020 Non-Final Office Action, 5 pages.
Vaage J, eL al., "Therapy of a Xenografted Human Colonic Carcinoma Using Cisplatin or Doxorubicin Encapsulated in Long-Circulating Pegylated Stealth Liposomes," Int J Cancer. 80(1):134-7 (1999).
Veal G, et. al., "A Phase I Study in Paediatric Patients to Evaluate the Safety and Pharmacokinetics of SPI-77, A Liposome Encapsulated Formulation of Cisplatin," Br J Cancer. 84(8):1029-35 (2001).
Venook A, "Critical Evaluation of Current Treatments in Metastatic Colorectal Cancer," Oncologist. 10(4):250-61 (2005).
Villalona-Calero M, et. al., "Phase I Study of Low-Dose Suramin as a Chemosensitizer in Patients With Advanced Non-Small Cell Lung Cancer," Clin Cancer Res. 9(9):3303-11 (2003).
Walker S, et. al., "Simulation of Y-Site Compatibility of Irinotecan and Leucovorin at Room Temperature in 5% Dextrose in Water in 3 Different Containers," Can J Hosp Pharm. 58(4):212-22 (2005).
Wang W, et. al., "Weekly 24-Hour Infusion of High-dose 5-Fluorouracil and Leucovorin in Patients with Advanced Colorectal Cancer: Taiwan Experience," Jpn J Clin Oncol. 28(1):16-19 (1998).
Weng K, et al., "Convection-Enhanced Delivery of Targeted Quantum Dot-Immunoliposome Hybrid Nanoparticles to Intracranial Brain Tumor Models," Nanomedicine (Lond). 8(12):1913-25. 2013.
Weng K, et al., "Targeted Tumor Cell Internalization and Imaging of Multifunctional Quantum Dot-Conjugated Immunoliposomes in Vitro and in Vivo," Nano Lett. 8(9):2851-7 (2008).

(56) References Cited

OTHER PUBLICATIONS

Willett C, et. al., "Direct Evidence That the VEGF-Specific Antibody Bevacizumab Has Antivascular Effects in Human Rectal Cancer," Nat Med. 10(2):145-7 (2004), author manuscript version, 7 pages.

Wulaningsih W, et. al., "Irinotecan Chemotherapy Combined With Fluoropyrimidines Versus Irinotecan Alone for Overall Survival and Progression-Free Survival in Patients With Advanced and/or Metastatic Colorectal Cancer," Cochrane Database Syst Rev. 2:CD008593 doi: 10.1002/14651858.CD008593.pub3. (2016), 36 pages.

Xeloda (capecitabine) package insert, Roche, revised Nov. 2000, 19 pages.

Yamashita Y, et al., "Convection-Enhanced Delivery of a Topoisomerase I Inhibitor (Nanoliposomal Topotecan) and a Topoisomerase II Inhibitor (Pegylated Liposomal Doxorubicin) in Intracranial Brain Tumor Xenografts," Neuro Oncol. 3(1):20-8 (2007). Epub 2006.

Yamashita Y, et. al., "Convection-Enhanced Delivery of Liposomal Doxorubicin in Intracranial Brain Tumor Xenografts," Targ Oncol. 1:79-85 (2006).

Yang W, et. al. "Development of a Method to Quantify Total and Free Irinotecan and 7-ethyl-10-hydroxycamptothecin (SN-38) for Pharmacokinetic and Bio-Distribution Studies After Administration of Irinotecan Liposomal Formulation," Asian J Pharm Sci. 14(6):687-97 (2019). Epub 2018.

Yang W, et. al., "The Influence of Trapping Agents on the Antitumor Efficacy of Irinotecan Liposomes: Head-to-Head Comparison of Ammonium Sulfate, Sulfobutylether-β-Cyclodextrin and Sucrose Octasulfate," Biomater Sci., 7 (1):419-28 (2019).

ClinicalTrials.gov search results for ONIVYDE, retrieved from clinicaltrials.gov website on Jan. 27, 2021, 27 pages.

Abra R, et. al. "The Next Generation of Liposome Delivery Systems: Recent Experience With Tumor-Targeted, Sterically-Stabilized Immunoliposomes and Active-Loading Gradients," J Liposome Res. 12(1-2):1-3 (2002).

Alese O, et al., "A Phase I/II Study of Trifluridine/Tipiracil (TAS-102) in Combination With Nanoliposomal Irinotecan (Nal-IRI) in Advanced GI Cancers." Poster presented at Chan E, et al., "A Phase 1/2 Study Combining MM-151 +nal-IRI + Leucovorin in RAS/RAF Wild-Type Metastatic Colorectal Cancer." Poster presented at the American Society of Clinical Oncology (ASCO) Annual Meeting, Chicago, Illinois, Jun. 1-5, 2018, 1 page.

Alese O, et al., Abstract TPS4155. "A Phase I/II Study of Trifluridine/Tipiracil (TAS-102) in Combination With Nanoliposomal Irinotecan (Nal-IRI) in Advanced GI Cancers," J Clin Oncol. 36(15_Suppl):TPS4155 DOI: 10.1200/JCO.2018.36.15_suppl.TPS4155 (2018), 5 printed pages.

Allegrini G, et. al., "A Pharmacokinetic and Pharmacodynamic Study on Metronomic Irinotecan in Metastatic Colorectal Cancer Patients," Br J Cancer. 98(8):1312-19 (2008).

Alves Da Silva A, et. al., "Standardization of the Infusion Sequence of Antineoplastic Drugs Used in the Treatment of Breast and Colorectal Cancers," Einstein (São Paulo). 16(2):eRW4074 doi: 10.1590/S1679-45082018RW4074 ;2018), 9 pages.

Anders C, et al., Abstract e12003. "Pharmacokinetic (PK) Characterization of Irinotecan Liposome Injection in Patients (pts) With Metastatic Breast Cancer (mBC)," J Clin Oncol. 37(15_Suppl):e12003 DOI: 10.1200/JCO.2019.37.15_suppl.e12003 (2019), 2 printed pages.

Andre T, et. al., "Phase III Study Comparing a Semimonthly With a Monthly Regimen of Fluorouracil and Leucovorin As Adjuvant Treatment for Stage Ii and Iii Colon Cancer Patients: Final Results of Gercor C96.1," Clin Oncol. 25 (24):3732-8 (2007).

Aranda E, et. aL, "Randomized Study of Weekly Irinotecan Plus High-Dose 5-Fluorouracil (FUIRI) Versus Biweekly rinotecan Plus 5-Fluorouracil/Leucovorin (FOLFIRI) As First-Line Chemotherapy for Patients With Metastatic Colorectal Cancer: A Spanish Cooperative Group for the Treatmentof Digestive Tumors Study," Ann Oncol. 20 (2):251-7 (2009).

Awasthi N, et al., "Antitumor Efficacy of a Liposomal Formulation of Irinotecan in Preclinical Gastric Cancer Models: Augmenting Its Response by Antiangiogenic Agents." Poster presented at the Annual Meeting of the American Association for Cancer Research 2020, Philadelphia, PA, Apr. 27-28, 2020 and Jun. 22-24, 2020, 6 pages.

Awasthi N, et al., Abstract 553. "Antitumor Efficacy of a Liposomal Formulation of Irinotecan in Preclinical Gastric Cancer Models: Augmenting Its Response by Antiangiogenic Agents," In Proceedings of the Annual Meeting of the American Association for Cancer Research 2020; Apr. 27-28, 2020 and Jun. 22-24, 2020. Cancer Res. 2020;80(16 Suppl):Abstract nr 553, DOI: 10.1158/1538-7445. AM2020-553, 2 printed pages.

Barenholz Y, "Development of Liposomal Drugs and Nano-Drugs: From Academic Research Via Incubators and Startups to FDA and EMA Approved Products. Part I: Science and Technology," Presentation presented at Barcelona NanoMed, Mar. 4-5, 2014, 89 pages.

Barenholz Y, "Doxil®—The First FDA-Approved Nano-Drug: Lessons Learned," J Control Release. 160(2):117-34 :2012).

Barone C, et. al., "Schedule-Dependent Activity of 5-Fluorouracil and Irinotecan Combination in the Treatment of Human Colorectal Cancer: In Vitro Evidence and a Phase I Dose-Escalating Clinical Trial," Br J Cancer. 96(1):21-8 (2007). Epub 2006.

Basu S, et. al., "Development and Validation of an UPLC-MS/MS Method for the Quantification of Irinotecan, SN 38 and SN-38 Glucuronide in Plasma, Urine, Feces, Liver and Kidney: Application to a Pharmacokinetic Study of Irinotecan in Rats," J Chromatogr B Analyt Technol Biomed Life Sci. 1015-1016: 34-41 (2016).

Batist G, et al., Abstract 2014. "Phase 1 Study of CPX-1, A Fixed Ratio Formulation of Irinotecan (IRI) and Floxuridine (FLOX), in Patients With Advanced Solid Tumors," J Clin Oncol. 24(18_suppl):2014 (2006), 2 printed pages.

Batist G, et al., Abstract 2549. "Ratiometric Dosing of Irinotecan (IRI) and Floxuridine (FLOX) in a Phase I Trial: A New Approach for Enhancing the Activity of Combination Chemotherapy," J Clin Oncol. 25(18_suppl):2549 (2007), 5 printed pages.

Borner M, et. al., "A Randomized Phase II Trial of Capecitabine and Two Different Schedules of Irinotecan in First-Line Treatment of Metastatic Colorectal Cancer: Efficacy, Quality-of-Life and Toxicity," Ann Oncol. 16(2): 282-8 (2005).

Boulikas T, "Clinical Overview on Lipoplatin: A Successful Liposomal Formulation of Cisplatin," Expert Opin Investig Drugs. 18(8):1197-218 (2009), author manuscript version, 22 pages.

Bozzuto G and Molinari A, "Liposomes as Nanomedical Devices," Int J Nanomedicine. 10:975-99 (2015).

Bulbake U, et al., "Liposomal Formulations in Clinical Use: An Updated Review," Pharmaceutics. 9(2):12 doi: 10.3390/pharmaceutics9020012 (2017), 33 pages.

Butowski N, et aL, "A Phase I Study of CED of Nanoliposomal-Irinotecan Using Real-Time Imaging With Gadolinium in Patients With Recurrent High Grade Glioma." Poster presented at the American Society of Clinical Oncology (ASCO) Annual Conference, Chicago, IL, May 29-Jun. 2, 2015, 4 pages.

Butowski N, et al., Abstract TPS2081. "A Phase I Study of Convection-Enhanced Delivery of Nanoliposomal Irinotecan Using Real-Time Imaging in Patients With Recurrent High Grade Glioma," J Clin Oncol. 33(15_Suppl):2081 DOI: 10.1200/jco.2015.33.15_supplips2081 (2015), 2 printed pages.

Caelyx (doxorubicin), MedBroadcast, accessed Jan. 26, 2021 from medbroadcast.com/drug/getdrug/caelyx, 11 printed pages.

Cao S, et. al., "Synergistic Antitumor Activity of Capecitabine in Combination with Irinotecan," Clin Colorectal Cancer. 1(5)336-43 (2005).

Cao Y, et al., "A Gold Nanoparticle Bouquet Held on Plasma Membrane: An Ultrasensitive Dark-Field Imaging Approach for Cancer Cell Analysis," Nanotheranostics. 4(4):201-209 (2020).

Carter K, et. al., "Sphingomyelin Liposomes Containing Porphyrin—Phospholipid for Irinotecan Chemophototherapy," Theranostic.s. 6(13):2329-36 (2016).

Chatbot G, "Clinical Pharmacokinetics of Irinotecan," Clin. Pharmacokinet. 33(4):245-59 (1997).

Chan E, et al., "A Phase 1/2 Study Combining MM-151 + nal-IRI + 5-FU + Leucovorin in RAS/RAF Wild-Type Metastatic Colorectal Cancer." Poster presented at the American Society of Clinical Oncology (ASCO) Annual Meeting, Chicago, Illinois, Jun. 3-7, 2016, 7 pages.

(56) References Cited

OTHER PUBLICATIONS

Chan E, et al., Abstract TPS3633. "A Phase 1b/2 Study Combining MM-151 + nal-IRI + 5-Fu + Leucovorin in RAS-Wildtype Metastatic Colorectal Cancer (mCRC)," J Clin Oncol. 34(15_Suppl):TPS3633 10.1200/JCO.2016.34.15_suppl.TPS3633 (2016), 4 printed pp.
Chauhan V, et. al., "Normalization of Tumour Blood Vessels Improves the Delivery of Nanomedicines in a Size-Dependent Manner," Nat Nanotechnol. 7(6):383-8 (2012), author manuscript version, 15 pages.
Chen J, et al., "Improved Pharmacokinetics and Reduced Toxicity of Brucine After Encapsulation into Stealth Aposomes: Role of Phosphatidylcholine," Int J Nanomedicine. 7:3567-77 (2012).
Chu C-J, et al., "Efficiency of Cytoplasmic Delivery by pH-Sensitive Liposomes to Cells in Culture," Pharm Res. 7 (8):824-34 (1990).
Clarke J, et al., "A Phase I Trial of Intravenous Liposomal Irinotecan in Patients With Recurrent High-Grade Gliomas." Poster presented at the American Society of Clinical Oncology (ASCO) Annual Conference, Chicago, IL, May 29-Jun. 2, 2015, 7 pages.
Clarke J, et al., Abstract 2029. "A Phase I Trial of Intravenous Liposomal Irinotecan in Patients With Recurrent High-Grade Gliomas," J Clin Oncol. 33(15_Suppl):2029 DOI: 10.1200/jco.2015.33.15_suppl.2029 (2015), 2 printed pages.
Comella P, et. al., "Irinotecan Plus Leucovorin-Modulated 5-Fluorouracil I.V. Bolus Every Other Week May Be a Suitable Therapeutic Option Also for Elderly Patients With Metastatic Colorectal Carcinoma," Br J Cancer. 89(6):992-6 (2003).
Daleke D, et al., "Endocytosis of Liposomes by Macrophages: Binding, Acidification and Leakage of Liposomes Monitored by a New Fluorescence Assay," Biochim Biophys Acta. 1024(2):352-66 (1990).
DaunoXome (daunorubicin citrate liposome injection) package insert, rev. Dec. 2011, 11 pages.
Delord J, et. al., "A Phase I Clinical and Pharmacokinetic Study of Capecitabine (Xeloda®) and Irinotecan Combination Therapy (XELIRI) in Patients With Metastatic Gastrointestinal Tumours," Br J Cancer. 92(5):820-6 (2005).
Derksen J, et. al., "Interaction of Immunoglobulin-Coupled Liposomes with Rat Liver Macrophages in Vitro," Exp Cell Res. 168(1):105-15 (1987).
Dewhirst M, et al., "Microvascular Studies on the Origins of Perfusion-Limited Hypoxia," Br J Cancer Suppl. 27: 3247-51 (1996).
Dos Santos N, et al., "Improved Retention of Idarubicin After Intravenous Injection Obtained for Cholesterol-Free Liposomes," Biochim Biophys Acta. 1561(2):188-201 (2002).
Drummond D, et al., "Clinical Development of Histone Deacetylase Inhibitors as Anticancer Agents," Annu Rev Pharmacol Toxicol. 45:495-528 and C1-C2 (2005).
Drummond D, et al., "Development of a Highly Stable and Targetable Nanoliposomal Formulation of Topotecan," J Control Release. 141(1):13-21 (2010). Epub 2009.
Drummond D, et al., "Improved Pharmacokinetics and Efficacy of a Highly Stable Nanoliposomal Vinorelbine," J Pharmacol Exp Ther. 328(1):321-30 (2009). Epub 2008.
Drummond D, et al., "Liposome Targeting to Tumors using Vitamin and Growth Factor Receptors," Vitam Horm. 60:285-332 (2000).
Drummond D, et al., Chapter 8, "Intraliposomal Trapping Agents for Improving in Vivo Liposomal Drug Formulation Stability," in Liposome Technology, Third Edition, vol. 2, Ed. G. Gregoriadis, pp. 149-168 (2006).
Drummond D, et al., Chapter 9, "Liposomal Drug Delivery Systems for Cancer Therapy," in Drug Discovery Systems in Cancer Therapy, Ed. D Brown, Humana Press, Totowa, NJ, pp. 191-213 (2004).
Duffour J, et al., "Efficacy of Prophylactic Anti-Diarrhoeal Treatment in Patients Receiving Campto for Advanced Colorectal Cancer," Anticancer Res. 22(6B): 3727-31 (2002).
Elinzano H, et al., "Nanoliposomal Irinotecan and Metronomic Temozolomide for Patients With Recurrent Glioblastoma BrUOG329, A Phase I Brown University Oncology Research Group Trial," Am J Clin Oncol. 44(2):49-52 :2021). Epub 2020 version, pp. 1-4.
Elinzano H, et al., Abstract e14548. "Nanoliposomal Irinotecan and Metronomic Temozolomide for Patients With Recurrent Glioblastoma: BrUOG329, A Phase IB/IIA Brown University Oncology Research Group (BrUOG) Trial," J :Ain Oncol. 38(15_Suppl):e14548 DOI: 10.1200/JC0.2020.38.15_suppl.e14548 (2020), 2 printed pages.
PCT/US2005/015349: PCT International Search Report and Written Opinion dated Aug. 18, 2005, 14 pages.
PCT/US2016/057247: PCT International Preliminary Report on Patentability dated Apr. 17, 2018, 8 pages.
PCT/US2016/057247: PCT International Search Report dated Dec. 23, 2016, 4 pp.
Sachdev J, et al., Abstract C1048. "Phase I Expansion Study of Irinotecan Liposome Injection (nal-IRI) in Patients with Metastatic Breast Cancer (mBC)," Cancer Res. In Proceedings of the American Association for Cancer Research Annual Meeting 2019; Mar. 29-Apr. 3, 2019; Atlanta, GA. Cancer Res. 2019; 79(13 Suppl):Abstract nr CT048, 4 printed pages.
Saito R, et al., "Distribution of Liposomes into Brain and Rat Brain Tumor Models by Convection-Enhanced Delivery Monitored with Magnetic Resonance Imaging," Cancer Res. 64(7):2572-9 (2004).
Saito R, et al., "Gadolinium-loaded Liposomes Allow for Real-Time Magnetic Resonance Imaging of Convection-Enhanced Delivery in the Primate Brain," Exp Neurol. 196(2):381-9 (2005).
Saito R, et al., "Tissue Affinity of the Infusate Affects the Distribution volume During Convection-Enhanced Delivery Into Rodent Brains: Implications for Local Drug Delivery," J Neurosci Methods. 154(1-2):225-32 (2006).
Tahara M, et al., "The Use of Olaparib (AZD2281) Potentiates SN-38 Cytotoxicity in Colon Cancer Cells by Indirect Inhibition of Rad51-Mediated Repair of DNA Double-Strand Breaks," Mol Cancer Ther. 13(5):1170-80 (2014).
Tardi P, et al., "Drug Ratio-Dependent Antitumor Activity of Irinotecan and Cisplatin Combinations in Vitro and in Vivo," Mol Cancer Ther. 8(8):2266-75 (2009).
Tentori L, et al., "Influence of MLH1 on Colon Cancer Sensitivity to Poly(ADP-ribose) Polymerase Inhibitor Combined with Irinotecan," Int J Oncol. 43(1):210-8 (2013).
U.S. Appl. No. 15/664,976: Nov. 4, 2019 Nonfinal Office Action, 9 pages.
U.S. Appl. No. 15/664,976: dated May 18, 2020 Final Office Action, 11 pages.
U.S. Appl. No. 15/809,815: dated Feb. 27, 2020 Final Office Action, 16 pages.
U.S. Appl. No. 15/896,389: dated Jan. 31, 2020 Final Office Action, 28 pages.
U.S. Appl. No. 15/896,389: dated Mar. 26, 2020 Examiner Interview Summary and Applicant slides, 22 pages.
U.S. Appl. No. 15/896,389: dated Apr. 9, 2020 Advisory Action, 3 pages.
U.S. Appl. No. 15/896,389: Jun. 5, 2020 Notice of Allowance including Examiner's Reasons for Allowance and Examiner Interview Summary, 13 pages.
U.S. Appl. No. 16/012,351: dated Jan. 7, 2020 Final Office Action, 9 pages.
U.S. Appl. No. 16/012,372: dated Jan. 7, 2020 Final Office Action, 9 pages.
U.S. Appl. No. 16/012,372: dated Jul. 27, 2020 Non-Final Office Action, 8 pages.
U.S. Appl. No. 16/302,050: dated Jan. 17, 2020 Non-Final Office Action, 17 pages.
U.S. Appl. No. 16/510,394: dated Mar. 6, 2020 Non-Final Office Action, 15 pages.
U.S. Appl. No. 16/567,902: dated Apr. 27, 2020 Non-Final Office Action, 20 pages.
U.S. Appl. No. 16/567,902: dated Aug. 10, 2020 Final Office Action, 21 pages.
Ventura M, et aL, "Ferumoxytol as an MR Imaging Surrogate Marker of Liposomal Drug Deposition and Longitudinal Efficacy in a Preclinical Model of Breast Cancer." Poster presented at World Molecular Imaging Congress, Sep. 13-16, 2017, Philadelphia, Pennsylvania, 6 pages.

(56) References Cited

OTHER PUBLICATIONS

Ventura M, et aL, "Imaging-Based Assessment of the Treatment Efficacy of Nanoliposomal Irinotecan (nal-IRI) in a Triple Negative Breast Cancer Model of Spontaneous Metastasis." Poster presented at Annual World Molecular Imaging Congress, Sep. 7-10, 2016, 8 pages.

Von Pawel J, et al., "Randomized Phase III Trial of Amrubicin Versus Topotecan as Second-Line Treatment for Patients with Small-Cell Lung Cancer," J Clin Oncol. 32(35):4012-9 and appendix (1 p.) (2014).

Von Pawel J, et aL, "Topotecan Versus Cyclophosphamide, Doxorubicin, and Vincristine for the Treatment of Recurrent Small-Cell Lung Cancer," J Clin Oncol. 17(2):658-67 (1999).

Wählby C, et al., "Sequential Immunofluorescence Staining and Image Analysis for Detection of Large Numbers of Antigens in Individual Cell Nuclei," Cytometry. 47(1):32-41 (2002).

Zander S, et al., "EZN-2208 (PEG-SN38) Overcomes ABCG2-Mediated Topotecan Resistance in BRCA1-Deficient Mouse Mammary Tumors," PLoS One. 7(9):345248 (2012), pp. 1-9.

Zhang Y, et al. "Poly(ADP-ribose) Polymerase and XPF-ERCC1 Participate in Distinct Pathways for the Repair of Topoisomerase I-Induced DNA Damage in Mammalian Cells," Nucleic Acids Res. 39(9):3607-20 (2011).

Zhao M, et al., "Clinical Observation of Irinotecan or Topotecan as Second-Line Chemotherapy on Treating 43 Patients with Small-Cell Lung Cancer," Chin Oncol. 21(2):156-8 (2011), text in Chinese with Tables 1-3 and Figure 1 in English.

Zheng J, et al., "[18F]FAZA-PET Detection of Hypoxia Changes following Anti-cancer Therapy." Poster presented at Annual World Molecular Imaging Congress, Sep. 18-21, 2013, 7 pages.

Zheng J, et al., "Longitudinal Tumor Hypoxia Imaging with 18F FAZA-PET Provides Early Prediction of Nanoliposomal Innotecan (nal-IRI) Treatment Activity," EJNMMI Res 5(11:57, 10 pages (2015).

Zhou X, et al., "Clinical Analysis of Bevacizumab Plus FOLFIRI Regimen as Front-Line Therapy for Chinese Patients with Advanced Colorectal Cancer," J Cancer Ther 2(4):470-4 (2011).

Znojek P. et al., "Preferential Potentiation of Topoisomerase I Poison Cytotoxicity by PARP Inhibition in S Phase," Br J Cancer. 111(7):1319-26 (2014).

Sohal D, et. al., "Reply to A. Wang-Gillam et al," J Clin Oncol. 35(6):690-1 (2017). Epub 2016.

Son J, et al., "Glutamine Supports Pancreatic Cancer Growth Through a Kras-Regulated Metabolic Pathway," Nature. 496(7443):101-5 (2013), author manuscript version, 16 pages.

Sousa C and Kimmelman A, "The Complex Landscape of Pancreatic Cancer Metabolism," Carcinogenesis. 35 (7):1441-50 (2014).

Starling N, et. al., "A Dose Escalation Study of Gemcitabine Plus Oxaliplatin in Combination With Imatinib for Gemcitabine-Refractory Advanced Pancreatic Adenocarcinoma," Ann Oncol. 23(4):942-7 (2012). Epub 2011.

Stathis A and Moore M, "Advanced Pancreatic Carcinoma: Current Treatment and Future Challenges," Nat Rev Clin Oncol. 7(3):163-72 (2010).

Stathopoulos G, et. al., "A Multicenter Phase III Trial Comparing Irinotecan-Gemcitabine (IG) With Gemcitabine (G) Monotherapy as First-Line Treatment in Patients With Locally Advanced or Metastatic Pancreatic Cancer," Br J cancer. 95(5):587-92 (2006).

Stathopoulos G, et. al., "Lipsomal Cisplatin Combined With Gemcitabine in Pretreated Advanced Pancreatic Cancer Patients: A phase I-II Study," Oncol Rep. 15(5):1201-4 (2006).

Takada T et. al., "Comparison of 5-Fluorouracil, Doxorubicin and Mitomycin C with 5-Fluorouracil Alone in the Treatment of Pancreatic-Biliary Carcinomas," Oncology. 51(5):396-400 (1994).

Takahara N, et. al., "A Retrospective Study of S-1 and Oxaliplatin Combination Chemotherapy in Patients With Refractory Pancreatic Cancer," Cancer Chemother Pharmacol. 72(5):985-90 (2013).

Tempero M, et. al., "NCCN Clinical Practice Guidelines in Oncology: Pancreatic Adenocarcinoma," Version 1.2012. National Comprehensive Cancer Network, Inc. (2011), 79 pages.

Tempero M, et. al., "NCCN Clinical Practice Guidelines in Oncology: Pancreatic Adenocarcinoma," Version 2.2012. National Comprehensive Cancer Network, Inc. (2011), 94 pages.

Tempero M, et. al., "NCCN Clinical Practice Guidelines in Oncology: Pancreatic Adenocarcinoma," Version 2.2014. National Comprehensive Cancer Network, Inc. (2014), 122 pages.

Tempero M, et. al., "Pancreatic Adenocarcinoma: Clinical Practice Guidelines in Oncology," J Natl Compr Canc Netw. 8(9):972-1017 (2010).

Thota R, et. al., "Treatment of Metastatic Pancreatic Adenocarcinoma: A Review," Oncology. 28(1):70-4 (2014). Available at cancernetwork.com/view/treatment-metastatic-pancreatic-adenocarcinoma-review, 6 printed pages.

Todaka A, et. al., "S-1 Monotherapy as Second-line Treatment for Advanced Pancreatic Cancer after Gemcitabine Failure," Jpn J Clin Oncol. 40(6):567-72 (2010).

Togawa A, et. al., "Treatment With an Oral Fluoropyrimidine, S-1, Plus Cisplatin in Patients Who Failed Postoperative Gemcitabine Treatment for Pancreatic Cancer A Pilot Study," Int J Clin Oncol. 12(4):268-73 (2007).

Tomicki S, et al., "Utilization of Hospital Inpatient Services Among Patients With Metastatic Pancreatic Cancer With Commercial and Medicare Insurance Treated With FDA-Approved/NCCN Category 1 Regimens." Poster presented at the Academy of Managed Care Pharmacy, Nexus (AMCP, Nexus): virtual meeting, week of Oct. 19, 2020, 6 pages.

Van Cutsem E et. al., "Phase III Trial of Bevacizumab in Combination With Gemcitabine and Erlotinib in Patients With Metastatic Pancreatic Cancer," J Clin Oncol. 27(13):2231-7 (2009).

Van Rijswijk R, et. al., "Weekly High-Dose 5-Fluorouracil and Folinic Acid in Metastatic Pancreatic Carcinoma: A Phase II Study of the EORTC Gastrointestinal Tract Cancer Cooperative Group," Eur J Cancer. 40(14):2077-81 (2004).

Ventura M, et al., "Efficacy of nal-IRI and Hypoxia Modulation in Orthotopic Patient-Derived Pancreatic Tumor Models of High (OCIP51) and Low (OCIP19) Hypoxia," Presentation presented at the World Molecular Imaging congress 2017, Philadelphia, Pennsylvania, Sep. 13-16, 2017, 15 pages.

Ventura M, et al., Abstract. "Efficacy of nal-IRI and Hypoxia Modulation in Orthotopic Patient-Derived Pancreatic Tumor Models of High (OCIP51) and Low (OCIP19) Hypoxia," the World Molecular Imaging Congress 2017, Philadelphia, Pennsylvania, Sep. 13-16, 2017, 1 page.

Vickers M, et. al., "Comorbidity, Age and Overall Survival in Patients With Advanced Pancreatic Cancer—Results from NCIC CTG PA.3: A Phase III Trial of Gemcitabine Plus Erlotinib or Placebo," Eur J Cancer. 48(10):1434-42 (2012). Epub 2011.

Von Hoff D, et. al., "Gemcitabine Plus nab-Paclitaxel Is an Active Regimen in Patients With Advanced Pancreatic Cancer: A PhaseI/II Trial," J Clin Oncol. 29(34):4548-54 (2011).

Von Hoff D, et. al., "Increased Survival in Pancreatic Cancer with nab-Paclitaxel plus Gemcitabine," N Engl J Med. 369(18):1691-1703 (2013).

Wainberg Z, et al., "First-Line Liposomal Irinotecan + 5-Fluorouracil/Leucovorin + Oxaliplatin in Patients With Pancreatic Ductal Adenocarcinoma: Long-Term Follow-Up Results From a Phase 1/2 Study." Poster presented at the European Society for Medical Oncology (ESMO) World Congress on Gastrointestinal Cancer, virtual format, Jul. 1-4, 2020, 7 pages.

Wainberg Z, et al., "NAPOLI-3: An Open-Label, Randomized, Phase 3 Study of First-Line Liposomal Irinotecan +5 Fluorouracil/Leucovorin + Oxaliplatin Versus Nab-Paclitaxel + Gemcitabine in Patients With Metastatic Pancreatic Ductal Adenocarcinoma." Poster presented at the American Society of Clinical Oncology (ASCO) Annual Conference, virtual format, May 29-Jun. 2, 2020, 6 pages.

Wainberg Z, et al., Abstract TPS4661. "NAPOLI-3: An Open-Label, Randomized, Phase III Study of First-Line Liposomal Irinotecan + Fluorouracil/Leucovorin + Oxaliplatin Versus Nab-Paclitaxel + Gemcitabine in Patients With Metastatic Pancreatic Ductal Adenocarcinoma," J Clin Oncol. 38(15_Suppl):TPS4661 DOI: 10.1200/JCO.2020.38.15_suppl.TPS4661 (2020), 2 printed pages.

(56) References Cited

OTHER PUBLICATIONS

Walker E and Ko A, "Beyond First-Line Chemotherapy for Advanced Pancreatic Cancer: An Expanding Array of Therapeutic Options?" World J Gastroenterol. 20(9):2224-36 (2014).

Wang-Gillam A, et aL, "Characteristics of Long-Term Survivors in a Randomized Phase 3 Trial (NAPOLI-1) of Patients With Metastatic Pancreatic Ductal Adenocarcinoma (mDPAC) Treated With Liposomal Irinotecan (nal-IRI; MM-398) + 5-FU/LV." Poster presented at the American Society of Clinical Oncology Gastrointestinal Cancers Symposium (ASCO GI), San Francisco, CA, Jan. 19-21, 2017, 9 pages.

Wang-Gillam A, et al., "Dose Modifications of Liposomal Irinotecan (nal-IRI) + 5-Fluorouracil/Leucovorin (5-FU/LV) in NAPOLI-1: Impact on Efficacy." Poster presented at the American Society of Clinical Oncology Gastrointestinal Cancers Symposium (ASCO GI), San Francisco, CA, Jan. 18-20, 2018, 8 pages.

Wang-Gillam A, et al., "Nomogram for Predicting Overall Survival in Patients Treated With Liposomal Irinotecan (nal-IRI) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1." Poster presented at the American Society of Clinical Dncology Gastrointestinal Cancers Symposium (ASCO GI), San Francisco, CA, Jan. 18-20, 2018, 9 pages.

Wang-Gillam A, et al., "Updated Overall Survival Analysis of NAPOLI-1: Phase 3 Study of Nanoliposomal Irinotecan (nal-IRI, MM-398), With or Without 5-Fluorouracil and Leucovorin (5-FU/LV), Versus 5-FU/LV in Metastatic Pancreatic cancer (mPAC) Previously Treated With Gemcitabine-Based Therapy." Poster presented at the American Society of clinical Oncology Gastrointestinal Cancers Symposium (ASCO GI), San Francisco, CA, Jan. 21-23, 2016, 11 pages.

Wang-Gillam A, et al., "Updated Overall Survival Analysis of NAPOLI-1: Phase 3 Study of Nanoliposomal Irinotecan nal-IRI, MM-398), With or Without 5-Fluorouracil and Leucovorin, vs 5-Fluorouracil and Leucovorin in Metastatic Pancreatic Ductal Adenocarcinoma Previously Treated With Gemcitabine." Poster presented at the American Society pf Clinical Oncology (ASCO) Annual Meeting, Chicago, Illinois, Jun. 3-7, 2016, 8 pages.

Wang-Gillam A, et al., Abstract 293. "Characteristics of Long-Term Survivors in a Randomized Phase III Trial (NAPOLI-1) of Patients With Metastatic Pancreatic Ductal Adenocarcinoma (mPDAC) Treated With Liposomal rinotecan (nal-IRI; MM-398) + 5-FU/LV," J Clin Oncol. 35(4_Suppl):293 DOI: 10.1200/JCO.2017.35.4_suppl.293 :2017), 2 printed pages.

Wang-Gillam A, et al., Abstract 388. "Dose Modifications of Liposomal Irinotecan (nal-IRI) + 5-Fluorouracil/Leucovorin (5-FU/LV) in NAPOLI-1: Impact on Efficacy," J Clin Oncol. 36(4_Suppl):388 Doi: 10.1200/JCO.2018.36.4_suppl.388 (2018), 2 printed pages.

Wang-Gillam A, et al., Abstract 4126. "Updated Overall Survival (OS) Analysis of NAPOLI-1: Phase 3 Study of ganoliposomal Irinotecan (nal-IRI, MM-398), With or Without 5-Fluorouracil and Leucovorin (5-FU/LV), vs 5-FU/LV in Metastatic Pancreatic Cancer (mPAC) Previously Treated With Gemcitabine (Gem)-Based Therapy," J Clin Oncol. 34 (15_Suppl):4126 Doi: 10.1200/JCO.2016.34.15_suppl.4126 (2016), 5 printed pages.

Wang-Gillam A, et al., Abstract 417. "Updated Overall Survival Analysis of NAPOLI-1: Phase III Study of Nanoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Rreated With Gemcitabine-Based Therapy," J Clin Oncol. 34 (4_Suppl):417 Doi: 10.1200/jco.2016.34.4_suppl.417 (2016), 2 printed pages.

Wang-Gillam A, et al., Abstract 459. "Nomogram for Predicting Overall Survival (OS) in Patients (pts) Treated With Liposomal Irinotecan (nal-IRI) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1," J Clin Oncol. 36(4_Suppl):459 DOI: 10.1200/JCO.2018.36.4_suppl.459 (2018), 2 printed pages.

Wang-Gillam A, et al., Abstract e15795. "The Prognostic Value of Baseline Neutrophil-to-Lymphocyte Ratio (NLR) and Platelet-to-Lymphocyte ratio (PLR) for Predicting Clinical Outcome in Patients with Metastatic Pancreatic Ductal Adenocarcinoma (mPDAC) Treated With Liposomal Irinotecan (nalIRl; MM398) + 5-Fluorouracil and Leucovorin (5-Fu/LV) vs 5-FU/LV," J Clin Oncol. 35(15_Suppl):e15795 Doi: 10.1200/JCO.2017.35.15_suppl.e15795 (2017), 3 printed pages.

Wang-Gillam A, et al., Abstract e16204. "A Survival Prediction Nomogram for Liposomal Irinotecan (nal-IRI)+5- Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(15_Suppl):e16204 DOI: 10.12001 JCO.2018.36.15_suppl.e16204 (2018), 2 printed pages.

Wang-Gillam A, et al., letter to editor, "Nanoliposomal Irinotecan in the Clinical Practice Guideline for Metastatic Pancreatic Cancer Applicability to Clinical Situations," J Clin Oncol. 35(6):689-90 (2017). Epub 2016.

Xiong H, et. al., "Phase 2 Trial of Oxaliplatin Plus Capecitabine (XELOX) as Second-line Therapy for Patients With Advanced Pancreatic Cancer," Cancer. 113(8):2046-52 (2008).

Yu K, et al., "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," Poster presented at the Academy of Managed Care Pharmacy, Nexus (AMCP, Nexus): virtual meeting, week of Oct. 19, 2020, 9 pages.

Yu K, et al., Abstract C3. "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," J Manag Care Spec Pharm. 26(10-a):519 (2020).

Yu K, et al., "A US Multicenter Chart Review Study of Patients With Metastatic Pancreatic Ductal Adenocarcinoma Receiving Liposomal Irinotecan after Gemcitabine-Based Therapy." Poster presented at the International Conference on Pharmacoepidemiology & Therapeutic Risk Management (ICPE) All Access, Sep. 16-17, 2020, 8 pages.

Yu K, et al., "Real-World Treatment Patterns and Effectiveness of Liposomal Irinotecan in a Napolii-Based Regimen Among Patients With Metastatic Pancreatic Ductal Adenocarcinoma (mPDAC): A Multi-Academic Center Chart Review." Poster presented at the European Society for Medical Oncology (ESMO) Virtual Congress 2020, Sep. 19-21, 2020, 9 pages.

Yu K, et al., Abstract 1555P. "Real-World Treatment Patterns and Effectiveness of Liposomal Irinotecan in a NAPOLI1-Based Regimen Among Patients With Metastatic Pancreatic Ductal Adenocarcinoma (mPDAC): A Multi-Academic Center Chart Review," Ann Oncol. 31(Suppl_4):5950-5951 doi.org/10.1016/j.annonc_2020.08.2038 (2020), 2 printed pages.

Yu K, et al., Abstract e16733. "A Multicenter Chart Review Study of Patients with Metastatic Pancreatic Ductal Adenocarcinoma Receiving Liposomal Irinotecan after Gemcitabine-Based Therapy," J Clin Oncol. 38(15_Suppl): e16733 DOI: 10.1200/JCO.2020.38.15_suppl.e16733 (2020), 4 printed pages.

Yu K, et al., Abstract P0-3727. "A US Multicenter Chart Review Study of Patients With Metastatic Pancreatic Ductal Adenocarcinoma Receiving Liposomal Irinotecan after Gemcitabine-Based Therapy," International Conference on Pharmacoepidemiology & Therapeutic Risk Management (ICPE), Sep. 14, 2020, available at eventscribe.com/2020/ICPEAllAccess/PosterTitles.asp?pfp=PosterTitles, 1 page.

Yu X, et. al., "Targeted Drug Delivery in Pancreatic Cancer," Biochim Biophys Acta. 21805(1):97-104 (2010). Epub 2009, author manuscript version, 16 pages.

Batist G, et al., "Safety Pharmacokinetics, and Efficacy of CPX-1 Liposome Injection in Patients with Advanced Solid Tumors," Clin Cancer Res. 15(2):692-700 (2009).

Boman N, et al., "Optimization of the Retention Properties of Vincristine in Liposomal Systems," Biochim Biophys Acta. 1152(2):253-58 (1993).

Colbern G, et al., "Encapsulation of the Topoisomerase I Inhibitor GL147211C in Pegylated (Stealth) Liposomes: Pharmacokinetics

(56) References Cited

OTHER PUBLICATIONS and Antitumor Activity in HT29 Colon Tumor Xenografts," Clin Cancer Res. 4(12):3077-82 (1998).

Dicko A, et al., "Intra and Inter-Molecular Interactions Dictate the Aggregation State of Irinotecan Co-Encapsulated with Floxuridine Inside Liposomes," Pharm Res. 25(7):1702-13 (2008).

Drummond D, et al., "Pharmacokinetics and in Vivo Drug Release Rates in Liposomal Nanocarrier Development," J Pharm Sci. 97(11):4696-740 (2008).

Emerson D, et al., "Antitumor Efficacy, Pharmacokinetics, and Biodistribution of NX 211: A Low-Clearance Liposomal Formulation of Lurtotecan," Clin Cancer Res. 6(7):2903-12 (2000).

EP Patent Application No. 05745505.7: European Search Report dated Sep. 1, 2010, 6 pages.

European Medicines Agency Assesment Report for Onivyde, Committee for Medicinal Products for Human Use (CHMP), Jul. 21, 2016, 107 pages.

Fugit K, et al., "The Role of pH and Ring-opening Hydrolysis Kinetics on Liposomal Release of topotecan,"J Control Release. 174:88-97 (2014), Epub Nov. 12, 2021, Author manuscript, pp. 1-27.

Hattori Y, et al., "Novel Irinotecan-Loaded Liposome Using Phytic Acid with High Therapeutic Efficacy for Colon Tumors", J Control Release. 136(1):30-7 (2009).

Pavillard V, et al., "Determinants of the Cytotoxicity of Irinotecan in Two Human Colorectal Tumor Cell Lines," Cancer Chemother Pharmacol. 49(4):329-35 (2002).

Peikov V, et al., "pH-Dependent Association of SN-38 with Lipid Bilayers of a Novel Liposomal Formulation," Int J Pharm. 299(1-2):92-9 (2005).

PharmaEngine, www.pharmaengine.com/pep02.html Webpage titled "PEP02". Aug. 4, 2011, 4 printed pages.

Riviere K, et al., "Anti-Tumor Activity of Liposome Encapsulated Fluoroorotic Acid as a Single Agent and in Combination with Liposome Irinotecan," J Control Release. 153(3):288-96 (2011), Author manuscript, pp. 1-19.

Sadzuka Y, et al., "Effective Irinotecan (CPT-11)-containing Liposomes: Intraliposomal Conversion to the Active Metabolite SN-38." Jpn J Cancer Res. 90(2):226-32 (1999).

Tardi P, et al., "Liposomal Encapsulation of Topotecan Enhances Anticancer Efficacy in Murine and Human Xenograft Models," Cancer Res. 60(13):3389-93 (2000).

Wei H, et al., "Active Loading Liposomal Irinotecan Hydrochloride: Preparation, In Vitro and In Vivo Evaluation," Asian J Pharm Sci. 8(5):303-11 (2013).

Zhang L, et al., PEG-Coated lrinitecan Cationic Liposomes Improve the Therapeutic Efficacy of Breast Cancer in Animals, Eur Rev Med Pharmacol Sci. 17(24):3347-61 (2013).

Activity of MM-398 (Ls-CPT11) in an Orthotopic
Pancreas Tumor Model Expressing Luciferase (L3.6pl).

Accumulation of SN-38 in Tumors Following Treatment
with Free Irinotecan or Nanoliposomal Irinotecan (MM-398).

Effect of MM-398 on Carbonic Anhydrase IX staining in the HT29 xenograft model.

FIG. 5

MM-398 PK in q3w (irinotecan, liposomes + free drug)

| Dose (mg/m²) Study | PEP0203 | | | | PEP0201 | | PEP0206 | | Camptosar | Camptosar Package Insert |
|---|---|---|---|---|---|---|---|---|---|---|
| | 60 | 80 | 100 | 120 | 120 | 180 | 120 | 300 | 125 | 340 |
| Formulation | lipo¹ | lipo¹ | lipo¹ | lipo¹ | lipo² | lipo² | PEP02 | Campto | lipo¹ | lipo¹ |
| $C_{max}$ (ng/ml) | 28.95 (±4.73) | 29.16 (±5.23) | 44.06 (±7.86) | 42.98 (±16.03) | 79.4 (±13.9) | 102 (±47.9) | 60.88 (±9.57) | 3.08 (±1.27) | 1.866 (±0.44) | 3.292 (±0.87) |
| $t_{1/2}$ (h) | 24.882 (±4.750) | 52.69 (±18.23) | 48.11 (±7.46) | 50.01 (±16.05) | 26.5 (±13.9) | 22.3 (±8.7) | 21.2 (±3.3) | 7.7 (±1.2) | 5.8 (±0.79) | 11.7 (±0.875) |
| AUC₀-t (ng*h/ml) | 1,067 (±16.75) | 1,116 (±18.21) | 2,898 (±17.43) | 1,117 (±9.32) | 2,895 (±7.2) | 1,943 (±11.5) | 1,651.5 (±18.3) | 28.2 (±4.4) | 10.2 (±2.7) | 11.7 (±4.0) |
| AUC₀-∞ (ng*h/ml) | 1,114 (±1.27) | 1,211 (±9.24) | 2,472 (±1,017) | 1,291 (±3,088) | 2,989 (±1,947) | 1,969 (±1,085) | 1,981.2 (±1,481.5) | 26.3 (±5.2) | | |
| Cl (L/h/m²) | 0.1249 (±0.1339) | 0.1568 (±0.1568) | 0.0547 (±0.0558) | 0.1035 (±0.04009) | 0.0591 (±0.0467) | 0.119 (±0.0228) | 0.103 (±0.2261) | 12.9 (±9.6) | 13.3 (±0.27) | 13.9 (±4.03) |
| $V_{ss}$ (L/m²) | 2.6 | 2.95 (±0.60) | 2.63 (±0.60) | 3.16 (±0.38) | 1.8 (±0.770) | 1.97 (±0.380) | 2.3 (±0.60) | 96.5 (±230.0) | 118 (±66.01) | 224 (±89.0) |
| (Liter) | (±1.46) | | | | | | | | | |

Note: AUC 0-T is defined as T = 24 hours for Camptosar in the PEP0206 study and T = 48.5 hours for Camptosar in the PEP0206 study and T = 169.6 hours for MM-398.

FIG. 6

Note: AUC 0-T is defined as T = 24 hours for Camptosar package insert, T = 49.3 hours for Camptosar in the PEP0206 study and T = 169.5 hours for MM-398.

MM-398 PK in q3w (SN-38)

| Dose (mg/m²) Study | 60 | 80 | 100 | 120 | 120 | 180 | PEP0202 120 | Camptosar 300 | Camptosar package insert 125 | 340 |
|---|---|---|---|---|---|---|---|---|---|---|
| | PEP0203 | PEP0203 | PEP0203 | PEP0203 | PEP0201 | PEP0201 | | | | |
| Parameters | | | | | | | | | | |
| Cmax (ng/mL) | 7.02 (±5.64) | 7.98 (±4.39) | 7.39 (±1.46) | 16.64 (±9.36) | 9.2 (±3.3) | 14.3 (±4.16) | 8.79 (±9.60) | 44.1 (±26.2) | 28.3 (±11.9) | 58.0 (±26.2) |
| | 103.81 | 53.73 | 73.41 | 26.29 | 73.6 | 58.0 | 88.3 | 22.0 | 10.6 | 21.0 |
| t½ (h) | (±72.3) 367.40 | (±15.8) 358.77 | (±16.3) 531.40 | (±46.5) 367.40 | (±43.0) 710 | (±52.3) 1,160 | (±42.6) 467 | (±16.6) 361 | (±5.1) 220 | (±4.3) 474 |
| AUC0-T (ng/mL·h) | (±277) 1,573.3 | (±84.0) 500.18 | (±383.3) 844.28 | (±4155.7) 494.00 | (±1892) 997 | (±999) 1,400 | (±210) 579 | (±125) 460 | (±5.00) | (±5.00) |
| AUC0-∞ (ng/mL·h) | (±1189) | (±153) | (±644) | (±2500) | (±690) | (±1150) | (±1420) | (±140) | | |

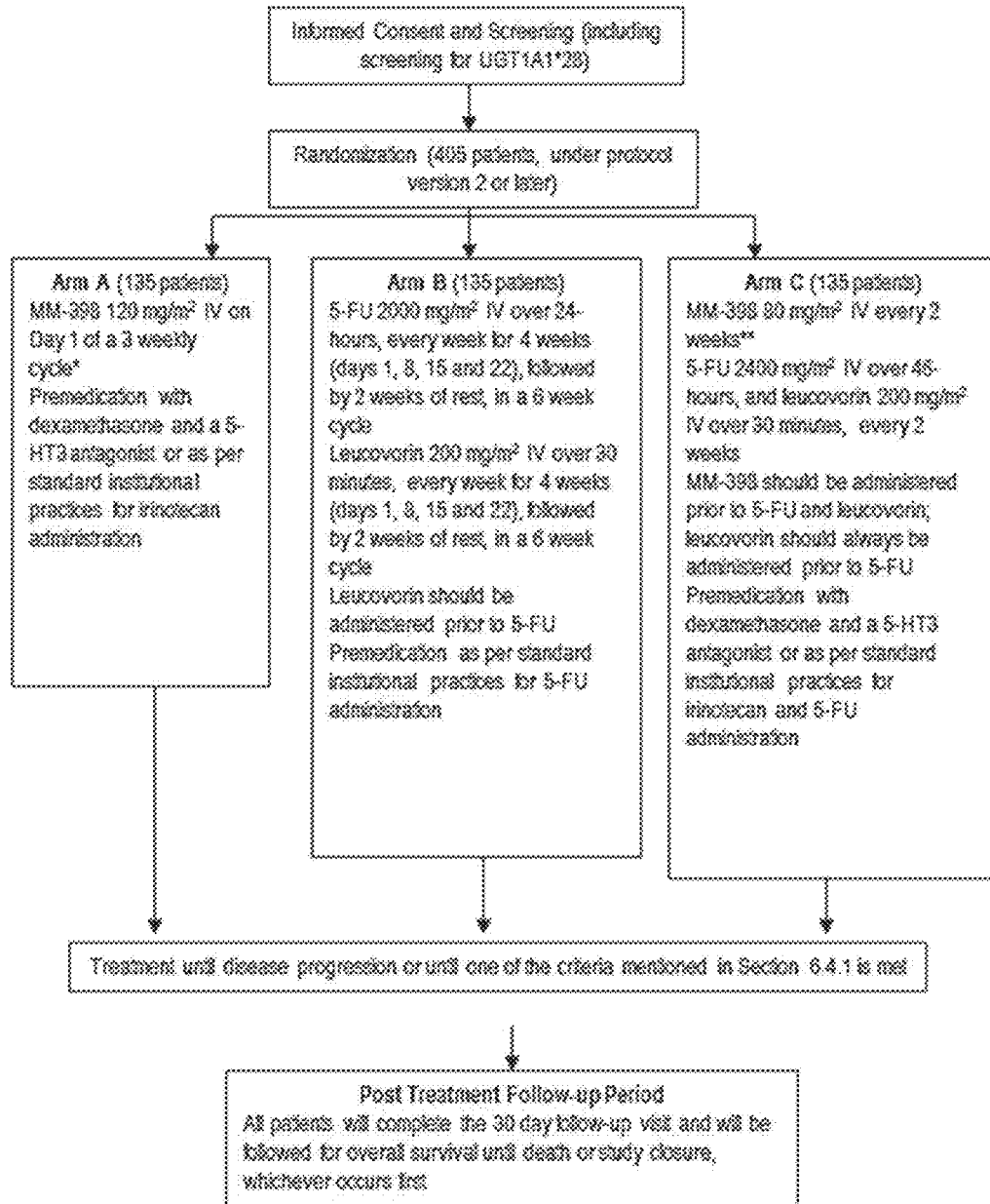

FIG. 7

* Patients who are homozygous for UGT1A1*28 allele and are randomized to Arm A, will receive the first cycle of therapy at a reduced dose of 80 mg/m2. If the patient does not experience any drug related toxicity after the first administration of MM-398, from cycle 2 onwards, the dose may be increased in increments of 20 mg/m2, up to a maximum of 120 mg/m2.
** Patients who are homozygous for UGT1A1*28 allele and are randomized to Arm C, will receive the first cycle of therapy at a reduced dose of 60 mg/m2. If the patient does not experience any drug related toxicity after the first administration of MM-398, from cycle 2 onwards, the dose may be increased to 80 mg/m2.

METHODS FOR TREATING PANCREATIC CANCER USING COMBINATION THERAPIES COMPRISING LIPOSOMAL IRINOTECAN

CROSS-REFERENCE TO RELATED APPLICATIONS

This application is a continuation of U.S. application Ser. No. 15/652,513, filed Jul. 18, 2017, which is a continuation of U.S. application Ser. No. 15/341,377, filed Nov. 2, 2016, which is a continuation of U.S. application Ser. No. 14/851,111, filed Sep. 11, 2015 (now U.S. Pat. No. 9,492,442), which is a continuation of U.S. application Ser. No. 14/406,776, filed Dec. 10, 2014 (now U.S. Pat. No. 9,452,162), which is a 35 U.S.C. § 371(c) United States National Phase of PCT/US2013/045495, filed Jun. 12, 2013, which claims the benefit of priority of U.S. Provisional Application No. 61/659,211, filed Jun. 13, 2012, and U.S. Provisional Application No. 61/784,382, filed Mar. 14, 2013, all of which are incorporated herein by reference in their entireties.

BACKGROUND

Despite improvements in cancer treatments, there remains a critical need to further improve therapies so as to prolong patients' lives while maintaining quality of life, particularly in the case of advanced cancers such as pancreatic cancers that often are, or become, resistant to current therapeutic modalities.

Incidence of pancreatic cancer has markedly increased during the past several decades. It now ranks as the fourth leading cause of cancer death in the United States. Pancreatic cancer's high mortality rate is due to a dearth of effective therapies and a complete absence of reliably durable therapies. Because of the location of the pancreas, pancreatic cancer is typically not diagnosed until a tumor has become large enough to produce systemic symptoms. This, coupled with the absence of good screening tools and a limited understanding of risk factors, results in patients usually having advanced disease, often advanced metastatic disease, at the time of diagnosis. Metastatic pancreatic cancer has a dismal prognosis and is almost uniformly fatal, with an overall survival rate of less than 4% at 5 years.

Chemotherapy with one or more of 5-fluorouracil (5-FU) and gemcitabine has been shown to prolong survival in pancreatic cancer. Combination therapies including folinic acid (leucovorin or levoleucovorin), 5-fluorouracil, and irinotecan (FOLFIRI), folinic acid, 5-fluorouracil, irinotecan and oxaliplatin (FOLFIRINOX), or, less commonly, a combination of folinic acid, 5-fluorouracil, and oxaliplatin (FOLFOX) are also used to treat some pancreatic cancers. Irinotecan is 7-ethyl-10-[4-(1-piperidino)-1-piperidino] carbonyloxycampothecin, IUPAC name (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate. Irinotecan is a member of the topoisomerase I inhibitor class of drugs and is a semi-synthetic and water soluble analog of the naturally-occurring alkaloid, camptothecin. Also known as CPT-11, irinotecan is currently marketed formulated as an aqueous solution as Camptosar® (irinotecan hydrochloride injection). Topoisomerase I inhibitors such as irinotecan work to arrest uncontrolled cell growth by inhibiting the unwinding of DNA and thereby preventing DNA replication.

The pharmacology of irinotecan is complex, with extensive metabolic conversions involved in the activation, inactivation, and elimination of the drug. Irinotecan is a prodrug that is converted by nonspecific carboxylesterases into a 100-1000 fold more active metabolite, SN-38. SN-38 is not recognized by P-glycoprotein, a drug transporter that plays an important role in acquired drug resistance by pumping certain drugs out of cells, so irinotecan is likely to be active in tumors resistant to other standard chemotherapies. In the body, SN-38 is cleared via glucuronidation, for which major pharmacogenetic variability has been described, and biliary excretion. These drug properties contribute to the marked heterogeneities in efficacy and toxicity observed clinically with irinotecan. Irinotecan hydrochloride injection is approved in the United States for treatment of metastatic colon or renal cancer and is also used to treat colorectal, gastric, lung, uterine cervical and ovarian cancers.

There are few approved treatment options for advanced or metastatic pancreatic cancers, particularly for those of exocrine origin. Single-agent gemcitabine is the current standard of care in first-line treatment of advanced and metastatic pancreatic adenocarcinoma. In clinical trials, single-agent gemcitabine has consistently demonstrated a median prolongation of survival of 5 to 6 months and a 1-year survival rate of about 20%. Single agent gemcitabine was also approved as second line treatment for patients previously treated with but no longer responsive to 5-fluorouracil, with a median overall prolongation of survival of 3.9 months.

Based upon what is known of the biology of pancreatic cancer, a variety of targeted agents have been evaluated, but only erlotinib, a protein tyrosine kinase inhibitor targeted to EGFR, has been approved for first-line use in advanced pancreatic cancer, and the approval is only for use in combination with gemcitabine. The co-administration of erlotinib with gemcitabine resulted in a statistically significant benefit in survival, and improvements in median survival (6.4 months vs. 5.9 months), and 1-year survival rate (24% vs. 17%) compared to gemcitabine alone. Clinical trials evaluating other targeted agents, including studies testing the antibodies bevacizumab and cetuximab, have been disappointingly negative. Thus, there is an urgent need for improvements in, and effective alternatives to, current therapies for pancreatic cancer. The disclosed invention addresses this need and provides other benefits.

SUMMARY

Provided are methods for treating pancreatic cancer in a patient (i.e., a human patient) comprising administering to the patient liposomal irinotecan (e.g., irinotecan sucrose octasulfate salt liposome injection, also referred to as MM-398) alone or in combination with 5-fluorouracil (5-FU) and leucovorin (together, 5-FU/LV), according to a particular clinical dosage regimen. Compositions adapted for use in such methods are also provided.

In one aspect, a method for treatment (e.g., effective treatment) of pancreatic cancer in a patient is provided, the method comprising: administering to the patient, and affective amount of liposomal irinotecan, wherein the method comprises at least one cycle, wherein the cycle is a period of 3 weeks, and wherein for each cycle the liposomal irinotecan is administered on day 1 of the cycle at a dose of 120 mg/m$^2$, except if the patient is homozygous for the UGT1A1*28 allele, wherein liposomal irinotecan is administered on day 1 of cycle 1 at a dose of 80 mg/m$^2$. In one embodiment, the dose of liposomal irinotecan administered to the patient homozygous for the UGT1A1*28 allele is increased after one cycle in increments of 20 mg/m$^2$, up to a maximum of 120 mg/m$^2$.

In another aspect, a method for treatment of pancreatic cancer in a patient is provided, the method comprising co-administering to the patient an effective amount each of liposomal irinotecan, 5-fluorouracil (5-FU), and leucovorin, wherein the method comprises at least one cycle of administration, wherein the cycle is a period of 2 weeks, and wherein for each cycle:

(a) liposomal irinotecan is administered to patients not homozygous for the UGT1A1*28 allele on day 1 of each cycle at a dose of 80 mg/m$^2$, and to patients homozygous for the UGT1A1*28 allele on day 1 of cycle 1 at a dose of 60 mg/m$^2$ and on day 1 of each subsequent cycle at a dose of ranging from 60 mg/m$^2$ to 80 mg/m$^2$ (e.g., 60 mg/m$^2$ or 70 mg/m$^2$ or 80 mg/m$^2$);

(b) 5-FU is administered at a dose of 2400 mg/m$^2$; and (c) leucovorin is administered at a dose of 200 mg/m$^2$ (1 form, or levoleucovorin) or 400 mg/m$^2$ (l+d racemic form). In one embodiment, the dose of liposomal irinotecan administered to the patient homozygous for the UGT1A1*28 allele is increased after one cycle to 80 mg/m$^2$. In one embodiment, in each cycle, the liposomal irinotecan is administered prior to the leucovorin and the leucovorin is administered prior to the 5-FU.

In another embodiment, the liposomal irinotecan is administered intravenously over 90 minutes.

In another embodiment, the 5-FU is administered intravenously over 46 hours.

In another embodiment, leucovorin is administered intravenously over 30 minutes.

In another embodiment, prior to each administration of liposomal irinotecan, the patient is pre-medicated with dexamethasone and/or a 5-HT3 antagonist or another antiemetic.

In another embodiment, the pancreatic cancer is an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

In one embodiment, treating the patient results in a positive outcome, wherein the positive outcome is pathologic complete response (pCR), complete response (CR), partial response (PR) or stable disease (SD). In another embodiment, the combination therapy with liposomal irinotecan, 5-FU and leucovorin results in therapeutic synergy. In another embodiment, the liposomal irinotecan is formulated as irinotecan sucrose octasulfate salt liposome injection (MM-398). Irinotecan sucrose octasulfate salt liposome injection may also be referred to as irinotecan HCl liposome injection because irinotecan HCl is the active pharmaceutical ingredient that is used to load irinotecan into liposomes containing triethylammonium sucrose octasulfate to prepare MM-398 liposomes. This nomenclature may be used even though the hydrochloride ion of the irinotecan HCl reacts with the triethylammonium ion of the triethylammonium sucrose octasulfate to yield triethylammonium chloride (triethylamine hydrochloride), leaving irinotecan sucrose octasulfate salt as the entrapped pharmaceutical agent within the MM-398 liposomes. In another aspect, kits for treating pancreatic cancer in a patient are provided, the kit comprising a dose of liposomal irinotecan and instructions for using liposomal irinotecan as described herein.

In another aspect, kits for treating pancreatic cancer in a patient are provided, the kit comprising a dose of each liposomal irinotecan, 5-fluorouracil (5-FU), and leucovorin, and instructions for using liposomal irinotecan, 5-FU, and leucovorin as described herein.

In one embodiment, the kit encompasses treating an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

In one embodiment, the liposomal irinotecan is liposomal irinotecan sucrose octasulfate salt injection (MM-398).

In another aspect, a formulation of liposomal irinotecan for co-administration with 5-fluorouracil (5-FU) and leucovorin in at least one cycle is provided, wherein the cycle is a period of 2 weeks, the formulation of irinotecan is a liposomal formulation of irinotecan, and wherein:

(a) liposomal irinotecan is administered to patients not homozygous for the UGT1A1*28 allele on day 1 of each cycle at a dose of 80 mg/m$^2$ and to patients homozygous for the UGT1A1*28 allele on day 1 of cycle 1 at a dose of 60 mg/m$^2$ and on day 1 of each subsequent cycle at a dose of 60 mg/m$^2$ or 80 mg/m$^2$;

(b) 5-FU is administered at a dose of 2400 mg/m$^2$; and (c) leucovorin is administered at a dose of 200 mg/m$^2$ (1 form, or levoleucovorin) or 400 mg/m$^2$ (l+d racemic form).

In one embodiment, after cycle 1 the dose of liposomal irinotecan administered to the patient homozygous for the UGT1A1*28 allele is increased to 80 mg/m$^2$. In another embodiment, the liposomal irinotecan is administered intravenously over 90 minutes.

In another embodiment, the 5-FU is administered intravenously over 46 hours.

In another embodiment, leucovorin is administered intravenously over 30 minutes.

In another embodiment, prior to each administration of liposomal irinotecan, the patient is pre-medicated with dexamethasone and/or a 5-HT3 antagonist or another antiemetic.

In another embodiment, the pancreatic cancer is an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

In another embodiment, the liposomal formulation of irinotecan is irinotecan sucrose octasulfate salt liposome injection.

In another aspect is provided a method of improving chemotherapy outcomes by increasing tumor vascularity, the method comprising administering to a patient having a tumor an amount of irinotecan sucrose octasulfate salt liposome injection effective to increase tumor vascularity and concomitantly administering an effective amount of a chemotherapy agent other than irinotecan to the patient.

In another aspect is provided irinotecan sucrose octasulfate salt liposome injection for concomitant administration to a patient having a tumor of 1) an amount of irinotecan sucrose octasulfate salt liposome injection effective to increase tumor vascularity and 2) an effective amount of a chemotherapy agent other than irinotecan.

BRIEF DESCRIPTION OF THE DRAWINGS

FIG. 5 summarizes the pharmacokinetics of MM-398 in q3w (irinotecan, liposome+free drug).

FIG. 6 summarizes the pharmacokinetics of MM-398 in q3w.

FIG. 7 is a schematic illustration of a Phase 3 study design.

DETAILED DESCRIPTION

I. Definitions

Figure 1:
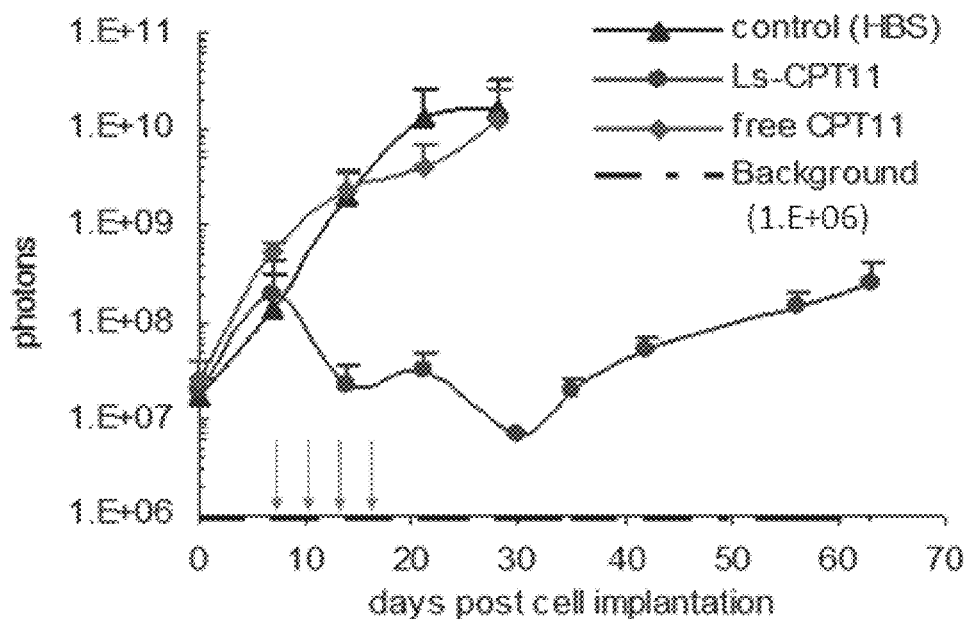
FIG. 1 is a graph showing the anti-tumor activity of MM-398 in an orthotopic pancreatic tumor model expressing luciferase (L3.6pl).

As used herein, the term "subject" or "patient" is a human cancer patient.

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, slowing, retarding, or stabilizing of a deleterious progression of a marker of a cancer. Effective treatment may refer to alleviation of at least one symptom of a cancer. Such effective treatment may, e.g., reduce patient pain, reduce the size and/or number of lesions, may reduce or prevent metastasis of a cancer tumor, and/or may slow growth of a cancer tumor.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to cancers, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit (i.e., slow to some extent and may stop) tumor metastasis; (v) inhibit tumor growth; (vi) prevent or delay occurrence and/or recurrence of tumor; and/or (vii) relieve to some extent one or more of the symptoms associated with the cancer.

The terms "combination therapy," "co-administration," "co-administered" or "concurrent administration" (or minor variations of these terms) include simultaneous administration of at least two therapeutic agents to a patient or their sequential administration within a time period during which the first administered therapeutic agent is still present in the patient when the second administered therapeutic agent is administered.

The term "monotherapy" refers to administering a single drug to treat a disease or disorder in the absence of co-administration of any other therapeutic agent that is being administered to treat the same disease or disorder.

"Dosage" refers to parameters for administering a drug in defined quantities per unit time (e.g., per hour, per day, per week, per month, etc.) to a patient. Such parameters include, e.g., the size of each dose. Such parameters also include the configuration of each dose, which may be administered as one or more units, e.g., taken at a single administration, e.g., orally (e.g., as one, two, three or more pills, capsules, etc.) or injected (e.g., as a bolus). Dosage sizes may also relate to doses that are administered continuously (e.g., as an intravenous infusion over a period of minutes or hours). Such parameters further include frequency of administration of separate doses, which frequency may change over time.

"Dose" refers to an amount of a drug given in a single administration.

As used herein, "cancer" refers to a condition characterized by abnormal, unregulated, malignant cell growth. In one embodiment, the cancer is an exocrine pancreatic cancer. In another embodiment, the exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

The terms "resistant" and "refractory" refer to tumor cells that survive treatment with a therapeutic agent. Such cells may have responded to a therapeutic agent initially, but subsequently exhibited a reduction of responsiveness during treatment, or did not exhibit an adequate response to the therapeutic agent in that the cells continued to proliferate in the course of treatment with the agent.

II. Irinotecan Sucrose Sulfate Liposome Injection (MM-398; PEP02)

As provided herein, irinotecan is administered in a stable liposomal formulation as irinotecan sucrose sulfate liposome injection (otherwise termed "irinotecan sucrose octasulfate salt liposome injection" or "irinotecan sucrosofate liposome injection"), the formulation referred to herein as "MM-398" (also known as PEP02, see U.S. Pat. No. 8,147,867). MM-398 may be provided as a sterile, injectable parenteral liquid for intravenous injection. The required amount of MM-398 may be diluted, e.g., in 500 mL of 5% dextrose injection USP and infused over a 90 minute period.

An MM-398 liposome is a unilamellar lipid bilayer vesicle of approximately 80-140 nm in diameter that encapsulates an aqueous space which contains irinotecan complexed in a gelated or precipitated state as a salt with sucrose octasulfate. The lipid membrane of the liposome is composed of phosphatidylcholine, cholesterol, and a polyethyleneglycol-derivatized phosphatidyl-ethanolamine in the amount of approximately one polyethyleneglycol (PEG) molecule for 200 phospholipid molecules.

This stable liposomal formulation of irinotecan has several attributes that may provide an improved therapeutic index. The controlled and sustained release improves activity of this schedule-dependent drug by increasing duration of exposure of tumor tissue to drug, an attribute that allows it to be present in a higher proportion of cells during the S-phase of the cell cycle, when DNA unwinding is required as a preliminary step in the DNA replication process. The long circulating pharmacokinetics and high intravascular drug retention in the liposomes can promote an enhanced permeability and retention (EPR) effect. EPR allows for deposition of the liposomes at sites, such as malignant tumors, where the normal integrity of the vasculature (capillaries in particular) is compromised resulting in leakage out of the capillary lumen of particulates such as liposomes. EPR may thus promote site-specific drug delivery of liposomes to solid tumors. EPR of MM-398 may result in a subsequent depot effect, where liposomes accumulate in tumor associated macrophages (TAMs), which metabolize irinotecan, converting it locally to the substantially more cytotoxic SN-38. This local bioactivation is believed to result in reduced drug exposure at potential sites of toxicity and increased exposure at cancer cells within the tumor.

Pharmacogenetics of Irinotecan Glucuronidation

The enzyme produced by the UGT1A1 gene, UDP-glucuronosyltransferase 1, is responsible for bilirubin metabolism and also mediates SN-38 glucuronidation, which is the initial step in the predominant metabolic clearance pathway of this active metabolite of irinotecan. Besides its anti-tumor activity, SN-38 is also responsible for the severe toxicity sometimes associated with irinotecan therapy. Therefore, the glucuronidation of SN-38 to the inactive form, SN-38 glucuronide, is an important step in the modulation of irinotecan toxicity.

Mutational polymorphisms in the promoter of the UGT1A1 gene have been described in which there is a variable number of thymine adenine (ta) repeats. Promoters containing seven thymine adenine (ta) repeats (found in the UGT1A1*28 allele) have been found to be less active than the wild-type six repeats, resulting in reduced expression of UDP-glucuronosyltransferase 1. Patients who carry two deficient alleles of UGT1A1 exhibit reduced glucuronidation of SN-38. Some case reports have suggested that individuals who are homozygous for UGT1A1*28 alleles (referred to as having the UGT1A1 7/7 genotype, because both alleles are UGT1A1*28 alleles that contain 7 ta repeats, as opposed to the wild-type UGT1A1 6/6 genotype in which both alleles contain 6 ta repeats) and who have fluctuating elevation in serum bilirubin, (e.g., Gilbert's Syndrome patients), may be at greater risk of toxicity upon receiving standard doses of irinotecan. This suggests that there is a link between homozygosity of the UGT1A1*28 allele, bilirubin levels and irinotecan toxicity.

The metabolic transformation of MM-398 to SN-38 (e.g., in plasma) includes two critical steps: (1) the release of irinotecan from the liposome and (2) the conversion of free irinotecan to SN-38. While not intending to be limited by theory, it is believed that once irinotecan leaves the liposomes, it is catabolized by the same metabolic pathways as conventional (free) irinotecan. Therefore the genetic polymorphisms in humans predictive for the toxicity and efficacy of irinotecan and those of MM-398 can be considered similar. Nonetheless, due to the smaller tissue distribution, lower clearance, higher systemic exposure and longer elimination half-life of SN-38 of the MM-398 formulation compared to free irinotecan, the deficient genetic polymorphisms may show more association with severe adverse events and/or efficacy.

Patients with Reduced UGT1A1 Activity

Individuals who are homozygous for the UGT1A1*28 allele (UGT1A1 7/7 genotype) have been shown to be at increased risk for neutropenia following initiation of irinotecan treatment. According to the prescribing information for irinotecan (Camptosar®), in a study of 66 patients who received single-agent irinotecan (350 mg/m$^2$ once every-3-weeks), the incidence of grade 4 neutropenia in patients homozygous for the UGT1A1*28 allele was as high as 50%, and in patients heterozygous for this allele (UGT1A1 6/7 genotype) the incidence was 12.5%. Importantly, no grade 4 neutropenia was observed in patients homozygous for the wild-type allele (UGT1A1 6/6 genotype). In other studies, a lower prevalence of life threatening neutropenia is described. For this reason, patients who are enrolled in the phase 3 study described in the Examples herein and are homozygous for the UGT1A1*28 allele (UGT1A1 7/7 genotype) will have MM-398 treatment initiated at a lower dose than patients with one (e.g., UGT1A1 6/7) or two (UGT1A1 6/6) wild-type alleles.

Additional Genotypic Modifiers of Irinotecan Metabolism

Although the UGT1A1*28 allele is relatively common in Caucasians (estimates 10%), the prevalence is varied in other ethnic groups. Furthermore, additional UGT1A1 genotypes are found with higher prevalence for example in Asian populations and these could be important for the metabolism of irinotecan in these populations. For example, the UGT1A1*6 allele is more prevalent in Asians. This allele is not associated with a ta repeat, but with a Gly71Arg mutation that reduces enzyme activity. In previous and ongoing studies of MM-398, pharmacogenetic information has been collected on patients being enrolled. In a study referred to as the PEP0203 study, the relationship of genetic polymorphism of UGT1A family and of DPYD (dihydropyrimidine dehydrogenase, an enzyme associated with catabolism of 5-FU) with pharmacokinetic parameters of MM-398 and toxicity did not provide a clear correlation with the small sample size of subjects evaluated. However, it was observed that patients with UGT1A1*6/*28 combined polymorphism had higher dose-normalized AUCs of SN-38 and experienced DLT.

III. 5-Fluorouracil (5-FU) and Leucovorin

5-Fluorouracil is a pyrimidine antagonist that interferes with nucleic acid biosynthesis. The deoxyribonucleotide of the drug inhibits thymidylate synthetase, thus inhibiting the formation of thymidylic acid from deoxyuridylic acid, thus interfering in the synthesis of DNA. It also interferes with RNA synthesis.

Leucovorin (also called folinic acid) acts as a biochemical cofactor for 1-carbon transfer reactions in the synthesis of purines and pyrimidines. Leucovorin does not require the enzyme dihydrofolate reductase (DHFR) for conversion to tetrahydrofolic acid. The effects of methotrexate and other DHFR-antagonists are inhibited by leucovorin. Leucovorin can potentiate the cytotoxic effects of fluorinated pyrimidines (i.e., fluorouracil and floxuridine). After 5-FU is activated within the cell, it is accompanied by a folate cofactor, and inhibits the enzyme thymidylate synthetase, thus inhibiting pyrimidine synthesis. Leucovorin increases the folate pool, thereby increasing the binding of folate cofactor and active 5-FU with thymidylate synthetase.

Leucovorin has dextro- and levo-isomers, only the latter one being pharmacologically useful. As such, the bioactive levo-isomer ("levoleucovorin") has also been approved by the FDA for treatment of cancer. The dosage of levoleucovorin is typically half that of the racemic mixture containing both dextro (d) and levo (l) isomers.

FU and leucovorin will be stored and handled according to the country specific package inserts.

IV. Administration

Liposomal irinotecan is administered intravenously, either alone or in combination with 5-fluorouracil (5-FU) and/or leucovorin. In one embodiment, liposomal irinotecan is administered prior to 5-FU and leucovorin. In another embodiment, leucovorin is administered prior to 5-FU. In another embodiment, liposomal irinotecan is administered intravenously over 90 minutes. In another embodiment, 5-FU is administered intravenously over 46 hours. In another embodiment, leucovorin is administered intravenously over 30 minutes. In various embodiments the liposomal irinotecan is MM-398.

V. Patient Populations

In one embodiment, a patient treated using the methods and compositions disclosed herein exhibits evidence of recurrent or persistent pancreatic cancer following primary chemotherapy.

In another embodiment, the patient has had and failed at least one prior platinum based chemotherapy regimen for management of primary or recurrent disease, e.g., a chemotherapy regimen comprising carboplatin, cisplatin, or another organoplatinum compound.

In an additional embodiment, the patient has failed prior treatment with gemcitabine or become resistant to gemcitabine.

In one embodiment a resistant or refractory tumor is one where the treatment-free interval following completion of a course of therapy for a patient having the tumor is less than 6 months (e.g., owing to recurrence of the cancer) or where there is tumor progression during the course of therapy.

In another embodiment, the pancreatic cancer of the patient undergoing treatment is advanced pancreatic cancer, which is a pancreatic tumor that exhibits either or both of distant metastasis or peripancreatic extension of the tumor.

The compositions and methods disclosed herein are useful for the treatment of all pancreatic cancers, including pancreatic cancers that are refractory or resistant to other anti-cancer treatments.

VI. Combination Therapy

In one embodiment, liposomal irinotecan is co-administered to patients having pancreatic cancer in combination with 5-fluorouracil (5-FU) and leucovorin, according to a particular clinical dosage regimen, such as those described herein. In one embodiment, the liposomal irinotecan is MM-398.

As used herein, adjunctive or combined administration (coadministration) includes simultaneous administration of the compounds in the same or different dosage form, or separate administration of the compounds (e.g., sequential administration). For example, liposomal irinotecan can be simultaneously administered with 5-FU and leucovorin. Alternatively, liposomal irinotecan can be administered in combination with 5-FU and leucovorin, wherein liposomal irinotecan, 5-FU and leucovorin are formulated for separate administration and are administered concurrently or sequentially. For example, liposomal irinotecan can be administered first followed by (e.g., immediately followed by) the administration of the 5-FU and leucovorin. Such concurrent or sequential administration preferably results in liposomal irinotecan, 5-FU, and leucovorin being simultaneously present in treated patients. In a particular embodiment, liposomal irinotecan is administered prior to 5-FU and leucovorin. In another particular embodiment, leucovorin is administered prior to 5-FU.

In another embodiment, liposomal irinotecan, 5-FU, and leucovorin are formulated for intravenous administration. In a particular embodiment, the patient is administered an effective amount each of liposomal irinotecan, 5-fluorouracil (5-FU), and leucovorin, wherein the treatment comprises at least one cycle, wherein the cycle is a period of 2 weeks, and wherein for each cycle: (a) liposomal irinotecan is administered on day 1 of the cycle at a dose of 80 mg/m$^2$, except if the patient is homozygous for the UGT1A1*28 allele, wherein liposomal irinotecan is administered on day 1 of cycle 1 at a dose of 60 mg/m$^2$; (b) 5-FU is administered at a dose of 2400 mg/m$^2$; and (c) leucovorin is administered at a dose of 200 mg/m$^2$ (l form) or 400 mg/m$^2$ (l+d racemic form) In a particular embodiment, the dose of liposomal irinotecan administered to the patient homozygous for the UGT1A1*28 allele is increased after one cycle to 80 mg/m$^2$.

In one embodiment, liposomal irinotecan may be initially administered at a high dose and may be lowered over time. In another embodiment, liposomal irinotecan is initially administered at a low dose and increased over time. In one embodiment, liposomal irinotecan is administered as a monotherapy.

In another embodiment, the dose of 5-FU is varied over time. For example, 5-FU may be initially administered at a high dose and may be lowered over time. In another embodiment, 5-FU is initially administered at a low dose and increased over time.

In another embodiment, the dose of leucovorin is varied over time. For example, leucovorin may be initially administered at a high dose and may be lowered over time. In another embodiment, leucovorin is initially administered at a low dose and increased over time.

VII. Treatment Protocols

Suitable treatment protocols include, for example, those wherein the patient is administered an effective amount of liposomal irinotecan, wherein the treatment comprises at least one cycle, wherein the cycle is a period of 3 weeks, and wherein for each cycle the liposomal irinotecan is administered on day 1 of the cycle at a dose of 120 mg/m$^2$, except if the patient is homozygous for the UGT1A1*28 allele, wherein liposomal irinotecan is administered on day 1 of cycle 1 at a dose of 80 mg/m$^2$. In one embodiment, the dose of liposomal irinotecan administered to the patient homozygous for the UGT1A1*28 allele is increased after one cycle in increments of 20 mg/m$^2$, up to a maximum of 120 mg/m$^2$.

In another embodiment, the treatment protocol includes administering to the patient an effective amount each of liposomal irinotecan, 5-fluorouracil (5-FU), and leucovorin, wherein the treatment comprises at least one cycle, wherein the cycle is a period of 2 weeks, and wherein for each cycle: (a) liposomal irinotecan is administered on day 1 of the cycle at a dose of 80 mg/m$^2$, except if the patient is homozygous for the UGT1A1*28 allele, wherein liposomal irinotecan is administered on day 1 of cycle 1 at a dose of 60 mg/m$^2$; (b) 5-FU is administered at a dose of 2400 mg/m$^2$; and (c) leucovorin is administered at a dose of 200 mg/m$^2$ (l form) or 400 mg/m$^2$ (l+d racemic form). In a particular embodiment, the dose of liposomal irinotecan administered to the patient homozygous for the UGT1A1*28 allele is increased after one cycle to 80 mg/m$^2$.

VIII. Outcomes

Provided herein are methods for treating pancreatic cancer in a patient comprising administering to the patient liposomal irinotecan (MM-398), alone or in combination with 5-fluorouracil (5-FU) and leucovorin, according to a particular clinical dosage regimen. Preferably, the combination therapy with liposomal irinotecan with 5-FU and leucovorin exhibits therapeutic synergy.

"Therapeutic synergy" refers to a phenomenon where treatment of patients with a combination of therapeutic agents manifests a therapeutically superior outcome to the outcome achieved by each individual constituent of the combination used at its optimum dose (T. H. Corbett et al., 1982, Cancer Treatment Reports, 66, 1187). In this context a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components. In xenograft models, a combination, used at its maximum tolerated dose, in which each of the constituents will be present at a dose generally not exceeding its individual maximum tolerated dose, manifests therapeutic synergy when decrease in tumor growth achieved by administration of the combination is greater than the value of the decrease in tumor growth of the best constituent when the constituent is administered alone.

Thus, in combination, the components of such combinations have an additive or superadditive effect on suppressing pancreatic tumor growth, as compared to monotherapy with liposome-encapsulated irinotecan alone or treatment with the chemotherapeutic(s) in the absence of liposomal irinotecan therapy. By "additive" is meant a result that is greater in extent (e.g., in the degree of reduction of tumor mitotic index or of tumor growth or in the degree of tumor shrinkage or the frequency and/or duration of symptom-free or symptom-reduced periods) than the best separate result achieved by monotherapy with each individual component, while "superadditive" is used to indicate a result that exceeds in extent the sum of such separate results. In one embodiment, the additive effect is measured as slowing or stopping of pancreatic tumor growth. The additive effect can also be measured as, e.g., reduction in size of a pancreatic tumor, reduction of tumor mitotic index, reduction in number of metastatic lesions over time, increase in overall response rate, or increase in median or overall survival.

One non-limiting example of a measure by which effectiveness of a therapeutic treatment can be quantified is by calculating the log 10 cell kill, which is determined according to the following equation:

$$\log 10 \text{ cell kill} = T\,C(\text{days})/3.32 \times Td$$

in which T C represents the delay in growth of the cells, which is the average time, in days, for the tumors of the treated group (T) and the tumors of the control group (C) to have reached a predetermined value (1 g, or 10 mL, for example), and Td represents the time, in days necessary for the volume of the tumor to double in the control animals. When applying this measure, a product is considered to be active if log 10 cell kill is greater than or equal to 0.7 and a product is considered to be very active if log 10 cell kill is greater than 2.8. Using this measure, a combination, used at its own maximum tolerated dose, in which each of the constituents is present at a dose generally less than or equal to its maximum tolerated dose, exhibits therapeutic synergy when the log 10 cell kill is greater than the value of the log 10 cell kill of the best constituent when it is administered alone. In an exemplary case, the log 10 cell kill of the combination exceeds the value of the log 10 cell kill of the best constituent of the combination by at least 0.1 log cell kill, at least 0.5 log cell kill, or at least 1.0 log cell kill.

Responses to therapy may include:

Pathologic complete response (pCR): absence of invasive cancer in the breast and lymph nodes following primary systemic treatment.

Complete Response (CR): Disappearance of all target lesions. Any pathological lymph nodes (whether target or non-target) which has reduction in short axis to <10 mm;

Partial Response (PR): At least a 30% decrease in the sum of dimensions of target lesions, taking as reference the baseline sum diameters;

Stable Disease (SD): Neither sufficient shrinkage to qualify for partial response, nor sufficient increase to qualify for progressive disease, taking as reference the smallest sum diameters while on study; or Meanwhile, non-CR/Non-PD denotes a persistence of one or more non-target lesion(s) and/or maintenance of tumor marker level above the normal limits.

Progressive Disease (PD) denotes at least a 20% increase in the sum of dimensions of target lesions, taking as reference the smallest sum on study (this includes the baseline sum if that is the smallest on study). In addition to the relative increase of 20%, the sum must also demonstrate an absolute increase of 5 mm. The appearance of one or more new lesions is also considered progression.

In exemplary outcomes, patients treated according to the methods disclosed herein may experience improvement in at least one sign of pancreatic cancer.

In one embodiment the patient so treated exhibits pCR, CR, PR, or SD.

In another embodiment, the patient so treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, such improvement is measured by a reduction in the quantity and/or size of measurable tumor lesions. Measurable lesions are defined as those that can be accurately measured in at least one dimension (longest diameter is to be recorded) as ≥10 mm by CT scan (CT scan slice thickness no greater than 5 mm), 10 mm caliper measurement by clinical exam or >20 mm by chest X-ray. The size of non-target lesions, e.g., pathological lymph nodes can also be measured for improvement. In one embodiment, lesions can be measured on chest x-rays or CT or MRI films.

In other embodiments, cytology or histology can be used to evaluate responsiveness to a therapy. The cytological confirmation of the neoplastic origin of any effusion that appears or worsens during treatment when the measurable tumor has met criteria for response or stable disease can be considered to differentiate between response or stable disease (an effusion may be a side effect of the treatment) and progressive disease.

In some embodiments, administration of effective amounts of liposomal irinotecan, 5-FU and leucovorin according to any of the methods provided herein produce at least one therapeutic effect selected from the group consisting of reduction in size of a breast tumor, reduction in number of metastatic lesions appearing over time, complete remission, partial remission, stable disease, increase in overall response rate, or a pathologic complete response. In some embodiments, the provided methods of treatment produce a comparable clinical benefit rate (CBR=CR+PR+SD≥6 months) better than that achieved by the same combinations of anti-cancer agents administered without concomitant MM-398 administration. In other embodiments, the improvement of clinical benefit rate is about 20% 20%, 30%, 40%, 50%, 60%, 70%, 80% or more compared to the same combinations of anti-cancer agents administered without concomitant MM-398 administration.

The following examples are illustrative and should not be construed as limiting the scope of this disclosure in any way; many variations and equivalents will become apparent to those skilled in the art upon reading the present disclosure.

EXAMPLES

Example 1: Activity of MM-398 in an Orthotopic Pancreas Tumor Model Expressing Luciferase (L3.6pl)

The anti-tumor activity of MM-398 was assessed in an orthotopic pancreatic cancer model (L3.6pl), a highly hypoxic preclinical tumor model. Approximately $2.5 \times 10^{-5}$ L3.6pl pancreatic tumor cells were implanted by direct injection into the pancreas. The bioluminescence images (BLI) were followed over time for tumor burden detection/quantitation. MM-398 and free irinotecan were dosed at a dose of 20 mg/kg/dose weekly for three weeks. As shown in FIG. 1, MM-398 (liposomal CPT11) had significant anti-tumor activity, as compared to a control (HBS) and free CPT11.

Example 2: Accumulation of SN-38 in Tumors Following Treatment with Free Irinotecan or Liposomal Irinotecan (MM-398)

It was hypothesized that the anti-tumor activity observed in the orthotopic pancreatic cancer model is due to the effect of macrophages in converting irinotecan to the more active SN-38 locally. To test this hypothesis, human colon cancer cells (HT-29) were injected subcutaneously into SCID mice, 40 mg/kg of free irinotecan or MM-398 was injected intravenously when the tumors reached 1000 mm³ in size. Tumor-bearing mice were sacrificed at different time points, tumors from both groups were extracted and the concentrations of SN-38 were measured.

Figure 2:
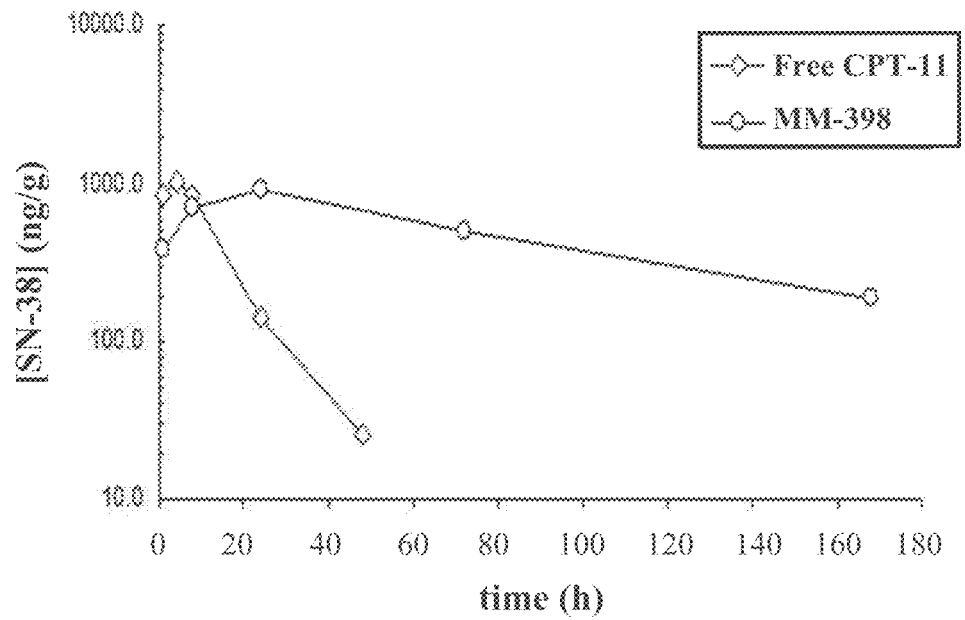
FIG. 2 is a graph showing accumulation of SN-38 in tumors following treatment with free irinotecan or liposomal irinotecan (MM-398).

As shown in FIG. 2, there was a 20-fold increase in the tumor AUCsN-38 for MM-398 as compared to free irinotecan. The long duration of exposure allows for prolonged exposure of the slow proliferating cancer cells to the active metabolite as they progress through the cell cycle. In addition, this activity was also hypothesized to result from a reduction in intra-tumoral hypoxia, and the subsequent downstream effects on angiogenesis, metastasis, and the immunosuppressive environment in tumors.

Example 3: Effect of MM-398 on Carbonic Anhydrase IX Staining in a HT29 Xenograft Model To test whether MM-398 reduces markers of hypoxia, experiments were conducted in a human colon cancer cell (HT-29) model. Specifically, HT-29 cells were injected subcutaneously into nude mice, on day 13 either PBS control or 1.25, 2.5, 5, 10 or 20 mg/kg MM-398 was injected intravenously. MM-398 was dosed once a week for 4 weeks at the indicated doses. Tumors from both groups (n=5) were extracted 24 hours after the last dose. Frozen tumor sections were used for immunohistochemical staining of Carbonic Anhydrase IX (CAIX). Quantification of CAIX staining was performed using Definiens® (Definiens AG, Munich) software.

Figure 3:
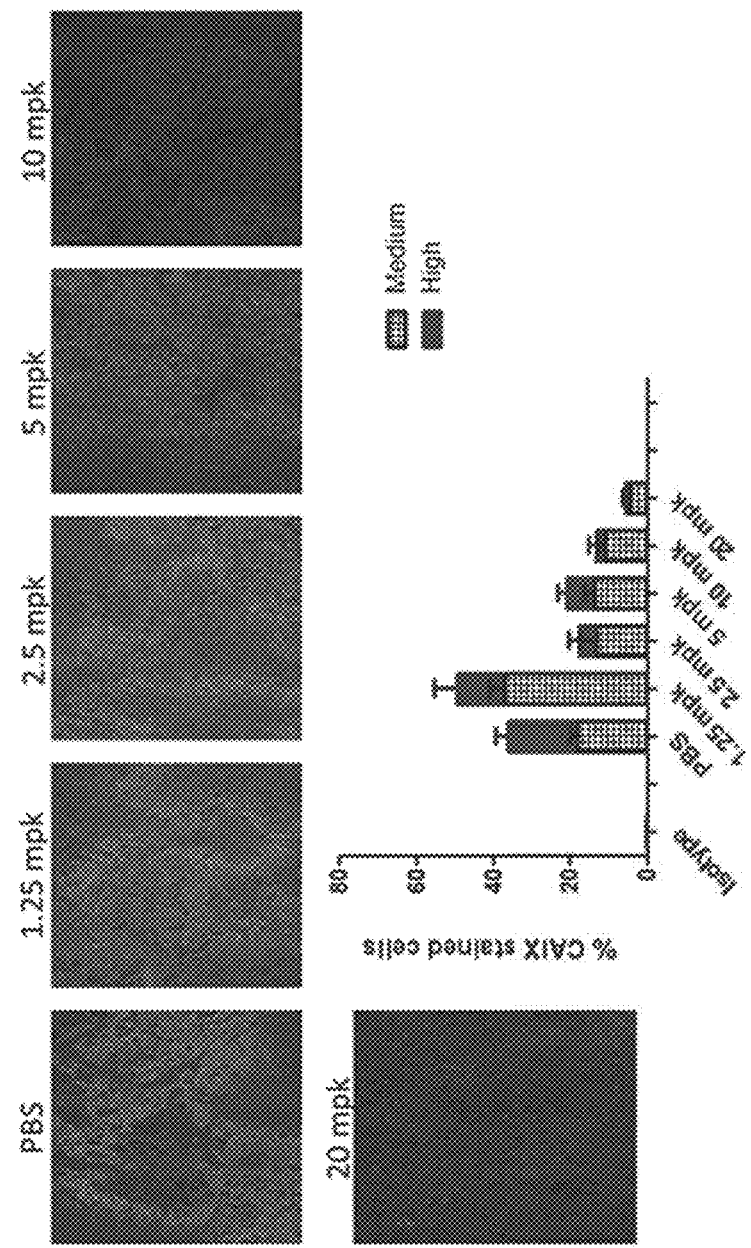
FIG. 3 is a graph showing the effect of MM-398 on Carbonic Anhydrase IX Staining in a HT29 Xenograft Model.

As shown in FIG. 3, MM-398 reduced markers of hypoxia. Specifically, the graphs in FIG. 3 show the percentage of cells that stained with medium (middle third) or high (top third) intensity for CAIX. Representative samples from each group are shown as well as the group average (mean+/−stdev). MM-398 treatment modifies the tumor microenvironment by decreasing the percentage of both medium and high CAIX positive cells in a dose-dependent manner. As hypoxia is a hallmark of resistant and aggressive disease, a reduction in hypoxia is expected to make tumor cells more sensitive to chemotherapies.

Example 4: MM-398 Increases Perfusion of Hoechst Stain

Figure 4:
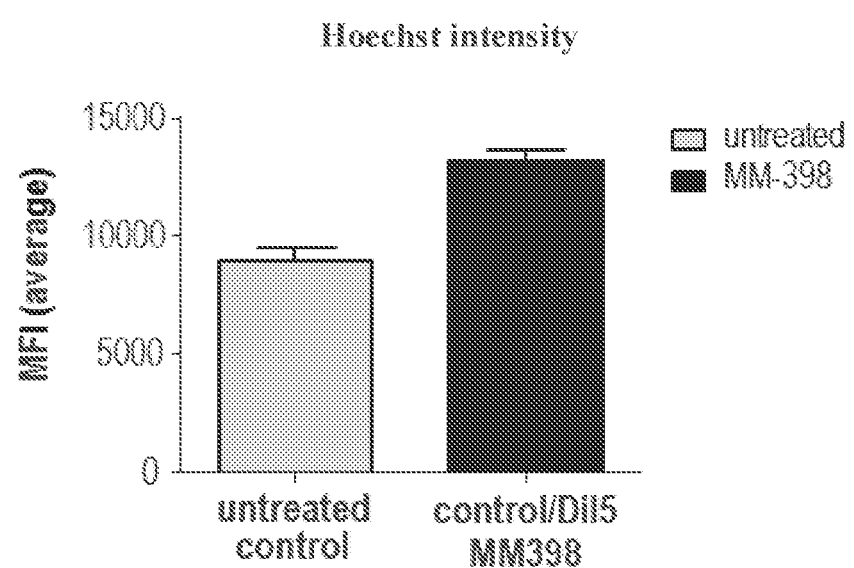
FIG. 4 shows the effect of MM-398 on perfusion of small molecule Hoechst stain.

In addition to changing the chemosensitivity of tumor cells through modification of the tumor microenvironment, lowering hypoxia can indicate improved tumor vascularization, which can facilitate delivery of small molecule therapies. MM-398 treatment led to increased microvessel density 6 days after treatment as measured by CD31 (platelet endothelial cell adhesion molecule) staining in an HT29 xenograft study. To further assess the effect of MM-398 on small molecule tumor vascularization, a Hoechst 33342 perfusion experiment was conducted. Specifically, a primary pancreatic tumor was grown in NOD-SCID mice and given one dose of MM-398 (20 mg/kg). After 24 hours, Hoechst 33342 stain was administered 20 minutes prior to sacrificing the animal. As shown in FIG. 4, the increase in stain intensity in treated mice was statistically significant, p<0.001. These data indicate that MM-398 modifies the tumor microenvironment in a manner that should make tumors more susceptible to agents such as 5-FU/LV, through decreasing tumor hypoxia and increasing small molecule perfusion.

Example 5: MM-398 Pharmacokinetics in Humans (Phase I)

The pharmacokinetic profile of MM-398 single agent was investigated in a phase I clinical study (PEP0201) in patients at 60, 120 or 180 mg/m² dose levels and in a phase II clinical trial in gastric cancer patients (PEP0206) at 120 mg/m². Plasma levels of total irinotecan, SN-38 and encapsulated irinotecan were measured in these studies.

The peak serum concentrations of total irinotecan ($C_{max}$) ranged from 48-79 μg/ml for 120 mg/m² of MM-398, which was approximately 50 fold higher than 125 mg/m² free irinotecan. The total irinotecan half-life ($t_{1/2}$) for MM-398 ranged from 21 to 48 hours, which was approximately 2-3 fold higher than 125 mg/m² of free irinotecan. Overall, total irinotecan exposure at one week (AUC 0-T) ranged from 1200-3000 (g*h/ml) at a dose of 120 mg/m² of MM-398, approximately 50-100 fold higher than 300 mg/m² of free irinotecan. In contrast, SN38 $C_{max}$ levels at 120 mg/m² of MM-398 ranged from 9 to 17 ng/ml, which was approximately 50% less than free irinotecan at 125 mg/m². Overall, exposure of SN38 at one week (AUC 0-T) ranged from 474 to 997 ng*/ml and was only 1-2 fold higher than achieved by free irinotecan at 300 mg/m². For both SN38 and total irinotecan, AUC increased less than proportionally with dose of MM-398. The PK parameters of encapsulated irinotecan almost matched that of total irinotecan indicates that most of irinotecan remained encapsulated in the liposomes during circulation. The MM-398 PK parameters were not significantly changed when combined with 5-FU/LV. FIGS. 5 and 6 summarize the PK findings in previous studies of MM 398.

Example 6: Phase 1 Dose Escalation Study

A regimen combining fluorouracil, leucovorin, and MM-398 was studied in a phase 1 trial of solid tumors in 16 subjects, of whom 5 were patients with pancreatic cancer. The objective tumor response rate, duration of response, and disease control rate were efficacy endpoints of the study. Among the 15 efficacy-evaluable patients, 2 (13.3%) had confirmed PR, 9 (60.0%) had SD, and 4 (26.7%) had PD. The overall disease control rate was 73.3%. Partial response was observed in one gastric cancer patient (at 80 mg/m² dose level) and one breast cancer patient (at 100 mg/m2 dose level), with the duration of response of 142 and 76 days, respectively. Among the 6 patients who received the MTD dose of 80 mg/m², there were 1 PR, 4 SD and 1 PD. The tumor response rate and disease control rate were 16.7% and 83.3%, respectively. The main DLTs were grade 3 diarrhea, leucopenia, neutropenia and febrile neutropenia. The MTD for MM-398 was 80 mg/m².

In the phase 1 dose-escalation study of MM-398 in combination with 5-FU/LV in advanced solid tumors (PEP0203), a total of 401 episodes of AE were reported from the 16 treated subjects (safety population), of which 74 (18.4%) were of CTC grade 3 or above. Among all AEs, 231 (57.6%) were considered by the investigators to be treatment-related. The most common treatment-related AEs, included nausea (81.3%), diarrhea (75.0%), vomiting (68.8%), fatigue (43.8%), mucositis (43.8%), leucopenia (37.5%), neutropenia (37.5%), weight loss (37.5%), anemia (31.3%), and alopecia (31.3%). Acute cholinergic diarrhea was rarely observed. Table 1 provides the incidence of treatment-emergent adverse events by maximum CTC grade and by causality (incidence ≥20%), as seen in the PEP0203 study. Table 2 provides the incidence of grade 3 or higher treatment-emergent adverse events seen in the 5 pancreatic cancer patients treated in the PEP0203 study.

TABLE 1

Incidence of treatment-emergent adverse events by maximum CTC grade and by causality (incidence ≥20%) in the PEP0203 Study

| System organ class Preferred Term | Total (N = 16) | Severity (Grade)[1] | | | | Causality[2] | |
|---|---|---|---|---|---|---|---|
| | | I | II | III | IV | Yes | No |
| Blood and lymphatic system disorders | | | | | | | |
| Anemia | 7 (43.8%) | 3 | 2 | 2 | 0 | 5 | 2 |
| Leucopenia | 6 (37.5%) | 0 | 3 | 2 | 1 | 6 | 0 |
| Neutropenia | 6 (37.5%) | 0 | 2 | 3 | 1 | 6 | 0 |
| Gastrointestinal disorders | | | | | | | |
| Abdominal pain | 7 (43.8%) | 3 | 2 | 2 | 0 | 3 | 4 |
| Constipation | 6 (37.5%) | 3 | 3 | 0 | 0 | 0 | 6 |
| Diarrhea | 12 (75.0%) | 3 | 4 | 5 | 0 | 12 | 0 |
| Nausea | 13 (81.3%) | 6 | 6 | 1 | 0 | 13 | 0 |
| Vomiting | 12 (75.0%) | 3 | 8 | 1 | 0 | 11 | 1 |
| General disorders and administration site conditions | | | | | | | |
| Fatigue | 8 (50.0%) | 4 | 3 | 1 | 0 | 7 | 1 |
| Mucosal inflammation | 7 (43.8%) | 4 | 3 | 0 | 0 | 7 | 0 |
| Pyrexia | 7 (43.8%) | 3 | 4 | 0 | 0 | 2 | 5 |
| Infections and infestations | | | | | | | |
| Infection | 6 (37.5%) | 0 | 3 | 3 | 0 | 2 | 4 |
| Investigations | | | | | | | |
| ALT increased | 5 (31.3%) | 3 | 2 | 0 | 0 | 4 | 1 |
| AST increased | 4 (25.0%) | 3 | 1 | 0 | 0 | 1 | 3 |
| Weight decreased | 8 (50.0%) | 4 | 4 | 0 | 0 | 6 | 2 |
| Metabolism and nutrition disorders | | | | | | | |
| Anorexia | 4 (25.0%) | 1 | 2 | 1 | 0 | 3 | 1 |
| Hypoalbuminaemia | 4 (25.0%) | 0 | 3 | 1 | 0 | 0 | 4 |
| Hypocalcaemia | 5 (31.3%) | 1 | 4 | 0 | 0 | 0 | 5 |
| Hypokalaemia | 8 (50.0%) | 2 | 0 | 5 | 1 | 2 | 6 |
| Hyponatraemia | 4 (25.0%) | 2 | 0 | 0 | 2 | 0 | 4 |
| Nervous system disorders | | | | | | | |
| Dizziness | 4 (25.0%) | 4 | 0 | 0 | 0 | 1 | 3 |
| Psychiatric disorders | | | | | | | |
| Insomnia | 4 (25.0%) | 4 | 0 | 0 | 0 | 1 | 3 |
| Respiratory, thoracic and mediastinal disorders | | | | | | | |
| Cough | 5 (31.3%) | 3 | 1 | 1 | 0 | 0 | 5 |
| Skin and subcutaneous tissue disorders | | | | | | | |
| Alopecia | 5 (31.3%) | 5 | 0 | 0 | 0 | 5 | 0 |

[1]Severity grading used the highest grading ever rated for each subject if the subject had such adverse event reported
[2]Defined as subject ever experienced AE related to the study drug in causality or not

TABLE 2

Incidence of Grade 3 or higher treatment-emergent adverse events in pancreatic cancer patients in the PEP0203 Study

| Primary system organ class Preferred term | Overall N = 5 n (%) | 60 mg/m2 N = 1 n (%) | 80 mg/m2 N = 3 n (%) | 120 mg/m2 N = 1 n (%) |
|---|---|---|---|---|
| Any primary system organ class | | | | |
| Total | 3 (60.0) | 0 | 2 (66.7) | 1 (100.0) |
| Infections and infestations | | | | |
| Total | 3 (60.0) | 0 | 2 (66.7) | 1 (100.0) |
| Hepatitis viral | 1 (20.0) | 0 | 1 (33.3) | 0 |
| Infection | 1 (20.0) | 0 | 0 | 1 (100.0) |
| Pneumonia | 1 (20.0) | 0 | 1 (33.3) | 0 |
| Septic shock | 1 (20.0) | 0 | 1 (33.3) | 0 |
| Blood and lymphatic system disorders | | | | |
| Total | 2 (40.0) | 0 | 1 (33.3) | 1 (100.0) |
| Lymphopenia | 1 (20.0) | 0 | 0 | 1 (100.0) |

TABLE 2-continued

Incidence of Grade 3 or higher treatment-emergent adverse events in pancreatic cancer patients in the PEP0203 Study

| Primary system organ class Preferred term | Overall N = 5 n (%) | 60 mg/m2 N = 1 n (%) | 80 mg/m2 N = 3 n (%) | 120 mg/m2 N = 1 n (%) |
|---|---|---|---|---|
| Neutropenia | 1 (20.0) | 0 | 1 (33.3) | 0 |
| White blood cell disorder | 1 (20.0) | 0 | 0 | 1 (100.0) |
| Gastrointestinal disorders | | | | |
| Total | 2 (40.0) | 0 | 1 (33.3) | 1 (100.0) |
| Diarrhoea | 2 (40.0) | 0 | 1 (33.3) | 1 (100.0) |
| Abdominal pain | 1 (20.0) | 0 | 0 | 1 (100.0) |
| Gastrointestinal haemorrhage | 1 (20.0) | 0 | 1 (33.3) | 0 |
| Investigations | | | | |
| Total | 2 (40.0) | 0 | 1 (33.3) | 1 (100.0) |
| Blood bilirubin increased | 1 (20.0) | 0 | 1 (33.3) | 0 |
| Lipase increased | 1 (20.0) | 0 | 0 | 1 (100.0) |
| Neutrophil count decreased | 1 (20.0) | 0 | 0 | 1 (100.0) |
| White blood cell count decreased | 1 (20.0) | 0 | 0 | 1 (100.0) |
| Metabolism and nutrition disorders | | | | |
| Total | 2 (40.0) | 0 | 1 (33.3) | 1 (100.0) |
| Hypoalbuminaemia | 1 (20.0) | 0 | 1 (33.3) | 0 |
| Hypokalaemia | 1 (20.0) | 0 | 1 (33.3) | 0 |
| Hyponatraemia | 1 (20.0) | 0 | 0 | 1 (100.0) |
| Hypophosphataemia | 1 (20.0) | 0 | 0 | 1 (100.0) |
| Respiratory, thoracic and mediastinal disorders | | | | |
| Total | 2 (40.0) | 0 | 1 (33.3) | 1 (100.0) |
| Dyspnoea | 1 (20.0) | 0 | 0 | 1 (100.0) |
| Pleural effusion | 1 (20.0) | 0 | 1 (33.3) | 0 |
| General disorders and administration site conditions | | | | |
| Total | 1 (20.0) | 0 | 0 | 1 (100.0) |
| Death | 1 (20.0) | 0 | 0 | 1 (100.0) |

Example 7: Phase 3 Trial

The promising efficacy and safety data from the Phase 1 Trial (described above) warrant the MM-398 and 5-FU plus leucovorin combination to be explored further in a phase 3 study.

Objectives

The primary objective of the Phase 3 trial is to compare overall survival following treatment with MM-398, with or without 5-fluorouracil plus leucovorin, versus 5-fluorouracil and leucovorin in patients with metastatic pancreatic cancer that have progressed on gemcitabine based therapy. The secondary objectives include the following:

To compare time-to-event efficacy endpoints between the experimental and control arms (i.e., Progression-free survival (PFS) and Time to treatment failure (TTF));

To compare the Objective Response Rate (ORR) between the treatment arms;

To compare the tumor marker response of CA 19-9 between the treatment arms;

To compare the Clinical Benefit Response (CBR) rate between the treatment arms;

To assess patient-reported outcomes (PROs) between the treatment arms using the European Organization for Research and Treatment of Cancer (EORTC) quality-of-life core questionnaire (EORTC-QLQ-C30);

To compare the safety and adverse event profile between the treatment arms; and

To determine the pharmacokinetic properties of MM-398, as a single agent and in combination with 5-FU and leucovorin.

A key exploratory objective of this study is to explore biomarkers associated with toxicity and efficacy following treatment with MM-398 and MM-398 plus 5-FU and leucovorin.

A. Study Design

This is an open label, randomized, three arm, Phase 3 trial of MM-398, with or without 5-FU and leucovorin, versus 5-fluorouracil (5-FU) and leucovorin (also known as folinic acid), in metastatic pancreatic cancer patients who have progressed on prior gemcitabine based therapy.

Approximately 405 eligible patients will be enrolled in this global study, under the protocol version 2 or later. All patients will participate in up to 28 days of screening, during which they will be assessed for eligibility and screened for the UGT1A1*28 allele. Eligible patients will be randomized, in a 1:1:1 ratio, to one of the following treatment arms:

| | |
|---|---|
| Arm A (experimental arm): MM-398 | MM 398 120 mg/m2 IV over 90 minutes, every 3 weeks. Patients who are homozygous for UGT1A1*28 allele will receive the first cycle of therapy at a reduced dose of 80 mg/m$^2$. If the patient does not experience any drug related toxicity after the first administration of MM-398, from cycle 2 onwards, the dose may be increased in increments of 20 mg/m$^2$ up to a maximum of 120 mg/m$^2$. |
| Arm B (control arm): 5-FU and leucovorin | 5-FU 2000 mg/m$^2$ IV over 24-hours (+/−30 minutes), administered weekly for 4 weeks (days 1, 8, 15 and 22), followed by 2 weeks of rest, in a 6 weekly cycle. Levoleucovorin dosed at 200 mg/m$^2$ or the leucovorin l + d racemic mixture dosed at 400 mg/m$^2$, given IV over 30 minutes, administered weekly for 4 weeks (days 1, 8, 15 and 22), followed by 2 weeks of rest, in a 6 weekly cycle. |
| Arm C (experimental arm): MM-398, 5-FU and leucovorin | MM-398 80 mg/m$^2$ IV over 90 minutes, every 2 weeks. Patients who are homozygous for UGT1A1*28 allele and are randomized to Arm C, will receive the first cycle of therapy at a reduced dose of 60 mg/m$^2$. If the patient does not experience any drug related toxicity after the first administration of MM-398, from cycle 2 onwards, the dose may be increased to 80 mg/m$^2$. |

5-FU 2400 mg/m² IV over 46-hours, every 2 weeks.
Levoleucovorin dosed at 200 mg/m² or the l + d racemic mixture dosed at 400 mg/m², IV over 30 minutes, every 2 weeks.
MM-398 should be administered prior to 5-FU and leucovorin; leucovorin should always be administered prior to 5-FU. If the dosing of either MM-398 or 5-FU/leucovorin needs to be withheld, then the other drug in the combination should not be administered either.

Patients will be evenly randomized to the treatment arms using an Interactive Web Response System (IWRS) at a central location. The randomization will be stratified based on the following prognostic factors:

Baseline albumin levels (≥4.0 g/dL vs<4.0 g/dL)
KPS (70 and 80 vs≥90)
Ethnicity (Caucasian vs East Asian vs All Others)

Therapy will be administered in cycles. Patients will be treated until disease progression (radiologic or clinical deterioration), intolerable toxicity or other reasons for study termination. Tumor responses will be assessed, using the RECIST guidelines (Eisenhauer, E. A., et al., "New response evaluation criteria in solid tumors: Revised RECIST guideline (version 1.1). *European Journal of Cancer*, 2009. 45:pp. 228-247) every 6 weeks or sooner if disease progression based on clinical signs and symptoms is evident. Tumor measurement images will be collected and stored on all patients throughout the study. However, all treatment decisions will be based on the local radiologist and/or PI assessment of disease status. An independent review of the scans may be performed in the event that an independent analysis of ORR and/or PFS is necessary.

Following treatment discontinuation a 30-day post therapy follow up visit is required. Subsequently, all patients will be followed-up every 1 month for overall survival (by phone or visit to the study site) until death or study closure, whichever occurs first. Patients, who withdraw from study treatment due to reasons other than objective disease progression, should continue to be assessed every 6 weeks during the follow-up period for radiologic progression (including patients who discontinue due to symptomatic deterioration).

All patients will be asked to complete a pain assessment and analgesic consumption diary throughout their participation in the study, which will document the patient's assessment of their pain intensity and daily analgesic consumption. Patient responses will be used for assessment of the clinical benefit response along with the other parameters. All patients will also be required to complete the EORTC-QLQ-C30 questionnaire for assessing quality of life.

In order to address the exploratory objectives of this study, all sites will be required to participate in the companion translational research (TR) protocol (MM-398-07-03-01.TR), unless prohibited by local regulations. Participation is this study will be optional for patients and they will be required to provide a separate consent for the translational research.

The primary analysis of OS will take place once at least 305 deaths events have occurred in patients enrolled under protocol version 2 or later. Patients receiving study treatment at the time of primary analysis for OS will continue to receive treatment until one of the criteria for discontinuation is met. During the course of the study, regular review of safety data will be conducted by an independent data safety monitoring board (DSMB). FIG. 7 illustrates the study design.

B. Patient Selection and Discontinuation

Approximately 405 patients will be enrolled globally in this study, under the protocol version 2 or later. In order to be included in the study, patients must have/be:

1. Histologically or cytologically confirmed adenocarcinoma of exocrine pancreas
2. Documented metastatic disease; disease status may be measurable or non-measurable as defined by RECIST v1.1 guidelines
3. Documented disease progression after prior gemcitabine or gemcitabine containing therapy, in locally advanced or metastatic setting. Examples of permitted therapies include, but are not limited to:
   Single agent gemcitabine
   Any one gemcitabine-based regimen, with or without maintenance gemcitabine
   Single agent gemcitabine to which a platinum agent, a fluoropyrimidine, or erlotinib was subsequently added
   Gemcitabine administered in the adjuvant setting if disease recurrence occurred within 6 months of completing the adjuvant therapy
4. Karnofsky Performance Status (KPS)≥70
5. Adequate bone marrow reserves as evidenced by:
   ANC>1,500 cells/µl without the use of hematopoietic growth factors; and
   Platelet count >100,000 cells/µl; and
   Hemoglobin >9 g/dL (blood transfusions are permitted for patients with hemoglobin levels below 9 g/dL)
6. Adequate hepatic function as evidenced by:
   Serum total bilirubin within normal range for the institution (biliary drainage is allowed for biliary obstruction)
   Albumin levels ≥3.0 g/dL
   Aspartate aminotransferase (AST) and alanine aminotransferase (ALT)≤2.5×ULN (≤5×ULN is acceptable if liver metastases are present)
7. Adequate renal function as evidenced by a serum creatinine ≤1.5×ULN
8. Normal ECG or ECG without any clinically significant findings
9. Recovered from the effects of any prior surgery, radiotherapy or other anti-neoplastic therapy
10. At least 18 years of age
11. Able to understand and sign an informed consent (or have a legal representative who is able to do so)

Patients must meet all the inclusion criteria listed above and none of the following exclusion criteria:

1. Active CNS metastases (indicated by clinical symptoms, cerebral edema, steroid requirement, or progressive disease)

2. Clinically significant gastrointestinal disorder including hepatic disorders, bleeding, inflammation, occlusion, or diarrhea > grade 1
3. History of any second malignancy in the last 5 years; subjects with prior history of in-situ cancer or basal or squamous cell skin cancer are eligible. Subjects with other malignancies are eligible if they have been continuously disease free for at least 5 years.
4. Severe arterial thromboembolic events (myocardial infarction, unstable angina pectoris, stroke) less than 6 months before inclusion
5. NYHA Class III or IV congestive heart failure, ventricular arrhythmias or uncontrolled blood pressure
6. Active infection or an unexplained fever >38.5° C. during screening visits or on the first scheduled day of dosing (at the discretion of the investigator, patients with tumor fever may be enrolled), which in the investigator's opinion might compromise the patient's participation in the trial or affect the study outcome
7. Known hypersensitivity to any of the components of MM-398, other liposomal products, fluropyrimidines or leucovorin
8. Investigational therapy administered within 4 weeks, or within a time interval less than at least 5 half-lives of the investigational agent, whichever is longer, prior to the first scheduled day of dosing in this study
9. Any other medical or social condition deemed by the Investigator to be likely to interfere with a patient's ability to sign informed consent, cooperate and participate in the study, or interfere with the interpretation of the results
10. Pregnant or breast feeding; females of child-bearing potential must test negative for pregnancy at the time of enrollment based on a urine or serum pregnancy test. Both male and female patients of reproductive potential must agree to use a reliable method of birth control, during the study and for 3 months following the last dose of study drug.

The criteria for enrollment must be followed explicitly. Patients will be discontinued from the study treatment in the following circumstances:

Patient has evidence of disease progression based on RECIST v1.1 criteria

Patient shows symptomatic deterioration

Patient experiences intolerable toxicity, or an adverse event which requires:
   A third dose reduction
   Treatment to be withheld for more than 21 days from the start of next cycle, unless, in the opinion of the investigator, the patient is receiving benefit from study treatment Patient is significantly non-compliant with study procedures per PI assessment The patient or patient's attending physician requests that the patient be withdrawn from the study treatment The investigator or Sponsor, for any reason, but considering the rights, safety and well-being of the patient(s) and in accordance with ICH/GCP Guidelines and local regulations, stops the study or stops the patient's participation in the study If a patient is lost to follow-up or withdraws from study treatment, attempts should be made to contact the patient to determine the reason for discontinuation. For patients who are lost to follow-up, at least 3 documented attempts, including one via certified mail, should be made to contact the patient before considering the patient lost to follow-up. If a patient discontinues study treatment due to reasons other than objective disease progression, the patient should continue to have radiological disease assessment every 6 weeks until objective disease progression is observed.

All patients who discontinue study treatment should continue to be followed-up as required by the protocol. The only circumstance under which a patient should not be followed for study endpoints is when the patient has withdrawn consent. Withdrawal of consent should be a patient initiated decision and should mean, not only that the patient wishes to discontinue study treatment and follow-up visits but also that the investigator is no longer authorized to make further efforts to contact the patient, including any efforts to identify their survival status.

C. Method of Assigning Patients to Treatment Groups

After all screening assessments have been completed and UGT1A1*28 results are available, patients will be randomized using a computerized interactive web response system (IWRS), in a 1:1:1 ratio, to one of the following treatment arms:

Arm A (experimental arm): MM-398
Arm B (control arm): 5-FU and leucovorin
Arm C (experimental arm): MM-398, 5-FU and leucovorin Randomization must occur within 7 days of planned dosing. The randomization will be stratified based on the following prognostic factors:

Baseline albumin levels (≥4.0 g/dL vs<4.0 g/dL)
KPS (70 and 80 vs≥90)
Ethnicity (Caucasian vs East Asian vs All Others)

Description of MM-398

MM-398 is irinotecan (also known as CPT-11) encapsulated in a liposomal drug delivery system. It will be supplied as sterile, single-use vials containing 9.5 mL of MM-398 at a concentration of 5 mg/mL. The vials contain a 0.5 mL excess to facilitate the withdrawal of the label amount from each 10 mL vial.

MM-398 must be stored refrigerated at 2 to 8° C., with protection from light. Light protection is not required during infusion. MM-398 must not be frozen. Responsible individuals should inspect vial contents for particulate matter before and after they withdraw the drug product from a vial into a syringe.

MM-398 must be diluted prior to administration. The diluted solution is physically and chemically stable for 6 hours at room temperature (15-30° C.), but it is preferred to be stored at refrigerated temperatures (2-8° C.), and protected from light. The diluted solution must not be frozen. Because of possible microbial contamination during dilution, it is advisable to use the diluted solution within 24 hours if refrigerated (2-8° C.), and within 6 hours if kept at room temperature (15-30° C.).

Twenty vials of MM-398 will be packaged in a cardboard container. The individual vials, as well as the outside of the cardboard container, will be labeled in accordance with local regulatory requirements.

MM-398 will be dosed and administered as follows. All patients will be screened for UGT1A1*28 allele at baseline.

---

Arm A  Patients who do not have the homozygous allele for UGT1A1*28 will receive MM-398 at a dose of 120 mg/m². Any patient who is homozygous for UGT1A1*28 will receive the first cycle of therapy at a reduced dose of 80 mg/m². If the patient does not experience any drug related toxicity after the first administration of MM-398, from cycle 2 onwards, their dose can be increased in increments of 20 mg/m², up to a maximum of 120 mg/m².

| | |
|---|---|
| Arm C | Patients who do not have the homozygous allele for UGT1A1*28 will receive MM-398 at a dose of 80 mg/m². Patients who are homozygous for UGT1A1 *28 allele and are randomized to Arm C, will receive the first cycle of therapy at a reduced dose of 60 mg/m². If the patient does not experience any drug related toxicity after the first administration of MM-398, from cycle 2 onwards, the dose may be increased to 80 mg/m².<br>MM-398 should be administered prior to 5-FU and leucovorin administration. |

In Arm A, MM-398 will be administered by IV infusion over 90 minutes on the first day of each 3 week cycle, at the investigational site. In Arm C, MM-398 will be administered by an IV infusion over 90 minutes for the first cycle; the infusion time could be reduced to 60 minutes from cycle 2 onwards, if no acute infusion reaction has occurred in cycle 1. Cycle duration is 3 weeks for Arm A and 2 weeks for Arm C. The first cycle Day 1 is a fixed day; subsequent doses should be administered on the first day of each cycle +/−3 days.

Prior to administration, the appropriate dose of MM-398 must be diluted in 5% Dextrose Injection solution (D5W) to a final volume of 500 mL. Care should be taken not to use in-line filters or any diluents other than D5W. MM-398 can be administered using standard PVC-containing intravenous administration bags and tubing.

The actual dose of MM-398 to be administered will be determined by calculating the patient's body surface area at the beginning of each cycle. A +/−5% variance in the calculated total dose will be allowed for ease of dose administration. Since MM-398 vials are single-use vials, site staff must not store any unused portion of a vial for future use and they must discard unused portions of the product.

All patients must be premedicated prior to MM-398 infusion with standard doses of dexamethasone and a 5-HT3 antagonist or other anti-emetics as per standard institutional practices for irinotecan administration. Atropine may be prescribed prophylactically for patients who experienced acute cholinergic symptoms in the previous cycles.

D. Description of 5-FU and Leucovorin

5-Fluorouracil is a pyrimidine antagonist that interferes with nucleic acid biosynthesis. The deoxyribonucleotide of the drug inhibits thymidylate synthetase, thus inhibiting the formation of thymidylic acid from deoxyuridylic acid, thus interfering in the synthesis of DNA. It also interferes with RNA synthesis.

Leucovorin acts as a biochemical cofactor for 1-carbon transfer reactions in the synthesis of purines and pyrimidines. Leucovorin does not require the enzyme dihydrofolate reductase (DHFR) for conversion to tetrahydrofolic acid. The effects of methotrexate and other DHFR-antagonists are inhibited by leucovorin. Leucovorin can potentiate the cytotoxic effects of fluorinated pyrimidines (i.e., fluorouracil and floxuridine). After 5-FU is activated within the cell, it is accompanied by a folate cofactor, and inhibits the enzyme thymidylate synthetase, thus inhibiting pyrimidine synthesis. Leucovorin increases the folate pool, thereby increasing the binding of folate cofactor and active 5-FU with thymidylate synthetase.

FU and leucovorin will be stored and handled according to the country specific package inserts. Commercially available 5-FU and leucovorin will be provided to all patients in the study who are randomized to Arm B and Arm C.

5-FU and leucovorin will be dosed and administered as follows.

| | |
|---|---|
| Arm B | 5-FU will be administered at a dose of 2000 mg/m² as an IV infusion over 24-hours, (+/−30 minutes), every week for 4 weeks (days 1, 8, 15 and 22), followed by 2 weeks of rest, in a 6 week cycle<br>Leucovorin will be administered at a dose of 200 mg/m² (l form) or 400 mg/m² (l + d racemic form) as an IV infusion over 30 minutes, every week for 4 weeks (days 1, 8, 15 and 22), followed by 2 weeks of rest, in a 6 week cycle |
| Arm C | 5-FU will be administered at a dose of 2400 mg/m² as an IV infusion over 46-hours, (+/−60 minutes), every 2 weeks<br>Leucovorin will be administered at a dose of 200 mg/m² (l form) or 400 mg/m² (l + d racemic form) as an IV infusion over 30 minutes, every 2 weeks |

Leucovorin should be reconstituted per the instructions on the package inset or standard institutional guidelines for reconstitution of leucovorin. Leucovorin should be administered prior to the 5-FU infusion.

Actual dose of 5-FU and leucovorin to be administered will be determined by calculating the patient's body surface area prior to each cycle. A +/−5% variance in the calculated total dose will be allowed for ease of dose administration.

After cycle 1, for the start of each new cycle, a window period of +/−3 days will be permitted, and a window period of +/−1 day will be permitted for the Day 8, 15 and 22 infusions.

All patients must be premedicated prior to 5-FU and leucovorin infusion with standard doses of dexamethasone, prochlorperazine or equivalent other anti-emetics as per standard institutional practices for 5-FU administration.

E. Important Treatment Considerations with MM-398

Data from previous MM-398 studies does not show any unexpected toxicity when compared to the active ingredient, irinotecan, which has been studied extensively. The warnings and precautions for the use of irinotecan and the treatment procedures for managing those toxicities are provided below.

Diarrhea

Irinotecan can induce both early and late forms of diarrhea that appear to be mediated by different mechanisms. Early diarrhea (occurring during or shortly after infusion of irinotecan) is cholinergic in nature. It is usually transient and only infrequently severe. It may be accompanied by symptoms of rhinitis, increased salivation, miosis, lacrimation, diaphoresis, flushing, and intestinal hyper-peristalsis that can cause abdominal cramping. For patients who experienced early cholinergic symptoms during the previous cycle of MM-398, prophylactic administration of atropine will be given at the discretion of the investigator.

Late diarrhea (generally occurring more than 24 hours after administration of irinotecan) can be life threatening since it may be prolonged and may lead to dehydration, electrolyte imbalance, or sepsis. Late diarrhea should be treated promptly with loperamide, and octreotide should be considered if diarrhea persists after loperamide. Loss of fluids and electrolytes associated with persistent or severe diarrhea can result in life threatening dehydration, renal insufficiency, and electrolyte imbalances, and may contribute to cardiovascular morbidity. The risk of infectious complications is increased, which can lead to sepsis in patients with chemotherapy-induced neutropenia. Patients with diarrhea should be carefully monitored, given fluid and electrolyte replacement if they become dehydrated, and given antibiotic support if they develop ileus, fever, or severe neutropenia.

Neutropenia

Deaths due to sepsis following severe neutropenia have been reported in patients treated with irinotecan. Neutropenic complications should be managed promptly with antibiotic support. G-CSF may be used to manage neutropenia, with discretion. Patients, who are known to have experienced Grade 3 or 4 neutropenia while receiving prior anti-neoplastic therapy, should be monitored carefully and managed.

Hypersensitivity

Hypersensitivity reactions including severe anaphylactic or anaphylactoid reactions have been observed. Suspected drugs should be withheld immediately and aggressive therapy should be given if hypersensitivity reactions occur.

Colitis/Ileus

Cases of colitis complicated by ulceration, bleeding, ileus, and infection have been observed. Patients experiencing ileus should receive prompt antibiotic support.

Thromboembolism

Thromboembolic events have been observed in patients receiving irinotecan-containing regimens; the specific cause of these events has not been determined.

Pregnancy

The pregnancy category of irinotecan is D. Women of childbearing potential should be advised to avoid becoming pregnant while receiving treatment with irinotecan. If a pregnancy is reported, treatment should be discontinued. The patient should be withdrawn from the study, and the pregnancy should be followed until the outcome becomes known.

Care of Intravenous Site

Care should be taken to avoid extravasation, and the infusion site should be monitored for signs of inflammation. Should extravasation occur, flushing the site with sterile saline and applications of ice are recommended.

Patients at Particular Risk

In clinical trials of the weekly schedule of irinotecan, it has been noted that patients with modestly elevated baseline serum total bilirubin levels (1.0 to 2.0 mg/dL) have had a significantly greater likelihood of experiencing first-cycle grade 3 or 4 neutropenia than those with bilirubin levels that were less than 1.0 mg/dL (50.0% [19/38] versus 17.7% [47/226]; p<0.001). Patients with abnormal glucuronidation of bilirubin, such as those with Gilbert's syndrome, may also be at greater risk of myelosuppression when receiving therapy with irinotecan.

Acute Infusion Associated Reactions

Acute infusion-associated reactions characterized by flushing, shortness of breath, facial swelling, headache, chills, back pain, tightness of chest or throat, and hypotension have been reported in a small number of patients treated with liposome drugs. In most patients, these reactions generally resolve within 24 hours after the infusion is terminated. In some patients, the reaction resolves by slowing the rate of infusion. Most patients who experienced acute infusion reactions to liposome drugs are able to tolerate further infusions without complications.

Other Toxicity Potential

MM-398, the new liposome formulation of irinotecan, is different from irinotecan in unencapsulated formulation, so there is a potential for toxicities other than those caused by irinotecan. All patients should be monitored closely for signs and symptoms indicative of drug toxicity, particularly during the initial administration of treatment.

F. Dose Modification Requirements

Dosing may be held for up to 3 weeks from when it was due, to allow for recovery from toxicity related to the study treatments. If the time required for recovery from toxicity is more than 3 weeks, the patient should be discontinued from the study, unless the patient is benefiting from the study treatment, in which case the patient's continuation on study should be discussed between Investigator and Sponsor or its designee regarding risks and benefits of continuation. If a patient's dose is reduced during the study due to toxicity, it should remain reduced for the duration of the study; dose re-escalation to an earlier dose is not permitted. Any patient who has 2 dose reductions and experiences an adverse event that would require a third dose reduction must be discontinued from study treatment.

Infusion reactions will be monitored. Infusion reactions will be defined according to the National Cancer Institute CTCAE (Version 4.0) definition of an allergic reaction/infusion reaction and anaphylaxis, as defined below:

Grade 1: Transient flushing or rash, drug fever <38° C. (<100.4° F.); intervention not indicated
Grade 2: Intervention or infusion interruption indicated; responds promptly to symptomatic treatment (e.g., antihistamines, NSAIDS, narcotics); prophylactic medications indicated for <24 hrs
Grade 3: Symptomatic bronchospasm, with or without urticaria; parenteral intervention indicated; allergy-related edema/angioedema; hypotension
Grade 4: Life-threatening consequences; urgent intervention indicated Study site policies or the following treatment guidelines shall be used for the management of infusion reactions.

Grade 1

Slow infusion rate by 50%
Monitor patient every 15 minutes for worsening of condition
Grade 2

Stop infusion
Administer diphenhydramine hydrochloride 50 mg IV, acetaminophen 650 mg orally, and oxygen
Resume infusion at 50% of the prior rate once infusion reaction has resolved
Monitor patient every 15 minutes for worsening of condition
For all subsequent infusions, premedicate with diphenhydramine hydrochloride 25-50 mg IV
Grade 3

Stop infusion and disconnect infusion tubing from patient
Administer diphenhydramine hydrochloride 50 mg IV, dexamethasone 10 mg IV, bronchodilators for bronchospasm, and other medications or oxygen as medically necessary
No further treatment with MM-398 will be permitted
Grade 4

Stop the infusion and disconnect infusion tubing from patient
Administer epinephrine, bronchodilators or oxygen as indicated for bronchospasm
Administer diphenhydramine hydrochloride 50 mg IV, dexamethasone 10 mg IV
Consider hospital admission for observation
No further treatment with MM-398 will be permitted For patients who experience a Grade 1 or Grade 2 infusion reaction, future infusions may be administered at a reduced rate (over 120 minutes), with discretion.

For patients who experience a second grade 1 or 2 infusion reaction, administer dexamethasone 10 mg IV. All subsequent infusions should be premedicated with diphenhydramine hydrochloride 50 mg IV, dexamethasone 10 mg IV, and acetaminophen 650 mg orally.

G. MM-398 Dose Modifications for Hematological Toxicities

Prior to initiating a new cycle of therapy, the patients must have:

ANC≥1500/mm$^3$
Platelet count ≥100,000/mm$^3$

Treatment should be delayed to allow sufficient time for recovery and upon recovery, treatment should be administered according to the guidelines in the tables below. If the patient had febrile neutropenia, the ANC must have resolved to ≥1500/mm$^3$ and the patient must have recovered from infection.

TABLE

MM-398 Dose Modifications for Neutrophil Count

| ANC: cells/mm³ (Worst CTCAE grade) | MM-398 Dose for Next Cycle[a] | | |
|---|---|---|---|
| | Arm A: Patients Not Homozygous for UGT1A1*28 | Arm A: Patients Homozygous for UGT1A1*28 [d] Arm C: Patients Not Homozygous for UGT1A1*28 | Arm C: Patients Homozygous for UGT1A1*28 [d] |
| ≥1000 to 1999 (Grade 1 or 2) | 100% of previous dose | 100% of previous dose | 100% of previous dose |
| <1000 (Grade 3/4) or febrile neutropenia | Reduce dose by 20 mg/m² to a minimum dose of 80 mg/m² [b] | Reduce dose to 60 mg/m² for the first occurrence and to 50 mg/m² for the second occurrence [c, d] | Reduce dose to 50 mg/m² for the first occurrence and to 40 mg/m² for the second occurrence [e, d] |

[a] All dose modifications should be based on the worst preceding toxicity
[b] Patients who require a further dose reduction beyond 80 mg/m² must be withdrawn from the study
[c] Patients who require a further dose reduction beyond 50 mg/m² must be withdrawn from the study
[d] Patients who are homozygous for UGT1A1*28 and have had their dose increased should be dose reduced per guidelines for patients who are not homozygous for UGT1A1*28
[e] Patients who require a further dose reduction beyond 40 mg/m² must be withdrawn from the study

TABLE

MM-398 Dose Modifications for Other Hematologic Toxicity

| Worst Toxicity CTCAE Grade | MM-398 Dose for Next Cycle[a] | | |
|---|---|---|---|
| | Arm A: Patients Not Homozygous for UGT1A1*28 | Arm A: Patients Homozygous for UGT1A1*28 [d] Arm C: Patients Not Homozygous for UGT1A1*28 | Arm C: Patients Homozygous for UGT1A1*28 [d] |
| ≤Grade 2 | 100% of previous dose | 100% of previous dose | 100% of previous dose |
| Grade 3/4 | Reduce dose by 20 mg/m² to a minimum dose of 80 mg/m² [b] | Reduce dose to 60 mg/m² for the first occurrence and to 50 mg/m² for the second occurrence [c, d] | Reduce dose to 50 mg/m² for the first occurrence and to 40 mg/m² for the second occurrence [e, d] |

[a] All dose modifications should be based on the worst preceding toxicity
[b] Patients who require a further dose reduction beyond 80 mg/m2 must be withdrawn from the study
[c] Patients who require a further dose reduction beyond 50 mg/m2 must be withdrawn from the study
[d] Patients who are homozygous for UGT1A1*28 and have had their dose increased should be dose reduced per guidelines for patients who are not homozygous for UGT1A1*28
[e] Patients who require a further dose reduction beyond 40 mg/m² must be withdrawn from the study

H. MM-398 Dose Modifications for Non-Hematological Toxicities

Treatment should be delayed until diarrhea resolves to ≤Grade 1, and for other Grade 3 or 4 non-hematological toxicities, until they resolve to Grade 1 or baseline. Guidelines for dose adjustment of MM-398 for drug related diarrhea and other Grade 3 or 4 non-hematological toxicities are provided below. Infusion reactions should be handled as described above.

TABLE

MM-398 Dose Modifications for Diarrhea

| Worst Toxicity CTCAE Grade | MM-398 Dose for Next Cycle[a] | | |
|---|---|---|---|
| | Arm A: Patients Not Homozygous for UGT1A1*28 | Arm A: Patients Homozygous for UGT1A1*28 [d] Arm C: Patients Not Homozygous for UGT1A1*28 | Arm C: Patients Homozygous for UGT1A1*28 [d] |
| Grade 1 or 2 (2-3 stools/day > pretreatment or 4-6 stools/day > pretreatment) | 100% of previous dose | 100% of previous dose | 100% of previous dose |

TABLE-continued

MM-398 Dose Modifications for Diarrhea

| | MM-398 Dose for Next Cycle[a] | | |
|---|---|---|---|
| Worst Toxicity CTCAE Grade | Arm A: Patients Not Homozygous for UGT1A1*28 | Arm A: Patients Homozygous for UGT1A1*28 [d] Arm C: Patients Not Homozygous for UGT1A1*28 | Arm C: Patients Homozygous for UGT1A1*28 [d] |
| Grade 3 (7-9 stools/day > pretreatment) or Grade 4 (>10 stools/day > pretreatment) | Reduce dose by 20 mg/m$^2$ to a minimum dose of 80 mg/m$^2$ [b] | Reduce dose to 60 mg/m$^2$ for the first occurrence and to 50 mg/m$^2$ for the second occurrence[c, d] | Reduce dose to 50 mg/m$^2$ for the first occurrence and to 40 mg/m$^2$ for the second occurrence [e, d] |

[a] All dose modifications should be based on the worst preceding toxicity
[b] Patients who require a further dose reduction beyond 80 mg/m$^2$ must be withdrawn from the study
[c] Patients who require a further dose reduction beyond 50 mg/m$^2$ must be withdrawn from the study
[d] Patients who are homozygous for UGT1A1*28 and have had their dose increased should be dose reduced per guidelines for patients who are not homozygous for UGT1A1*28
[e] Patients who require a further dose reduction beyond 40 mg/m$^2$ must be withdrawn from the study

TABLE

MM-398 Dose Modifications for Non-Hematological Toxicities Other than Diarrhea, Asthenia and Grade 3 Anorexia[d]

| | MM-398 Dose for Next Cycle[a] | | |
|---|---|---|---|
| Worst Toxicity CTCAE Grade | Arm A: Patients Not Homozygous for UGT1A1*28 | Arm A: Patients Homozygous for UGT1A1*28 [e] Arm C: Patients Not Homozygous for UGT1A1*28 | Arm C: Patients Homozygous for UGT1A1*28 [e] |
| Grade 1 or 2 | 100% of previous dose | 100% of previous dose | 100% of previous dose |
| Grade 3 or 4 (except nausea and vomiting) | Reduce dose by 20 mg/m$^2$ to a minimum dose of 80 mg/m$^2$ [b] | Reduce dose to 60 mg/m$^2$ for the first occurrence and to 50 mg/m$^2$ for the second occurrence [c, e] | Reduce dose to 50 mg/m$^2$ for the first occurrence and to 40 mg/m$^2$ for the second occurrence [f, e] |
| Grade 3 or 4 nausea and or vomiting despite anti emetic therapy | Optimize anti-emetic therapy AND reduce dose by 20 mg/m$^2$ to a minimum dose of 80 mg/m$^2$ [b] | Optimize anti-emetic therapy AND reduce dose to 60 mg/m$^2$; if the patient is already receiving 60 mg/m$^2$, reduce dose to 50 mg/m$^2$ [c, e] | Optimize anti-emetic therapy AND reduce dose to 50 mg/m$^2$; if the patient is already receiving 50 mg/m$^2$, reduce dose to 40 mg/m$^2$ [f, e] |

[a] All dose modifications should be based on the worst preceding toxicity
[b] Patients who require a further dose reduction beyond 80 mg/m$^2$ must be withdrawn from the study
[c] Patients who require a further dose reduction beyond 50 mg/m$^2$ must be withdrawn from the study
[d] Asthenia and Grade 3 Anorexia do not require dose modification
[e] Patients who are homozygous for UGT1A1*28 and have had their dose increased should be dose reduced per guidelines for patients who are not homozygous for UGT1A1*28
[f] Patients who require a further dose reduction beyond 40 mg/m$^2$ must be withdrawn from the study I. 5-FU and Leucovorin Dose Modifications (Arm B and Arm C)

Guidelines for 5-FU dose modifications are provided below. No dose adjustments for toxicity are required for leucovorin. Leucovorin must be given immediately prior to each 5-FU dose; hence, if 5-FU dose is held, leucovorin dose should be held as well. In case a patient experiences an infusion reaction, either institutional guidelines or the guidelines provided for MM-398 infusion reaction management should be used.

J. 5-FU Dose Modifications for Hematological Toxicities

Prior to the next dose in a cycle or prior to initiating a new cycle of therapy, the patients must have:

ANC≥1500/mm$^3$

WBC≥3500/mm$^3$

Platelet count ≥75,000/mm$^3$ (according to the European summary of product characteristics for 5-FU, the platelets should have recovered to ≥100,000/mm$^3$ prior to initiating therapy)

Treatment should be delayed to allow sufficient time for recovery and upon recovery, treatment should be administered according to the guidelines provided in the table below. The duration of the cycles is fixed at 6 weeks, and if a patient is unable to receive the D8, D15 or D22 dose due to toxicity, the dose will be considered as skipped.

TABLE

5-FU Dose Modifications for Hematological Toxicities (Arm B & C)

| ANC (cells/mm$^3$) | | Platelets (cells/mm$^3$) | 5-FU Dose for D 8, D 15, D 22$^a$ | 5-FU Dose for Next Cycle$^a$ |
|---|---|---|---|---|
| ≥1000 | and | ≥50,000 | 100% of previous dose | 100% of previous dose |
| 500-999 | Or | <50,000-25,000 | Hold; when resolved, reduce dose by 25%$^b$ | Reduce dose by 25%$^b$ |
| <500 or febrile neutropenia | Or | <25,000 or thrombocytopenia with bleeding | Hold dose; when resolved, reduce dose by 25%$^b$ | Reduce dose by 25%$^b$ |

$^a$All dose modifications should be based on the worst preceding toxicity
$^b$Patients who require more than 2 dose reductions must be withdrawn from the study K. 5-FU Dose Modifications for Non-Hematological Toxicities Treatment should be delayed until all Grade 3 or 4 non-hematological toxicities resolve to Grade 1 or baseline. Guidelines for dose adjustment of 5-FU related toxicities are provided below. The duration of the cycles is fixed at 6 weeks, and if a patient is unable to receive the D8, D15 or D22 dose due to toxicity, the dose will be considered as skipped.

TABLE

5-FU Dose Modifications for Non-Hematological Toxicities Other than Asthenia and Grade 3 Anorexia$^c$ (Arm B & C)

| Worst Toxicity CTCAE Grade | 5-FU Dose for D 8, D 15, D 22$^a$ | 5-FU Dose for Next Cycle$^a$ |
|---|---|---|
| Grade 1 or 2 | 100% of previous dose, except for Grade 2 hand foot syndrome, Grade 2 cardiac toxicity, or any grade neurocerebellar toxicity | 100% of previous dose, except for Grade 2 hand and foot syndrome, Grade 2 cardiac toxicity, or any grade neurocerebellar toxicity |
| Grade 2 hand foot syndrome | Reduce dose by 25%$^b$ | Reduce dose by 25%$^b$ |
| Any grade neurocerebellar or ≥Grade 2 cardiac toxicity | Discontinue therapy | Discontinue therapy |
| Grade 3 or 4 | Hold; when resolved, reduce dose by 25%$^b$, except for Grade 3 or 4 hand foot syndrome | Reduce dose by 25%$^b$, except for Grade 3 or 4 hand foot syndrome |
| Grade 3 or 4 hand foot syndrome | Discontinue therapy | Discontinue therapy |

$^a$All dose modifications should be based on the worst preceding toxicity
$^b$Patients who require more than 2 dose reductions must be withdrawn from the study
$^c$Asthenia and Grade 3 Anorexia do not require dose modification L. Other Toxicities Requiring Special Attention For both 5-FU and MM-398 treatment arms, QTc prolongation that occurs in the setting of diarrhea induced electrolyte imbalance should be treated by with appropriate electrolyte repletion. Once the underlying abnormality is corrected and the ECG abnormalities have reversed, treatment may continue under careful monitoring and with appropriate dose modification for diarrhea as described above.

M. Concomitant Therapy

All concurrent medical conditions and complications of the underlying malignancy will be treated at the discretion of the Investigator according to acceptable local standards of medical care. Patients should receive analgesics, antiemetics, antibiotics, anti-pyretics, and blood products as necessary. Although warfarin-type anticoagulant therapies are permitted, careful monitoring of coagulation parameters is imperative, in order to avoid complications of any possible drug interactions. All concomitant medications, including transfusions of blood products, will be recorded on the appropriate case report form.

Guidelines for treating certain medical conditions are discussed below; however, institutional guidelines for the treatment of these conditions may also be used. The concomitant therapies that warrant special attention are discussed below.

Antiemetic Medications

Dexamethasone and a 5-HT3 blocker (e.g., ondansetron or granisetron) will be administered to all patients as pre-medications unless contraindicated for the individual patient. Antiemetics will also be prescribed as clinically indicated during the study period.

Colony Stimulating Factors

Use of granulocyte colony-stimulating factors (G-CSF) is permitted to treat patients with neutropenia or neutropenic fever; prophylactic use of G-CSF will be permitted only in those patients who have had at least one episode of grade 3 or 4 neutropenia or neutropenic fever while receiving study therapy or have had documented grade 3 or 4 neutropenia or neutropenic fever while receiving prior anti-neoplastic therapy.

Therapy for Diarrhea

Acute diarrhea and abdominal cramps, developing during or within 24 hours after MM-398 administration, may occur as part of a cholinergic syndrome. The syndrome will be treated with atropine. Prophylactic or therapeutic administration of atropine should be considered in patients experiencing cholinergic symptoms during the study.

Diarrhea can be debilitating and on rare occasions is potentially life-threatening. Guidelines developed by an ASCO panel for treating chemotherapy-induced diarrhea are abstracted below.

TABLE

Recommendations for Management of
Chemotherapy Induced Diarrhea

| Clinical Presentation | Intervention |
| --- | --- |
| Diarrhea, any grade | Oral loperamide (2 mg every 2 hours for irinotecan induced diarrhea; 2 mg every 4 hours for 5-FU induced diarrhea): continue until diarrhea-free for ≥12 hours |
| Diarrhea persists on loperamide for >24 hours | Oral fluoroquinolone × 7 days |
| Diarrhea persists on loperamide for >48 hours | Stop loperamide; hospitalize patient; administer IV fluids |
| ANC <500 cells/μL, regardless of fever or diarrhea | Oral fluoroquinolone (continue until resolution of neutropenia) |
| Fever with persistent diarrhea, even in the absence of neutropenia | Oral fluoroquinolone (continue until resolution of fever and diarrhea) |

The synthetic octapeptide octreotide has been shown to be effective in the control of diarrhea induced by fluoropyrimidine-based chemotherapy regimens when administered as an escalating dose by continuous infusion or subcutaneous injection. Octreotide can be administered at doses ranging from 100 micrograms twice daily to 500 micrograms three times daily, with a maximum tolerated dose of 2000 micrograms three times daily in a 5-day regimen. Patients should be advised to drink water copiously throughout treatment.

Other Treatments

Symptomatic treatment for other toxicities should be per institutional guidelines. Prevention of alopecia with cold cap or of stomatitis with iced mouth rinses is allowed.

N. Prohibited Therapy

The following drugs are noted in the irinotecan prescribing information as interacting with irinotecan: St. John's Wort, CYP3A4 inducing anticonvulsants (phenytoin, phenobarbital, and carbamazepine), ketoconazole, itraconazole, troleandomycin, erythromycin, diltiazem and verapamil. Treatment with these agents and any other that interact with irinotecan, should be avoided wherever possible. Because 5-FU interacts with warfarin, caution should be exercised if concomitant use is necessary. Refer to the country specific package inserts of 5-FU and leucovorin for any other drug interactions.

The following therapies are not permitted during the trial:
Other anti-neoplastic therapy, including cytotoxics, targeted agents, endocrine therapy or other antibodies;
Potentially curative radiotherapy; palliative radiotherapy is permitted; and
Any other investigational therapy is not permitted.

O. Laboratory Procedures

Complete Blood Count

A complete blood count (CBC) will be performed locally, and must include a white blood count (WBC) and differential, hemoglobin, hematocrit and platelet count.

Serum Chemistry

Serum chemistry panel will be performed centrally. Additionally, chemistry may also be assessed locally, and local lab results may be used for enrollment and treatment decisions, if central lab results are not available. If local lab results are used for enrollment, then local lab results must be used for all subsequent treatment decisions. Serum chemistry will include electrolytes (sodium, potassium, chloride and bicarbonate), BUN, serum creatinine, glucose, direct and total bilirubin, AST, ALT, alkaline phosphatase, LDH, uric acid, total protein, albumin, calcium, magnesium and phosphate.

CA 19-9

CA 19-9 levels will be measured centrally for all patients.

Pregnancy Test

All women of child bearing potential must undergo a urine or serum pregnancy test.

UGT1A1*28 Allele

A whole blood sample will be collected from all patients at baseline and sent to the central lab to test for UGT1A1*28 allele status. Local lab results may be used if the central lab results are not available at the time of randomization.

Pharmacokinetic Assessments

PK analysis will be done centrally. Plasma PK samples will be collected in Cycle 1, from all patients randomized in this study, at the following timepoints:

Arm A: just prior to infusion, during infusion (at 80 to 90 minutes after start of infusion), between 2 and a half and four hours after the start of infusion and on C1D8

Arm B: one sample at the end of 5-FU infusion (C1D2)

Arm C: just prior to MM-398 infusion, during MM-398 infusion (at 80 to 90 minutes after start of infusion), between 2 and a half and four hours after the start of MM-398 infusion, at the end of 5-FU infusion and on C1D8

In addition, a PK sample will be collected in Cycle 1, any time between 8 and 72 hours following administration of MM-398, from patients randomized to Arm A and Arm C, who provide an additional consent for collection of this sample.

P. Pain Assessment and Analgesic Consumption

Pain assessment and analgesic consumption diaries will be provided to the patients for recording their pain intensity daily on a visual analogue scale and to document their daily analgesic use.

Q. EORTC-OLO-C30

Quality of life will be assessed by the EORTC-QLQ-C30 instrument. The EORTC-QLQ-C30 is a reliable and valid measure of the quality of life of cancer patients in multi-cultural clinical research settings. It incorporates nine multi-item scales: five functional scales (physical, role, cognitive, emotional, and social); three symptom scales (fatigue, pain, and nausea and vomiting); and a global health and quality-of-life scale. Several single-item symptom measures are also included.

Patients will be required to complete the EORTC-QLQ-C30 questionnaire at timepoints outlined in the Schedule of Assessment. On days that the patient is to receive study drug, assessments should be completed prior to study drug administration. Only those patients, for whom validated translations of the EORTC-QLQ-C30 questionnaire are available, will be required to complete the questionnaire.

R. Overall Survival/Post Study Follow-up

Overall survival data will be collected after a patient completes the 30 day follow-up visit, every 1 month (+/−1 week) from the date of the 30 day follow-up visit. Post-discontinuation data to be collected will include: the date of disease progression (if not already documented; if patient discontinued from study treatment for reasons other than objective disease progression, patient should continue to undergo tumor assessment every 6 weeks, until commencement of new anti-neoplastic therapy or progressive disease); documentation of any anticancer treatment patient has received including the dates of any post-discontinuation systemic therapy, radiotherapy, or surgical intervention; and the date of death. All patients must be followed-up until death or study closure, whichever occurs first.

S. Determining the Severity and Relatedness of Adverse Events

Each adverse event will be graded according to the NCI CTCAE V 4.0, which may be found at http://ctep.cancer.gov/reporting/ctc.html. For events not listed in the CTCAE, severity will be designated as mild, moderate, severe or life threatening or fatal, which correspond to Grades 1, 2, 3, 4 and 5, respectively on the NCI CTCAE, with the following definitions:

Mild: an event not resulting in disability or incapacity and which resolves without intervention;

Moderate: an event not resulting in disability or incapacity but which requires intervention;

Severe: an event resulting in temporary disability or incapacity and which requires intervention;

Life-threatening: an event in which the patient was at risk of death at the time of the event Fatal: an event that results in the death of the patient The Investigator must attempt to determine if there exists reasonable possibility that an adverse event is related to the use of the study drug. This relationship should be described as related or non-related.

T. Analysis of the Overall Survival

Overall survival (OS) is the primary endpoint of this study. Overall survival is defined as the time from the date of patient randomization to date of death or the date last known alive. For each patient who is not known to have died as of the data-inclusion cut-off date for a particular analysis, OS will be censored for that analysis at the date of last contact prior to the data cut-off date.

The study primary analysis will involve two pair-wise comparisons of survival between the study treatments, in the ITT population using un-stratified Log Rank Test. The testing will be according to the Bonferroni-Holm procedure which strongly controls the family-wise error rate at 0.05 (two-sided) level [25]:

Reject $H_D^1:S_A(t)=S_B(t)$, i.e. no effect of MM-398 monotherapy relative to control, if the logrank p-value for this test is less than 0.025 or if the logrank p-value for this test is less than 0.05 and the logrank p-value for the comparison between Arm B and Arm C is less than 0.025.

Reject $H_D^2: S_C(t) S_B(t)$, i.e. no effect of MM-398 combination therapy relative to control, if the logrank p-value for this test is less than 0.025 or if the logrank p-value for this test is less than 0.05 and the logrank p-value for the comparison between Arm A and Arm B is less than 0.025.

Kaplan-Meier analyses will be performed on each treatment group to obtain nonparametric estimates of the survival function and the median survival time. Corresponding 95% confidence intervals will be computed using the log-log method. Cox proportional hazards modeling will be used to estimate hazard ratios and corresponding 95% confidence intervals.

The following additional sensitivity analyses will be carried out for overall survival on the ITT population (except as indicated) to evaluate the robustness of the primary analysis results:

log-rank comparisons of treatments on the PP population stratified log rank analyses, using randomization stratification factors [with hazard ratio estimates from stratified Cox modeling]

Wilcoxon Comparisons of Treatments

Cox regression model with stepwise selection (p value to enter <0.25, p-value to remain <0.15) of model terms where treatment and the prognostic factors (noted below) are candidates for inclusion univariate analyses to evaluate potential independent prognostic factors using Cox regression subgroup analyses to examine differences in the effects of treatment in different segments of the study population.

Repeat all analyses (primary and sensitivity) with only patients who enrolled under protocol Version 2 (and later)

Prognostic factors to be examined include: baseline KPS, baseline albumin, ethnicity, geographic location, disease stage at diagnosis, original tumor location, number of prior chemotherapy treatments, prior radiotherapy, prior surgery, time since last treatment, best response on prior treatment, baseline CA 19-9, gender and age.

U. Secondary Efficacy Analyses

Progression Free Survival

PFS is defined as the number of months from the date of randomization to the date of death or progression, whichever occurred earlier (per RECIST 1.1). If neither death nor progression is observed during the study, PFS data will be censored at the last valid tumor assessment.

PFS will be compared between the treatment groups using paired un-stratified log-rank tests. The PFS curves will be estimated using Kaplan-Meier estimates. Estimates of the hazard ratios and corresponding 95% confidence intervals will be obtained using Cox proportional hazard models. Stratified analyses will also be carried out using the randomization stratification factors. Treatment effects adjusting for stratification variables and other prognostic covariates will be explored. In addition, different censoring and missing data imputing methods may be used to perform sensitivity analyses on PFS. Methodology for the sensitivity analyses will be fully specified in the Statistical Analysis Plan.

The analyses will be performed for ITT, PP and EP populations.

Time to Treatment Failure

Time to treatment failure is defined as time from randomization to either disease progression, death or study discontinuation due to toxicity. Kaplan-Meier analyses as specified for analyses of progression free survival will be performed for time to treatment failure.

The analyses will be performed for ITT, PP and EP populations.

Objective Response Rate

The tumor assessment related to ORR will be determined using RECIST v1.1. If the Sponsor requires an independent review of the radiological assessments to support a new drug application or for any other reason, the response status of all patients may be reviewed by an independent panel of clinicians and may be reviewed by the Sponsor or its designee. In case of a discrepancy between the assessment of the independent panel and that of the investigator, the independent panel's assessment will take precedence.

Objective response rate (ORR) for each treatment group will be calculated combining the number of patients with a best overall response of confirmed CR or PR per RECIST. The ORR is the best response recorded from randomization until progression or end of study. The number and percentage of patients experiencing objective response (confirmed CR+PR) at the time of analysis will be presented and the 95% confidence interval for the proportion will be calculated. Objective response rates from the treatment arms will be compared using pair-wise Fisher's Exact Tests. The analyses will be performed for ITT, PP and EP populations.

Tumor Marker Response Analysis

CA 19-9 serum levels will be measured within 7 days before the start of treatment (baseline), and subsequently every 6 weeks. Tumor marker response of CA19-9 will be evaluated by the change of CA19-9 serum levels. Response is defined as a decrease of 50% of CA 19-9 in relation to the baseline level at least once during the treatment period. Only patients with elevated baseline CA 19-9 value (>30 U/mL) will be included in the calculation of tumor marker response rate.

Patient Reported Outcome Analyses

Analysis of the EORTC-QLQ-C30 questionnaires will be performed in accordance with the EORTC guidelines [22].

Safety Analysis

Treatment emergent adverse events will be presented by treatment arm, by patient, by NCI CTCAE grade and by MedDRA system organ class (SOC). Separate listings will be presented for total adverse events, serious adverse events, adverse events related to the study drugs and Grade 3 and 4 adverse events. Laboratory data will be presented by treatment arm and by visit. Abnormal laboratory values will be assessed according to NCI CTCAE grade, where possible. Evaluation of QTc will be done based upon Fridericia's correction method. CTCAE criteria will be applied to the QTcF (i.e. Grade 3=QTc>500 msec). All the safety analyses will be performed by treatment arm, treatment cycle and week, where appropriate. Overall safety will also be evaluated by grade across cycles, SOC and extent of exposure. Additionally, safety analyses will include a comparison between the treatment arms in all patients in the Safety Population:

Number of blood transfusions required
Proportion of patients requiring G-CSF
Adverse events resulting in dose delay or modification
Pharmacokinetics Analysis Pharmacokinetic data will be collected on all patients randomized to either of the MM-398 arms. Plasma concentration-time data for MM-398 will be analyzed using population pharmacokinetic methods. Pharmacokinetic parameters will be estimated by Non-Linear Mixed Effects Modeling using NONMEM®, Version 7, Level 1.0 (ICON Development Solutions, Dublin, Ireland). PK parameters will include plasma $C_{max}$, $T_{max}$, AUC (area under the concentration curve), clearance, volume of distribution, and terminal elimination half-life. The effects of patient specific factors (age, race, gender, body weight, hepatic and renal function measures, ECOG value, etc.) on pharmacokinetic parameters will be evaluated. Population PK/PD methods will be used to assess the relationships between drug exposure and efficacy and/or toxicity (e.g. neutropenia, diarrhea) parameters. Additional exploratory analysis may be performed on the PK samples, to help clarify any safety, efficacy or PK issues related to MM-398 that arise during the course of the study. Concentration levels of 5-FU will be summarized descriptively.

Endnotes

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein. The disclosure of each and every US, international, or other patent or patent application or publication referred to herein is hereby incorporated herein by reference in its entirety.

What is claimed is:

1. A method of treating metastatic adenocarcinoma of the pancreas in a human patient who has previously been treated with gemcitabine, comprising intravenously administering an antineoplastic therapy to the patient once every two weeks, the therapy consisting of
   i) irinotecan sucrose octasulfate salt liposome injection in a dose providing the equivalent of 70 mg/m² of irinotecan free base,
   ii) 200 mg/m² of the (l) form of leucovorin or 400 mg/m² of the (l+d) racemic form of leucovorin, and
   iii) 2400 mg/m² of 5-fluorouracil.

2. The method of claim 1, wherein the metastatic adenocarcinoma of the pancreas has progressed after treatment with gemcitabine.

3. The method of claim 1, wherein the irinotecan sucrose octasulfate salt liposome injection comprises irinotecan sucrose octasulfate salt, phosphatidylcholine, cholesterol, and a polyethyleneglycol-derivatized phosphatidyl-ethanolamine.

4. The method of claim 3, wherein the polyethylene glycol in the polyethyleneglycol-derivatized phosphatidyl-ethanolamine is N-(methoxy-poly(ethyleneglycol) (M.W. 2000)-oxycarbonyl)-distearoylphosphatidylethanolamine.

5. The method of claim 4, wherein the polyethyleneglycol-derivatized phosphatidyl-ethanolamine is in the amount of approximately one polyethyleneglycol derivatized phosphatidyl-ethanolamine molecule for 200 phosphatidylcholine molecules.

6. The method of claim 4, wherein the irinotecan sucrose octasulfate salt liposome injection comprises phosphatidylcholine, cholesterol, and N-(methoxy-poly(ethyleneglycol) (M.W. 2000)-oxycarbonyl)-distearoylphosphatidylethanolamine in a molar ratio of 3:2:0.015.

7. The method of claim 6, further comprising premedicating the human patient with an anti-emetic prior to administering the antineoplastic therapy.

8. The method of claim 6, wherein the irinotecan sucrose octasulfate salt liposome injection is administered followed by the leucovorin, followed by the 5-fluorouracil.

9. The method of claim 8, further comprising premedicating the human patient with an anti-emetic prior to administering the antineoplastic therapy.

10. The method of claim 8, wherein the irinotecan sucrose octasulfate salt liposome injection, leucovorin, and 5-fluorouracil are administered sequentially to the patient beginning on day 1 of a 2-week cycle.

11. The method of claim 10, further comprising premedicating the human patient with an anti-emetic prior to administering the antineoplastic therapy.

12. The method of claim 8, wherein the irinotecan sucrose octasulfate salt liposome injection is administered intravenously over 90 minutes, followed by intravenous administration of leucovorin over 30 minutes, followed by intravenous administration of 5-fluorouracil over 46 hours.

13. The method of claim 12, further comprising premedicating the human patient with an anti-emetic prior to administering the antineoplastic therapy.

14. The method of claim 1, wherein the leucovorin is provided by administering 400 mg/m² of the (l+d) form of leucovorin.

15. The method of claim 14, further comprising premedicating the human patient with an anti-emetic prior to administering the antineoplastic therapy.

* * * * *